United States Patent
Duan et al.

(10) Patent No.: US 6,455,522 B1
(45) Date of Patent: Sep. 24, 2002

(54) CYCLIC SULFONAMIDE DERIVATIVES AS METALLOPROTEINASE INHIBITORS

(75) Inventors: Jingwu Duan, Newark; Lihua Chen, Wilmington; Robert J. Cherney; Carl P. Decicco, both of Newark, all of DE (US); Matthew E. Voss, Lincoln University, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/247,675

(22) Filed: Feb. 10, 1999

Related U.S. Application Data

(60) Provisional application No. 60/074,301, filed on Feb. 11, 1998.

(51) Int. Cl.$^7$ .............. A61K 31/55; C07D 515/02; C07D 513/00; C07D 515/00
(52) U.S. Cl. .............. 514/221; 544/47; 548/122; 540/490; 540/491
(58) Field of Search .............. 540/490, 491; 514/221; 544/47; 548/122

(56) References Cited

U.S. PATENT DOCUMENTS

| | | | | |
|---|---|---|---|---|
| 3,284,450 A | 11/1966 | Kraaijeveld et al. | ........ | 260/243 |
| 3,712,889 A | 1/1973 | Sianesi et al. | ........ | 260/243 |
| 3,770,733 A | 11/1973 | Sianesi et al. | ........ | 260/243 |
| 4,116,964 A | 9/1978 | Zinnes et al. | ........ | 260/294.8 |
| 5,250,679 A | * 10/1993 | Blackburn et al. | ........ | 540/490 |

FOREIGN PATENT DOCUMENTS

| | | | |
|---|---|---|---|
| DE | 2022694 | | 11/1970 |
| EP | 0574758 | | 12/1993 |
| EP | 0644182 | | 3/1995 |
| GB | 2268934 | | 1/1994 |
| WO | 9321170 | | 10/1993 |
| WO | 9424140 | | 10/1994 |
| WO | 9509841 | | 4/1995 |
| WO | 9600214 | | 1/1996 |
| WO | 9815525 | * | 4/1998 |
| WO | 9821186 | | 5/1998 |
| WO | 9906041 | | 2/1999 |

OTHER PUBLICATIONS

Chapman et al., "Hypolipidemic activity of phthalimide derivatives . . . ", *J. Med. Chem.*, vol. 26, No. 2, 1983, pp. 243–246.
Primofiore et al., "Benzisothiazole–1,1–dioxide alkanoic acid derivatives . . . ", *Il Farmaco*, vol. 52, No. 10, 1997, pp. 583–588.
Da Settimo et al, "Acid derivatives of benzisothiazole–1, 1–dioxide . . . ", *Il Farmaco*, vol. 51, No. 4, 1996, pp. 261–267.
Raffa et al., "Acidi eteroarilalcanoici a possible . . . ", *Il Farmaco, Edizione Scientifica*, vol. 34, No. 3, 1979, pp. 199–210 (English Abstract).
Wakefield, D.; Lloyd, A.; The role of cytokines in the pathogenesis of inflammatory eye disease. *Cytokine* 1992, 4(1), 1–5.
Yan, X.; Tezel, G.; Wax, M.B.; Edward, D.P.; Matrix metalloproteinases and tumor necrosis factor alpha in glaucomatous optic nerve hear. *Arch. Ophthalmol,* 2000, 118(5), 666–73.
Mantovani, G.; Maccio, A.; Lai, P.; Massa, E.; Ghiani, M.; Santona, M.C.; Cytokine involvement in cancer anorexia/cachexia: role of megestrol acetate and medroxyprogesterone acetate on cytokine downregulation and improvement of clinical symptoms. *Crit. Rev. Oncog.* 1998, 9(2), 99–106.
Tisdale, M.J.; Biology of cachexia. *J. Natl. Cancer Inst.* 1997, 89(23), 1763–73.
Langhans, W.; Hrupka, B.; Interleukins and tumor necrosis factor as inhibitors of food uptake. *Neuropeptides* 1999, 33(5), 415–24.
Haslett, P.A.; Anticytokine approaches to the treatment of anorexia and cachexia. *Semin. Oncol.* 1998, 25( 2 Suppl. 6), 53–7.
French, S.W.; Mechanisms of alcoholic liver injury. *Can. J. Gastroenterol.* 2000, 14(4), 327–32.
Baumgartner, J.D.; Calandra, T.; Treatment of sepsis: past and future avenues. *Drugs* 1999, 57(2), 127–32.
Salomao, R.; Rigato, O.; Pignatari, A.C., Freudenberg, M.A.; Galanos, C.; Bloodstream infections: epidemiology, pathophysiology, and therapeutic perspectives. *Infection* 1999, 27(1), 1–11.

\* cited by examiner

*Primary Examiner*—Mukund J. Shah
*Assistant Examiner*—Tamthom N. Truong
(74) *Attorney, Agent, or Firm*—David H. Vance; Jing S. Belfield

(57) ABSTRACT

The present application describes novel lactams and derivatives thereof of formula I:

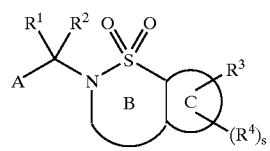

or pharmaceutically acceptable salt forms thereof, wherein rings ring B is a 4–8 membered cyclic sulfonamide containing from 0–3 additional heteroatoms selected from N, O, and S, which are useful as metalloprotease inhibitors.

36 Claims, No Drawings

CYCLIC SULFONAMIDE DERIVATIVES AS METALLOPROTEINASE INHIBITORS

This application claims the benefit of U.S. Provisional Application No. 60/074,301, filed Feb. 11, 1998.

FIELD OF THE INVENTION

This invention relates generally to novel cyclic sulfonamide derivatives as metalloproteinase inhibitors, pharmaceutical compositions containing the same, and methods of using the same.

BACKGROUND OF THE INVENTION

There is now a body of evidence that metalloproteinases (MP) are important in the uncontrolled breakdown of connective tissue, including proteoglycan and collagen, leading to resorption of the extracellular matrix. This is a feature of many pathological conditions, such as rheumatoid and osteoarthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloproteinase), which form inactive complexes with the MP's.

Osteo- and Rheumatoid Arthritis (OA and RA respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A, 1970, 424–434). There are four classes of protein degradative enzymes in mammalian cells: serine, cysteine, aspartic and metalloproteinases. The available evidence supports that it is the metalloproteinases which are responsible for the degradation of the extracellular matrix of articullar cartillage in OA and RA. Increased activities of collagenases and stromelysin have been found in OA cartilage and the activity correlates with severity of the lesion (Mankin et al. Arthritis Rheum. 21, 1978, 761–766, Woessner et al. Arthritis Rheum. 26, 1983, 63–68 and Ibid. 27, 1984, 305–312). In addition, aggrecanase (a newly identified metalloproteinase enzymatic activity) has been identified that provides the specific cleavage product of proteoglycan, found in RA and OA patients (Lohmander L. S. et al. Arthritis Rheum. 36, 1993, 1214–22).

Therefore metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175–184, AP, San Diego, 1990).

Tumor necrosis factor (TNF) is a cell associated cytokine that is processed from a 26 kd precursor form to a 17 kd active form. TNF has been shown to be a primary mediator in humans and in animals, of inflammation, fever, and acute phase responses, similar to those observed during acute infection and shock. Excess TNF has been shown to be lethal. There is now considerable evidence that blocking the effects of TNF with specific antibodies can be beneficial in a variety of circumsatnces including autoimmune diseases such as rheumatoid arthritis (Feldman et al, Lancet, 1994, 344, 1105) and non-insulin dependent diabetes melitus. (Lohmander L. S. et al. Arthritis Rheum. 36, 1993, 1214–22) and Crohn's disease (MacDonald T. et al. Clin. Exp. Immunol. 81, 1990, 301).

Compounds which inhibit the production of TNF are therefore of therapeutic importance for the treatment of inflammatory disorders. Recently it has been shown that a matrix metalloproteinase or family of metalloproteinases, hereafter known as TNF-convertases (TNF-C), as well as other MP's are capable of cleaving TNF from its inactive to active form (Gearing et al Nature, 1994, 370, 555). This invention describes molecules that inhibit this conversion and hence the secretion of active TNF-a from cells. These novel molecules provide a means of mechanism based therapeutic intervention for diseases including but not restricted to septic shock, haemodynamic shock, sepsis syndrom, post ischaemic reperfusion injury, malaria, Crohn's disease, inflammatory bowel diseases, mycobacterial infection, meningitis, psoriasis, congestive heart failure, fibrotic diseases, cachexia, graft rejection, cancer, diseases involving angiogenesis, autoimmune diseases, skin inflammatory diseases, osteo and rheumatoid arthritis, multiple sclerosis, radiation damage, hyperoxic alveolar injury, periodontal disease, HIV and non-insulin dependent diabetes melitus.

Since excessive TNF production has been noted in several disease conditions also charactarized by MMP-mediated tissue degradation, compounds which inhibit both MMPs and TNF production may also have a particular advantage in diseases where both mechansisms are involved.

There are several patents which disclose hydroxamate and carboxylate based MMP inhibitors.

WO95/09841 describes compounds that are hydroxamic acid derivatives and are inhibitors of cytokine production.

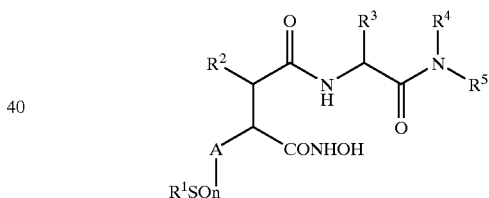

European Patent Application Publication No. 574,758 A1, discloses hydroxamic acid derivatives as collagenase inhibitors having the general formula:

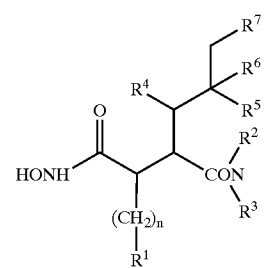

GB 2 268 934 A and WO 94/24140 claim hydroxamate inhibitors of MMPs as inhibitors of TNF production.

The compounds of the current invention act as inhibitors of MMPs, in particular aggrecanase and TNF. These novel molecules are provided as anti-inflammatory compounds and cartilage protecting therapeutics. The inhibiton of aggrecanase, TNF-C, and other metalloproteinases by molecules of the present invention indicates they are anti-inflammatory and should prevent the degradation of cartilage by these enzymes, thereby alleviating the pathological conditions of osteo- and rheumatoid arthritis.

SUMMARY OF THE INVENTION

Accordingly, one object of the present invention is to provide novel cyclic sulfonamides which are useful as metalloprotease inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

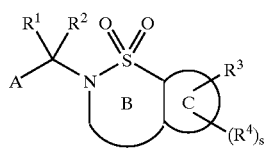

or pharmaceutically acceptable salt or prodrug forms thereof, wherein A, B, C, $R^1$, $R^2$, $R^3$, and $R^4$ are defined below, are effective metalloprotease inhibitors.

DETAILED DESCRIPTION OF PREFERRED EMBODIMENTS

[1] Thus, in a first embodiment, the present invention provides a novel compound of formula I:

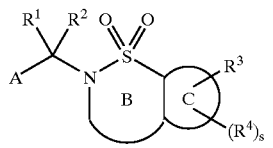

or a stereoisomer or pharmaceutically acceptable salt form thereof, wherein;

A is selected from $COR^5$, $-CO_2H$, $CH(R)CO_2H$, $-CO_2R^6$, $-CONHOH$, $-CH(R)CONHOH$, $-CONHOR^5$, $-CONHOR^6$, $-NHR^a$, $-N(OH)COR^5$, $-SH$, $-CH_2SH$, $-SONHR^a$, $SN_2H_2R^a$, $PO(OH)_2$, and $PO(OH)NHR^a$;

ring B is a 5–10 membered cyclic sulfonamide containing from 0–2 additional heteroatoms selected from O, $NR^b$, and $S(O)_p$, 0–1 carbonyl groups and 0–1 double bonds and ring B is substituted with 0–1 $R^{b'}$;

ring C is phenyl or a 5–6 membered heteroaromatic ring containing from 1–3 heteroatoms selected from O, N, $NR^a$, and $S(O)_p$, provided that when $R^3$ or $R^4$ contains a heteroatom bound to ring C, $R^3$ or $R^4$, respectively, is bound to other than a ring nitrogen;

$R^1$ is selected from H, Q, $C_{1-10}$ alkylene-Q, $C_{2-10}$ alkenylene-Q, $C_{2-10}$ alkynylene-Q, $(CRR')_rO(CRR')_r$—Q, $(CRR')_rNR^a(CRR')_r$—Q, $(CRR')_rC(O)(CRR')_r$—Q, $(CRR')_rC(O)O(CRR')_r$—Q, $(CRR')_rOC(O)(CRR')_r$—Q, $(CRR')_rC(O)NR^a(CRR')_r$—Q, $(CRR')_rNR^aC(O)(CRR')_r$—Q, $(CRR')_rOC(O)O(CRR')_r$—Q, $(CRR')_rOC(O)NR^a(CRR')_r$—Q, $(CRR')_rNR^aC(O)O(CRR')_r$—Q, $(CRR')_rNR^aC(O)NR^a(CRR')_r$—Q, $(CRR')_rS(O)_p(CRR')_r$—Q, $(CRR')_rSO_2NR^a(CRR')_r$—Q, $(CRR')_rNR^aSO_2(CRR')_r$—Q, $(CRR')_rNR^aSO_2NR^a(CRR')_r$—Q, $(CRR')_r$—Q, $(CRR')_rNR^aC(O)(CRR')_{r''}$NHQ, $(CRR')_rNR^aC(O)(CRR')_r$NHC(O)$OR^a$, and $(CRR')_rNR^aC(O)(CRR')_r$NHC(O)(CRR')_r$NHC(O)OR^a$;

R, at each occurrence, is independently selected from H, $CH_3$, $CH_2CH_3$, $CH(CH_3)_2$, $CH=CH_2$, $CH=CHCH_3$, and $CH_2CH=CH_2$;

R', at each occurrence, is independently selected from H, $CH_3$, $CH_2CH_3$, and $CH(CH_3)_2$;

alternatively, R and R' together with the carbon to which they are attached form a cyclopropyl, cyclobutyl or cyclopentyl group;

Q, at each occurence, is selected from H, a $C_{3-13}$ carbocyclic residue substituted with 0–5 $R^c$ and a 5–14 membered heterocyclic system containing from 1–4 heteroatoms selected from the group consisting of N, O, and S and substituted with 0–5 $R^c$;

$R^2$ is selected from H, $C_{1-10}$ alkylene-H, $C_{2-10}$ alkenylene-H, $C_{2-10}$ alkynylene-H, $(CRR')_rO(CRR')_r$—H, $(CRR')_rNR^a(CRR')_r$—H, $(CRR')_rC(O)(CRR')_r$—H, $(CRR')_rC(O)O(CRR')_r$—H, $(CRR')_rOC(O)(CRR')_r$—H, $(CRR')_rC(O)NR^a(CRR')_r$—H, $(CRR')_rNR^aC(O)(CRR')_r$—H, $(CRR')_rOC(O)O(CRR')_r$—H, $(CRR')_rOC(O)NR^a(CRR')_r$—H, $(CRR')_rNR^aC(O)O(CRR')_r$—H, $(CRR')_rNR^aC(O)NR^a(CRR')_r$—H, $(CRR')_rS(O)_p(CRR')_r$—H, $(CRR')_rSO_2NR^a(CRR')_r$—H, $(CRR')_{r'}$ $NR^aSO_2(CRR')_r$—H, and $(CRR')_{r'}NR^aSO_2NR^a(CRR')_r$—H;

$R^3$ is U—X—Y—$X^1$—Z;

U is absent or is selected from: O, $NR^a$, C(O), C(O)O, OC(O), C(O)$NR^a$, $NR^a$C(O), OC(O)O, OC(O)$NR^a$, $NR^a$C(O)O, $NR^a$C(O)$NR^a$, $S(O)_p$, $S(O)_pNR^a$, $NR^a$S(O)$_p$, and $NR^a$SO$_2NR^a$;

X is absent or selected from $C_{1-10}$ alkylene, $C_{2-10}$ alkenylene, and $C_{2-10}$ alkynylene;

$X^1$ is absent or selected from $C_{1-10}$ alkylene, $C_{2-10}$ alkenylene, and $C_{2-10}$ alkynylene;

Y is absent or selected from O, $NR^a$, $S(O)_p$, $S(O)_pNR^a$, C(O)$NR^a$, and C(O), provided that when U and Y are present, X is present;

Z is selected from H, a $C_{3-13}$ carbocyclic residue substituted with 0–5 $R^d$ and a 5–14 membered heterocyclic system containing from 1–4 heteroatoms selected from the group consisting of N, O, and S and substituted with 0–5 $R^d$;

$R^4$, at each occurence, is selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{3-6}$ carbocyclic residue, and a 5–10 membered heterocyclic system containing from 1–4 heteroatoms selected from the group consisting of N, O, and S;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

$R^{a''}$, at each occurrence, is independently selected from $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$ is selected from H, $C_{1-6}$ alkyl, phenyl, benzyl, $C(O)R^a$, $C(O)NR^aR^{a'}$, $S(O)_2NR^aR^{a'}$, and $S(O)_pR^{a''}$;

$R^{b'}$ is selected from H, Q, $C_{1-10}$ alkylene-Q, $C_{2-10}$ alkenylene-Q, $C_{2-10}$ alkynylene-Q, $(CRR')_rO(CRR')_r$—Q, $(CRR')_rNR^a(CRR')_r$—Q, $(CRR')_rC(O)(CRR')_r$—Q, $(CRR')_rC(O)O(CRR')_r$—Q, $(CRR')_rOC(O)$ $(CRR')_r$—Q, $(CRR')_rC(O)NR^a(CRR')_r$—Q, $(CRR')_r$ $NR^aC(O)(CRR')_r$—Q, $(CRR')_rOC(O)O(CRR')_r$—Q, $(CRR')_rOC(O)NR^a(CRR')_r$—Q, $(CRR')_rNR^aC(O)O$ $(CRR')_r$—Q, $(CRR')_rNR^aC(O)NR^a(CRR')_r$—Q, $(CRR')_rS(O)_p(CRR')_r$—Q, $(CRR')_rSO_2NR^a(CRR')_r$—Q, $(CRR')_rNR^aSO_2(CRR')_r$—Q, $(CRR')_rNR^aSO_2NR^a$ $(CRR')_r$—Q, $(CRR')_rNR^aC(O)(CRR')_r$NHQ, $(CRR')_r$ $NR^aC(O)(CRR')_r$NHC(O)$OR^a$, and $(CRR')_rNR^aC(O)$ $(CRR')_r$NHC(O)$(CRR')_r$NHC(O)$OR^a$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aC(O)NR^aR^{a'}$, $OC(O)NR^aR^{a'}$, $R^aNC(O)O$, $S(O)_2NR^aR^{a'}$, $NR^aS(O)_2$ $R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, —CH(=NOH), —C(=NOH)$CH_3$, $(CRR')_sO(CRR')_sR^{c'}$, $(CRR')_sS(O)_p$ $(CRR')_sR^{c'}$, $(CRR')_sNR^a(CRR')_sR^{c'}$, $C_{3-10}$ carbocyclic residue and a 5–14 membered heterocyclic system containing from 1–4 heteroatoms selected from the group consisting of N, O, and S;

$R^{c'}$, at each occurrence, is independently selected from phenyl substituted with 0–3 $R^b$, biphenyl substituted with 0–2 $R^b$, naphthyl substituted with 0–3 $R^b$ and a 5–10 membered heteroaryl system containing from 1–4 heteroatoms selected from the group consisting of N, O, and S and substituted with 0–3 $R^b$;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aC(O)NR^aR^{a'}$, $OC(O)NR^aR^{a'}$, $NR^aC(O)O$, $S(O)_2NR^aR^{a'}$, $NR^aS(O)_2$ $R^{a''}$, $NR^aS(O)_2NR^{a'}$, $OS(O)_2NR^aR^{a'}$, $NR^aS(O)_2O$, $S(O)_pR^{a''}$, $CF_3$, $CF_2CF_3$, $C_{3-10}$ carbocyclic residue and a 5–14 membered heterocyclic system containing from 1–4 heteroatoms selected from the group consisting of N, O, and S;

$R^5$, at each occurrence, is selected from H, $C_{1-10}$ alkyl substituted with 0–2 $R^e$, and $C_{1-8}$ alkyl substituted with 0–2 $R^f$;

$R^e$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_p$ $R^{a''}$, $CF_3$, and $CF_2CF_3$;

$R^f$, at each occurrence, is selected from phenyl substituted with 0–2 $R^e$ and biphenyl substituted with 0–2 $R^e$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —CH($R^8$)OC(=O)$R^9$, —CH($R^8$)OC(=O)$OR^9$, and

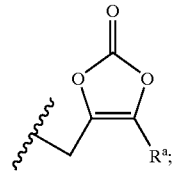

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^g$, $C_{3-8}$ cycloalkyl substituted with 1–2 $R^g$, and phenyl substituted with 0–2 $R^e$;

$R^g$, at each occurrence, is selected from $C_{1-4}$ alkyl, $C_{3-8}$ cycloalkyl, $C_{1-5}$ alkoxy, phenyl substituted with 0–2 $R^e$;

p, at each occurrence, is selected from 0, 1, and 2;

r, at each occurrence, is selected from 0, 1, 2, 3, 4, 5, 6, 7, 8, 9, and 10;

r', at each occurrence, is selected from 1, 2, 3, 4, 5, 6, 7, 8, 9, and 10; and, s, at each occurrence, is selected from 0, 1, 2, and 3.

[2] In a preferred embodiment, the present invention provides a novel compound of formula I, wherein;

A is selected from $COR^5$, —$CO_2H$, $CH_2CO_2H$, —CONHOH, —$CONHOR^5$, —$CONHOR^6$, —N(OH)$COR^5$, —SH, and —$CH_2SH$;

ring B is a 6–8 membered cyclic sulfonamide containing from 0–2 additional heteroatoms selected from O, $NR^b$, and $S(O)_p$, and 0–1 carbonyl groups;

$R^1$ is selected from H, $C_{1-10}$ alkylene-Q, $C_{2-10}$ alkenylene-Q, $C_{2-10}$ alkynylene-Q, $(CH_2)_{r'}O(CH_2)_r$—Q, $(CH_2)_{r'}$ $NR^a(CH_2)_r$—Q, $(CH_2)_rC(O)(CH_2)_r$—Q, $(CH_2)_rC(O)$ $NR^a(CH_2)_r$—Q, $(CH_2)_rNR^aC(O)(CH_2)_r$—Q, $(CH_2)_r$ $OC(O)NR^a(CH_2)_r$—Q, $(CH_2)_rNR^aC(O)O(CH_2)_r$—Q, $(CH_2)_rNR^aC(O)NR^a(CH_2)_r$—Q, $(CH_2)_rS(O)_p(CH_2)_r$—Q, $(CH_2)_rSO_2NR^a(CH_2)_r$—Q, $(CH_2)_{r'}$ $NR^aSO_2$ $(CH_2)_r$—Q, and $(CH_2)_rNR^aSO_2NR^a(CH_2)_r$—Q;

Q is selected from H, a $C_{3-10}$ carbocyclic residue substituted with 0–5 $R^c$ and a 5–10 membered heterocyclic system containing from 1–4 heteroatoms selected from the group consisting of N, O, and S and substituted with 0–5 $R^c$;

$R^2$ is selected from H, $C_{1-6}$ alkylene-H, $C_{2-6}$ alkenylene-H, $C_{2-6}$ alkynylene-H, $(CH_2)_rO(CH_2)_r$—H, $(CH_2)_{r'}$ $NR^a(CH_2)_r$—H, $(CH_2)_rC(O)(CH_2)_r$—H, $(CH_2)_rC(O)$ $NR^a(CH_2)_r$—H, $(CH_2)_{r'}NR^aC(O)(CH_2)_r$—H, $(CH_2)_{r'}$ $SO_2NR^a(CH_2)_r$—H, and $(CH_2)_{r'}NR^aSO_2(CH_2)_r$—H;

U is absent or is selected from: O, $NR^a$, C(O), $C(O)NR^a$, $NR^aC(O)$, OC(O)O, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from $C_{1-6}$ alkylene, $C_{2-6}$ alkenylene, $C_{2-6}$ alkynylene;

$X^1$ is absent or selected from $C_{1-6}$ alkylene, $C_{2-6}$ alkenylene, and $C_{2-6}$ alkynylene;

Z is selected from H, a $C_{5-10}$ carbocyclic residue substituted with 0–5 $R^d$ and a 5–10 membered heterocyclic system containing from 1–4 heteroatoms selected from the group consisting of N, O, and S and substituted with 0–5 $R^d$;

$R^4$, at each occurrence, is selected from $C_{1-6}$ alkyl, $OR^a$, Cl, F, Br, I, =O, CN, $NO_2$, $NR^aR^{a'}$, $C(O)R^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, and a 5–10 membered heterocyclic system containing from 1–4 heteroatoms selected from the group consisting of N, O, and S;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{5-10}$ carbocyclic residue and a 5–10 membered heterocyclic system containing from 1–4 heteroatoms selected from the group consisting of N, O, and S;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{3-10}$ carbocyclic residue and a 5–10 membered heterocyclic system containing from 1–4 heteroatoms selected from the group consisting of N, O, and S;

r, at each occurrence, is selected from 0, 1, 2, 3, 4, and 5; and, r', at each occurrence, is selected from 1, 2, 3, 4, and 5.

[3] In a more preferred embodiment, the present invention provides a novel compound of formula I, wherein;

A is selected from —$CO_2H$, $CH_2CO_2H$, —CONHOH, —$CONHOR^5$, and —$N(OH)COR^5$;

ring B is a 6–8 membered cyclic sulfonamide containing from 0–1 additional heteroatoms selected from O, $NR^b$, and $S(O)_p$, and 0–1 carbonyl groups;

ring C is phenyl or a 5–6 membered heteroaromatic ring containing from 1–2 heteroatoms selected from O, N, $NR^a$, and $S(O)_p$, provided that when $R^3$ or $R^4$ contains a heteroatom bound to ring C, $R^3$ or $R^4$, respectively, is bound to other than a ring nitrogen;

Q is selected from H, a $C_{5-10}$ carbocyclic residue substituted with 0–3 $R^c$ and a 5–10 membered heterocyclic system containing from 1–4 heteroatoms selected from the group consisting of N, O, and S and substituted with 0–3 $R^c$;

$R^2$ is selected from H, $CH_3$, and $CH_2CH_3$;

U is absent or is selected from: O, $NR^a$, C(O), $C(O)NR^a$, $NR^aC(O)$, $NR^aC(O)NR^a$, $S(O)_p$, $S(O)_pNR^a$, $NR^aS(O)_p$, and $NR^aSO_2NR^a$;

X is absent or selected from $C_{1-2}$ alkylene, $C_{2-3}$ alkenylene, and $C_{2-3}$ alkynylene;

$X^1$ is absent or selected from $C_{1-2}$ alkylene, $C_{2-3}$ alkenylene, and $C_{2-3}$ alkynylene;

Z is selected from H, a $C_{5-6}$ carbocyclic residue substituted with 0–5 $R^d$ and a 5–10 membered heterocyclic system containing from 1–4 heteroatoms selected from the group consisting of N, O, and S and substituted with 0–5 $R^d$; and, $R^4$, at each occurrence, is selected from $C_{1-6}$ alkyl, $OR^a$, Cl, F, Br, I, =O, CN, $NO_2$, $NR^aR^{a'}$, $C(O)R^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, and a 5–6 membered heterocyclic system containing from 1–4 heteroatoms selected from the group consisting of N, O, and S.

[4] In a further preferred embodiment, the present invention provides a novel compound of formula I, wherein;

A is selected from —$CO_2H$, $CH_2CO_2H$, —CONHOH, and —$CONHOR^5$;

ring B is a 6–7 membered cyclic sulfonamide containing from 0–1 additional heteroatoms selected from $NR^b$;

ring C is phenyl;

$R^1$ is selected from H, $C_{1-6}$ alkylene-Q, $C_{2-6}$ alkenylene-Q, $C_{2-6}$ alkynylene-Q, $(CH_2)_rO(CH_2)_{r'}$—Q, $(CH_2)_r$ $NR^a(CH_2)_{r'}$—Q, $(CH_2)_rC(O)(CH_2)_{r'}$—Q, $(CH_2)_rC(O)NR^a(CH_2)_{r'}$—Q, $(CH_2)_{r'}NR^aC(O)(CH_2)_{r'}$—Q, $(CH_2)_{r'}OC(O)NR^a(CH_2)_{r'}$—Q, $(CH_2)_{r'}NR^aC(O)O(CH_2)_{r'}$—Q, $(CH_2)_{r'}NR^aC(O)NR^a(CH_2)_{r'}$—Q, $(CH_2)_{r'}S(O)_p(CH_2)_{r'}$—Q, $(CH_2)_{r'}SO_2NR^a(CH_2)_{r'}$—Q, $(CH_2)_{r'}NR^aSO_2(CH_2)_{r'}$—Q, and $(CH_2)_{r'}NR^aSO_2NR^a(CH_2)_r$—Q;

Q is selected from H, a $C_{5-6}$ carbocyclic residue substituted with 0–3 $R^c$ and a 5–6 membered heterocyclic system containing from 1–4 heteroatoms selected from the group consisting of N, O, and S and substituted with 0–3 $R^c$;

$R^2$ is H;

X is absent or selected from $CH_2$ and $CH_2CH_2$;

$X^1$ is absent;

Y is absent or selected from $S(O)_pNR^a$ and $C(O)NR^a$, provided that when U and Y are present, X is present;

Z is selected from H, phenyl substituted with 0–5 $R^d$ and a 5–10 membered aromatic heterocyclic system containing from 1–4 heteroatoms selected from the group consisting of N, O, and S and substituted with 0–5 $R^d$;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{5-6}$ carbocyclic residue and a 5–6 membered heterocyclic system containing from 1–4 heteroatoms selected from the group consisting of N, O, and S;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{3-6}$ carbocyclic residue and a 5–6 membered heterocyclic system containing from 1–4 heteroatoms selected from the group consisting of N, O, and S; and, s, at each occurrence, is selected from 0 and 1.

[5] In a further preferred embodiment, the present invention provides a novel compound of formula Ia;

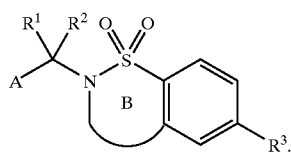

[6] In an even further preferred embodiment, the present invention provides novel compounds selected from:

4,5-dihydro-N-hydroxy-1,2,5-benzothiadiazepine-2(3H)-acetamide-1,1-dioxide;
4,5-dihydro-N-hydroxy-7-methoxy-1,2,5-benzothiadiazepine-2(3H)-acetamide-1,1-dioxide;
(R)-4,5-dihydro-N-hydroxy-alpha-methyl-1,2,5-benzothiadiazepine-2(3H)-acetamide-1,1-dioxide;
(R)-4,5-dihydro-N-hydroxy-7-methoxy-alpha-methyl-1,2,5-benzothiadiazepine-2(3H)-acetamide-1,1-dioxide;
(R)-4,5-dihydro-N-hydroxy-7-methoxy-alpha-(1-methylethyl)-1,2,5-benzothiadiazepine-2(3H)-acetamide-1,1-dioxide;
N-hydroxy-2(R)-[7-(3,5-dimethylbenzyloxy)-2,3,4,5-tetrahydrobenzo[1,2,5-f]thiadiazepine-1,1-dioxide]-propanamide;
N-hydroxy-2(R)-[7-(3,5-dichlorobenzyloxy)-2,3,4,5-tetrahydrobenzo[1,2,5-f]thiadiazepine-1,1-dioxide]-propanamide;
N-hydroxy-2(R)-[7-(3,5-dimethoxybenzyloxy)-2,3,4,5-tetrahydrobenzo[1,2,5-f]thiadiazepine-1,1-dioxide]-propanamide;
N-hydroxy-2(R)-[7-(3,5-dibromobenzyloxy)-2,3,4,5-tetrahydrobenzo[1,2,5-f]thiadiazepine-1,1-dioxide]-propanamide;
N-hydroxy-2(R)-[7-(3,5-diethoxybenzyloxy)-2,3,4,5-tetrahydrobenzo[1,2,5-f]thiadiazepine-1,1-dioxide]-propanamide;
N-hydroxy-2(R)-[7-(2,6-dichloropyridyl-4-methyleneoxy)-2,3,4,5-tetrahydrobenzo[1,2,5-f]thiadiazepine-1,1-dioxide]-propanamide;
N-hydroxy-2(R)-[7-(3-amino-5-methylbenzyloxy)-2,3,4,5-tetrahydrobenzo[1,2,5-f]thiadiazepine-1,1-dioxide]-propanamide;
N-hydroxy-2(R)-[7-(3,5-dimethylbenzyloxy)-2,3,4,5-tetrahydrobenzo[1,2,5-f]thiadiazepine-1,1-dioxide]-3-methylbutanamide;
N-hydroxy-2(R)-[7-(3,5-dimethoxybenzyloxy)-2,3,4,5-tetrahydrobenzo[1,2,5-f]thiadiazepine-1,1-dioxide]-3-methylbutanamide;
N-hydroxy-2(R)-[7-(3,5-diethoxybenzyloxy)-2,3,4,5-tetrahydrobenzo[1,2,5-f]thiadiazepine-1,1-dioxide]-3-methylbutanamide;
N-hydroxy-2(R)-[7-(4,5-dimethylthiazolyl-2-methyleneoxy)-2,3,4,5-tetrahydrobenzo[1,2,5-f]thiadiazepine-1,1-dioxide]-3-methylbutanamide;
N-hydroxy-2(R)-[7-(3,5-dimethylbenzyloxy)-2,3,4,5-tetrahydrobenzo[1,2,5-f]thiadiazepine-1,1-dioxide]-4-methylpentanamide;
N-hydroxy-2(R)-[7-(3,5-dibromobenzyloxy)-2,3,4,5-tetrahydrobenzo[1,2,5-f]thiadiazepine-1,1-dioxide]-4-methylpentanamide;
N-hydroxy-2(R)-[7-(2-nitrophenoxy)-2,3,4,5-tetrahydrobenzo[1,2,5-f]thiadiazepine-1,1-dioxide]-4-methylpentanamide;
N-hydroxy-2(R)-[7-(2-aminophenoxy)-2,3,4,5-tetrahydrobenzo[1,2,5-f]thiadiazepine-1,1-dioxide]-4-methylpentanamide;
N-hydroxy-2(R)-[7-(2,6-dichloropyridyl-4-methyleneoxy)-2,3,4,5-tetrahydrobenzo[1,2,5-f]thiadiazepine-1,1-dioxide]-4-methylpentanamide;
N-hydroxy-2(R)-[7-(pyridyl-4-methyleneoxy)-2,3,4,5-tetrahydrobenzo[1,2,5-f]thiadiazepine-1,1-dioxide]-4-methylpentanamide;
N-hydroxy-2(R)-[7-(3,5-dichlorobenzyloxy)-2,3,4,5-tetrahydrobenzo[1,2,5-f]thiadiazepine-1,1-dioxide]-4-methylpentanamide;
N-hydroxy-2(R)-[7-(3,5-dimethoxybenzyloxy)-2,3,4,5-tetrahydrobenzo[1,2,5-f]thiadiazepine-1,1-dioxide]-4-methylpentanamide;
N-hydroxy-2(R)-[7-(3,5-diethoxybenzyloxy)-2,3,4,5-tetrahydrobenzo[1,2,5-f]thiadiazepine-1,1-dioxide]-4-methoxycarbonylbutanamide;
N-hydroxy-2(R)-[7-(3,5-dimethoxybenzyloxy)-2,3,4,5-tetrahydrobenzo[1,2,5-f]thiadiazepine-1,1-dioxide]-4 methoxycarbonylbutanamide;
N-hydroxy-2(R)-[7-amino-2,3,4,5-tetrahydro-benzo[1,2,5-f]thiadiazepine-1,1-dioxide]-4-methylpentamide;
N-hydroxy-2(R)-[7-(N-acetylamino)-2,3,4,5-tetrahydro-benzo[1,2,5-f]thiadiazepine-1,1-dioxide]-4-methylpentamide;
N-hydroxy-2(R)-[7-(N-(2-phenylacetylamino)-2,3,4,5-tetrahydro-benzo[1,2,5-f]thiadiazepine-1,1-dioxide]-4-methylpentamide;
N-hydroxy-2(R)-[2,3,4,5-tetrahydro-benzo[1,2,5-f]thiadiazepine-1,1-dioxide]-4-methylpentamide;
N-hydroxy-2(R)-[7-(N-(3,5-dimethoxymethyleneamino)-2,3,4,5-tetrahydro-benzo[1,2,5-f]thiadiazepine-1,1-dioxide]-4-methylpentamide;
N-hydroxy-2(R)-[7-(N-(3,5-dimethylphenylmethyleneamino)-2,3,4,5-tetrahydro-benzo[1,2,5-f]thiadiazepine-1,1-dioxide]propylamide;
N-hydroxy-2(R)-[7-(N-benzoylamino)-2,3,4,5-tetrahydro-benzo[1,2,5-f]thiadiazepine-1,1-dioxide]propylamide;
N-hydroxy-2(R)-[7-(N-3,5-dimethoxybenzoylamino)-2,3,4,5-tetrahydro-benzo[1,2,5-f]thiadiazepine-1,1-dioxide]propylamide;
N-hydroxy-2(R)-[7-(N-3,5-dimethylbenzoylamino)-2,3,4,5-tetrahydro-benzo[1,2,5-f]thiadiazepine-1,1-dioxide]propylamide;
N-hydroxy-2(R)-[7-(phenylmethyleneoxy)-2,3,4,5-tetrahydro-benzo[1,2,5-f]thiadiazeine-1,1-dioxide]-2-[(3,4,4-trimethyl-2,5-dioxa-1-imidazolidinyl)methyl]acetamide;
N-hydroxy-2(R)-[7-(3,5-dimethoxyphenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl)methyl]acetamide;
N-hydroxy-2(R)-[7-(3,5-dimethylphenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl)methyl]acetamide;
N-hydroxy-2(R)-[7-(3,5-dibromophenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl)methyl]acetamide;
(R)-3,4-Dihydro-N-Hydroxy-alpha-(1-methylethyl)-2H-1,2-benzothiazine-2-acetamide-1,1-dioxide;
(R)-3,4-Dihydro-N-Hydroxy-alpha-2H-1,2-benzothiazine-2-acetamide-1,1-dioxide;
N-hydroxy-2(R)-[7-(3,5-dimethoxybenzyloxy)-2,3,4,5-tetrahydrobenzo[1,2,5-f]thiadiazepine-1,1-dioxide]-5-methoxycarbonylpentanamide;
N-hydroxy-2(R)-[7-(3,5-diethoxybenzyloxy)-2,3,4,5-tetrahydrobenzo[1,2,5-f]thiadiazepine-1,1-dioxide]-5-methoxycarbonylpentanamide;

N-hydroxy-2(R)-[7-(3,5-dimethoxybenzyloxy)-2,3,4,5-tetrahydrobenzo[1,2,5-f]thiadiazepine-1,1-dioxide]-6-methoxycarbonylhexanamide;
N-hydroxy-2(R)-[7-(3,5-dimethoxybenzyloxy)-2,3,4,5-tetrahydrobenzo[1,2,5-f]thiadiazepine-1,1-dioxide]-6-hydroxycarbonylhexanamide;
N-hydroxy-2(R)-[7-(4-nitrophenoxy)-2,3,4,5-tetrahydrobenzo[1,2,5-f]thiadiazepine-1,1-dioxide]-propanamide;
N-hydroxy-2(R)-[7-(4-aminophenoxy)-2,3,4,5-tetrahydrobenzo[1,2,5-f]thiadiazepine-1,1-dioxide]-propanamide;
N-hydroxy-2(R)-[7-(3-methyl-4-nitrophenoxy)-2,3,4,5-tetrahydrobenzo[1,2,5-f]thiadiazepine-1,1-dioxide]-propanamide;
N-hydroxy-2(R)-[7-(2-nitrophenoxy)-2,3,4,5-tetrahydrobenzo[1,2,5-f]thiadiazepine-1,1-dioxide]-4-methylpentanamide;
N-hydroxy-2(R)-[7-(2-aminophenoxy)-2,3,4,5-tetrahydrobenzo[1,2,5-f]thiadiazepine-1,1-dioxide]-4-methylpentanamide;
N-hydroxy-2(R)-[7-(3-nitrophenoxy)-2,3,4,5-tetrahydrobenzo[1,2,5-f]thiadiazepine-1,1-dioxide]-propanamide;
N-hydroxy-2(R)-[7-phenoxy-2,3,4,5-tetrahydrobenzo[1,2,5-f]thiadiazepine-1,1-dioxide]-propanamide;
N-hydroxy-2(R)-[7-(4-methylthio-phenoxy)-2,3,4,5-tetrahydrobenzo[1,2,5-f]thiadiazepine-1,1-dioxide]-propanamide;
N-hydroxy-2(R)-[7-(4-methoxyphenoxy)-2,3,4,5-tetrahydrobenzo[1,2,5-f]thiadiazepine-1,1-dioxide]-propanamide;
N-hydroxy-2(R)-[7-(4-trifluoromethylphenoxy)-2,3,4,5-tetrahydrobenzo[1,2,5-f]thiadiazepine-1,1-dioxide]-propanamide;
N-hydroxy-2(R)-[7-(4-methylsulfonylphenoxy)-2,3,4,5-tetrahydrobenzo[1,2,5-f]thiadiazepine-1,1-dioxide]-propanamide;
N-hydroxy-2(R)-[7-(4-methoxycarbonylphenoxy)-2,3,4,5-tetrahydrobenzo[1,2,5-f]thiadiazepine-1,1-dioxide]-propanamide;
N-hydroxy-2(R)-[7-(4-phenylphenoxy)-2,3,4,5-tetrahydrobenzo[1,2,5-f]thiadiazepine-1,1-dioxide]-propanamide;
N-hydroxy-2(R)-[7-(benzyloxy)-2,3,4,5-tetrahydro-benzo[1,2,5-f]thiadiazepine 1,1-dioxide]-2-[(5,5-dimethyl-2,4-dioxa-3-oxazolidinyl)methyl]acetamide;
N-hydroxy-2(R)-[7-(benzyloxy)-2,3,4,5-tetrahydro-benzo[1,2,5-f]thiadiazepine 1,1-dioxide]-3-N-(2-hydroxy-2-methylpropylamidyl)propylamide;
N-hydroxy-2(R)-[7-(benzyloxy)-2,3,4,5-tetrahydro-benzo[1,2,5-f]thiadiazepine 1,1-dioxide]-6-N-[(1,1-dimethylethoxy)carbonyl]hexylamide;
N-hydroxy-2(R)-[7-(3,5-dimethoxybenzyloxy)-2,3,4,5-tetrahydro-benzo[1,2,5-f]thiadiazepine 1,1-dioxide]-6-N-[(1,1-dimethylethoxy)carbonyl]hexylamide;
N-hydroxy-2(R)-[7-(3,5-dimethoxybenzyloxy)-2,3,4,5-tetrahydro-benzo[1,2,5-f]thiadiazepine 1,1-dioxide]-6-amino-hexylamide;
N-hydroxy-2(R)-[7-(3,5-dimethoxybenzyloxy)-2,3,4,5-tetrahydro-benzo[1,2,5-f]thiadiazepine 1,1-dioxide]-6-N-(acetamidyl)-hexylamide;
N-hydroxy-2(R)-[7-(3,5-dimethoxybenzyloxy)-2,3,4,5-tetrahydro-benzo[1,2,5-f]thiadiazepine 1,1-dioxide]-6-N-(methanesulfonyl)-hexylamide;
N-hydroxy-2(R)-[7-(2,6-dimethoxypyridyl-4-methyleneoxy)-2,3,4,5-tetrahydro-benzo[1,2,5-f] thiadiazepine 1,1-dioxide]-6-N-[(1,1-dimethylethoxy)carbonyl]hexylamide;
N-hydroxy-2(R)-[7-(2,6-dimethoxypyridyl-4-methyleneoxy)-2,3,4,5-tetrahydro-benzo[1,2,5-f] thiadiazepine 1,1-dioxide]-6-aminohexylamide;
N-hydroxy-2(R)-[7-(3,5-dimethoxybenzyloxy)-2,3,4,5-tetrahydro-benzo[1,2,5-f]thiadiazepine 1,1-dioxide]-6-N-(benzenesulfonyl)-hexylamide;
N-hydroxy-2(R)-[7-(3,5-dimethoxybenzyloxy)-2,3,4,5-tetrahydro-benzo[1,2,5-f]thiadiazepine 1,1-dioxide]-6-N-(butylsulfonyl)-hexylamide;
N-hydroxy-2(R)-[7-(3,5-dimethoxybenzyloxy)-2,3,4,5-tetrahydro-benzo[1,2,5-f]thiadiazepine 1,1-dioxide]-6-N-[(3,5-dimethyl-4-isoxazolyl)sulfonyl]-hexylamide;
N-hydroxy-2(R)-[7-(3,5-dimethoxybenzyloxy)-2,3,4,5-tetrahydro-benzo[1,2,5-f]thiadiazepine 1,1-dioxide]-6-N-[(5-chloro-1,3-dimethyl-1H-pyrazol-4-yl)sulfonyl]-hexylamide;
N-hydroxy-2(R)-[7-phenyl-2,3,4,5-tetrahydro-benzo[1,2,5-f]thiadiazepine 1,1-dioxide]propylamide;
N-hydroxy-2(R)-[7-(2-trifluromethylphenyl)-2,3,4,5-tetrahydro-benzo[1,2,5-f]thiadiazepine 1,1-dioxide]propylamide;
N-hydroxy-2(R)-[7-(phenylethynyl)-2,3,4,5-tetrahydro-benzo[1,2,5-f]thiadiazepine 1,1-dioxide]propylamide; and,
N-hydroxy-2(R)-[7-(4-biphenylyl)-2,3,4,5-tetrahydro-benzo[1,2,5-f]thiadiazepine 1,1-dioxide]propylamide;

or a pharmaceutically acceptable salt form thereof.

In another embodiment, the present invention provides a novel compound selected from the formulas:

-continued
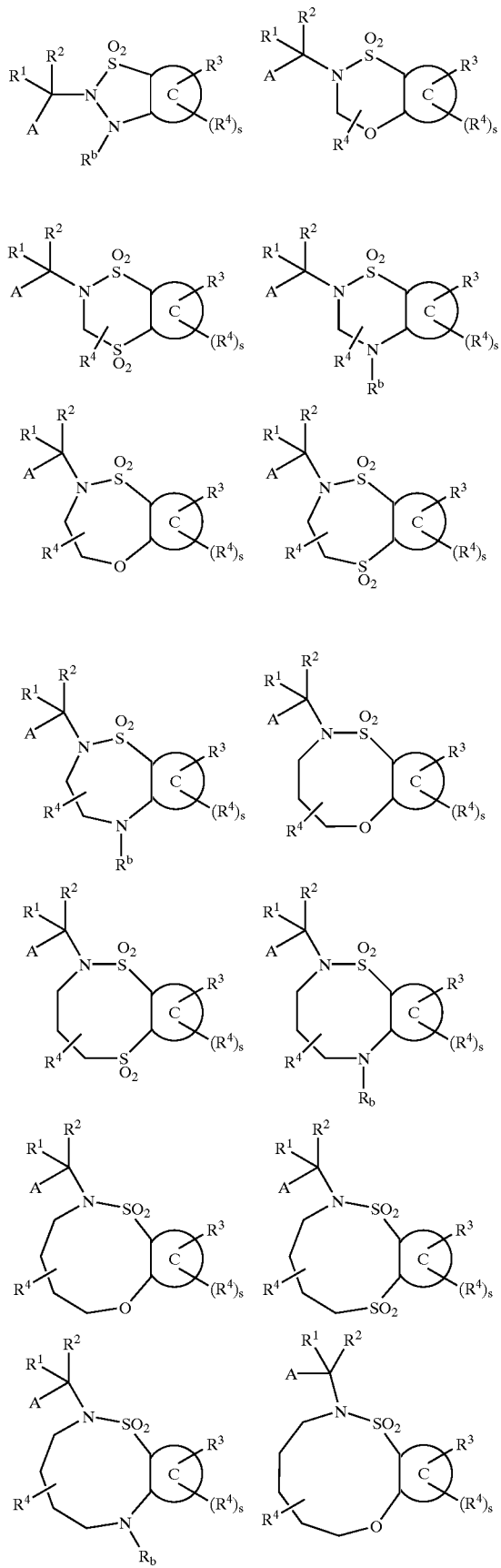
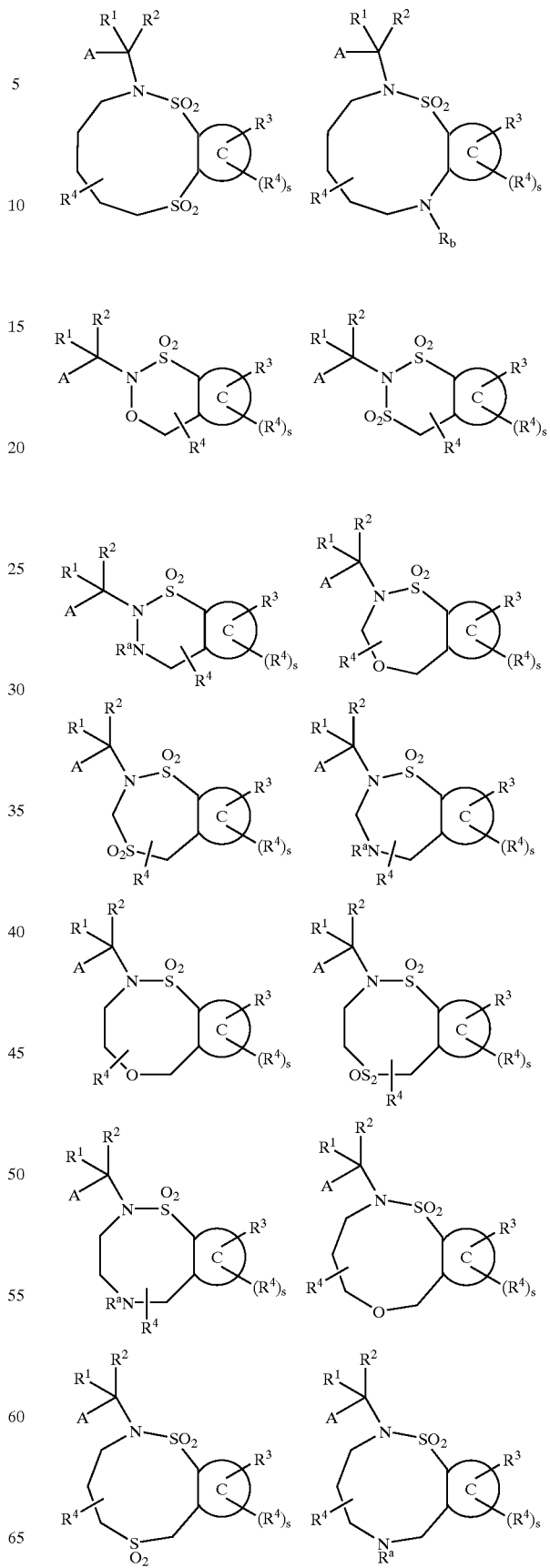

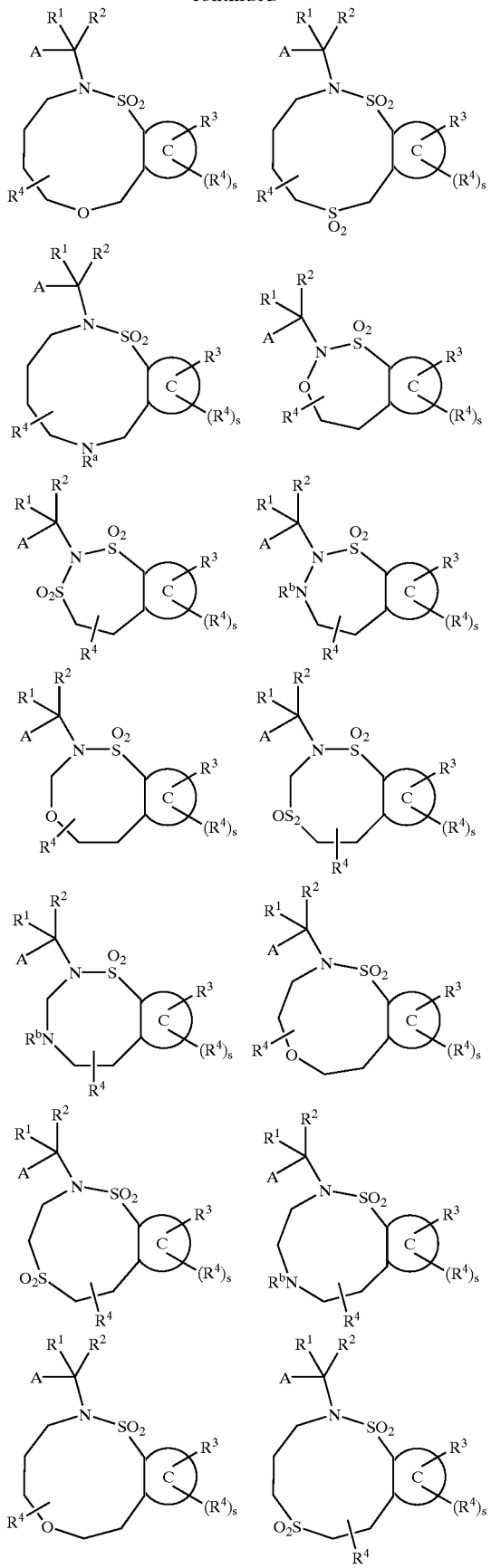
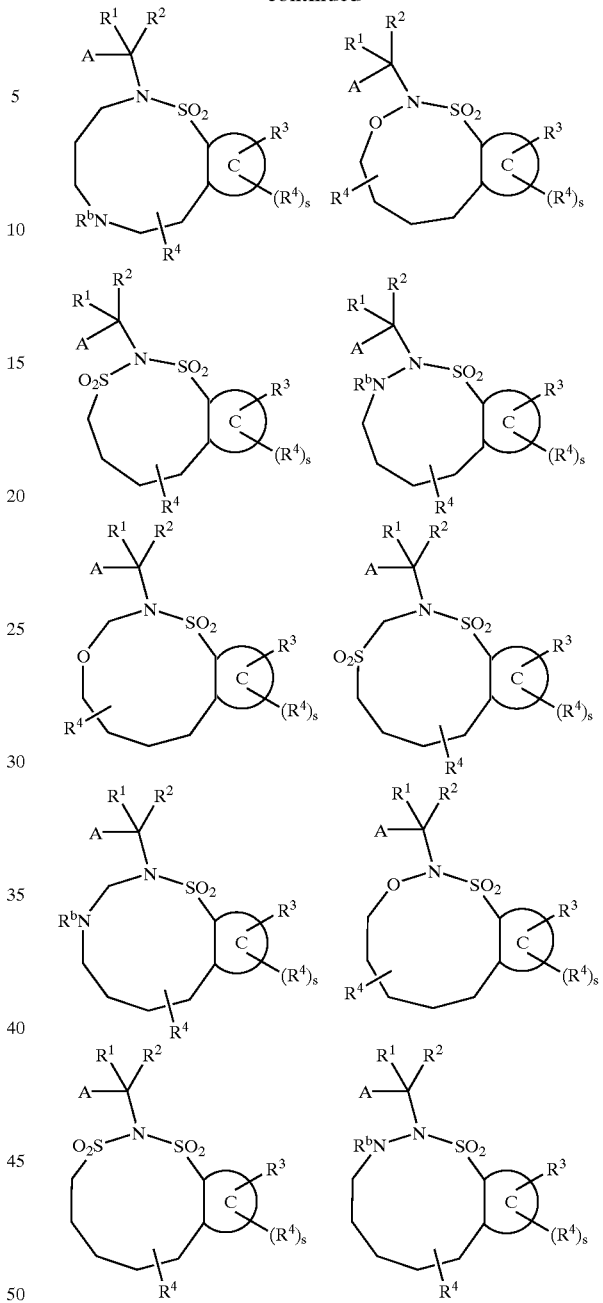

or a pharmaceutically acceptable salt form thereof.

In another embodiment, the present invention provides a novel pharmaceutical composition, comprising: a pharmaceutically acceptable carrier and a therapeutically effective amount of a compound of formula (I) or a pharmaceutically acceptable salt form thereof.

In another embodiment, the present invention provides a novel method for treating or preventing an inflammatory disorder, comprising: administering to a patient in need thereof a therapeutically effective amount of a compound of formula (I) or a pharmaceutically acceptable salt form thereof.

In another embodiment, the present invention provides a novel method of treating a condition or disease mediated by MMPs, TNF, aggrecanase, or a combination thereof in a mammal, comprising: administering to the mammal in need of such treatment a therapeutically effective amount of a compound of formula (I) or a pharmaceutically acceptable salt form thereof.

In another embodiment, the present invention provides a novel method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of formula (I) or a pharmaceutically acceptable salt form thereof.

In another embodiment, the present invention provides a novel method of treating a condition or disease wherein the disease or condition is referred to as fever, cardiovascular effects, hemorrhage, coagulation, cachexia, anorexia, alcoholism, acute phase response, acute infection, shock, graft versus host reaction, autoimmune disease or HIV infection in a mammal comprising administering to the mammal in need of such treatment a therapeutically effective amount of a compound of formula (I) or a pharmaceutically acceptable salt form thereof.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^b$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-10}$ alkyl" or "$C_{1-10}$ alkylene" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" or "alkenylene" is intended to include hydrocarbon chains of either a straight or branched configuration and one or more unsaturated carbon-carbon bonds which may occur in any stable point along the chain, such as ethenyl, propenyl, and the like. "Alkynyl" or "alkynylene" is intended to include hydrocarbon chains of either a straight or branched configuration and one or more carbon-carbon triple bonds which may occur in any stable point along the chain, such as ethynyl, propynyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 14-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7-membered monocyclic or bicyclic or 7- to 14-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H, 6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids,such as those disclosed in, for example, Roberts and Vellaccio (1983) *The Peptides*, 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, 9-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated herein in their entirety by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

A series of 2-substituted 2,3,4,5-tetrahydro-1,2,5-benzothiadiazepine 1,1-dioxides of formula 6 are prepared by the method outlined in Scheme 1. Reaction of a D-amino acid 1 with benzenesulfonyl chloride 2 provides sulfonamide 3. N-allylation with allyl bromide and sodium hydride followed by ozonolysis yields aldehyde 5. Reduction of nitro group and intramolecular reductive amination are achieved in one pot with zinc in acetic acid under reflux to provide 6.

An alternative synthesis of the 2-substituted 2,3,4,5-tetrahydro-1,2,5-benzothiadiazepine 1,1-dioxide series of formula 11 is outlined in Scheme 2. Standard coupling of D-amino acid 7 with 2 gives sulfonamide 8. The 2-bromoethyl group is then introduced to the sulfonamide via Mitsunobu coupling with 2-bromoethanol. Iron in acetic acid reduction of 9 gives aniline 10, which cyclizes to give the 2-substituted 2,3,4,5-tetrahydro-1,2,5-benzothiadiazepine 1,1-dioxide upon treatment with N-methylmorpholine.

Scheme 1

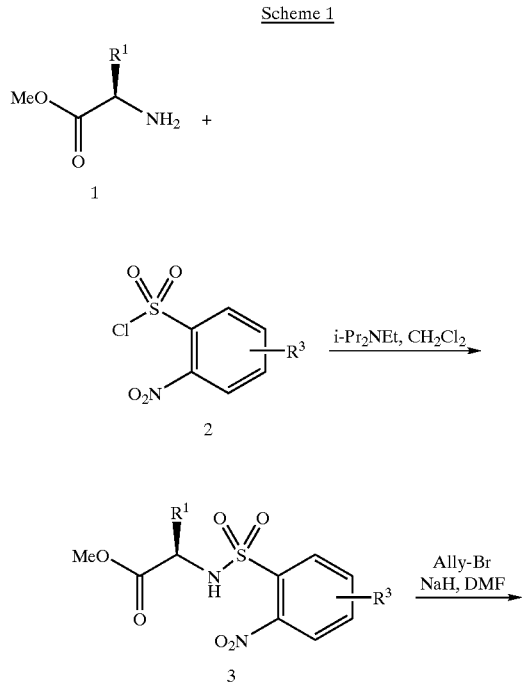

Scheme 2

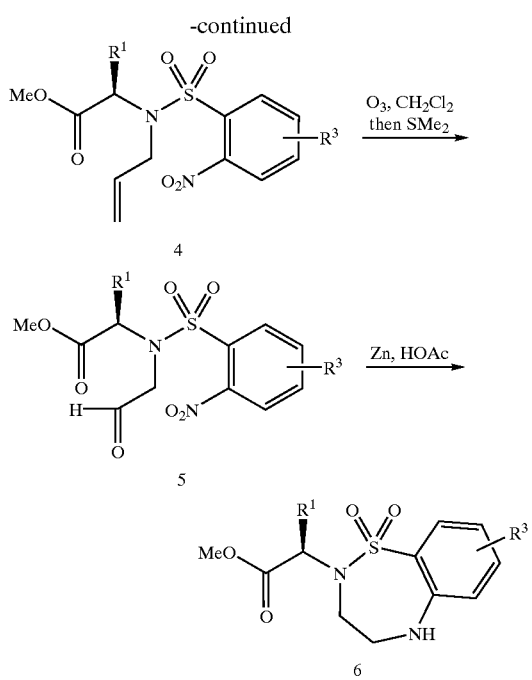

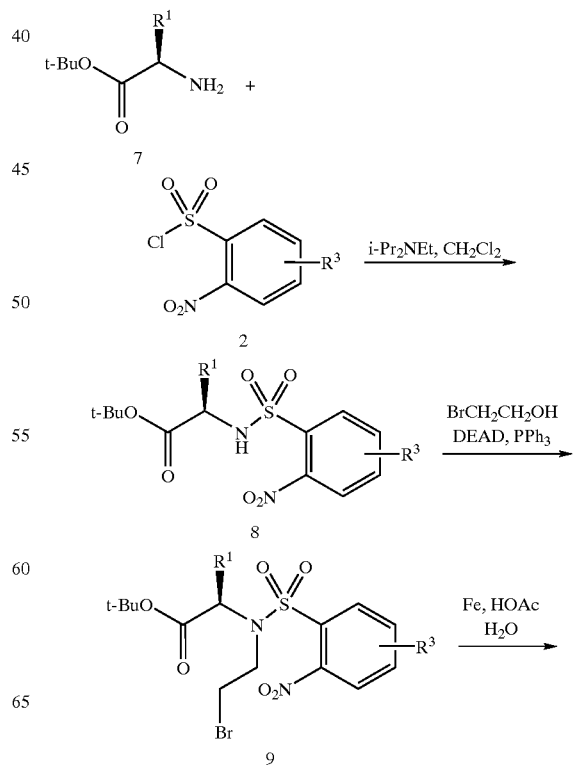

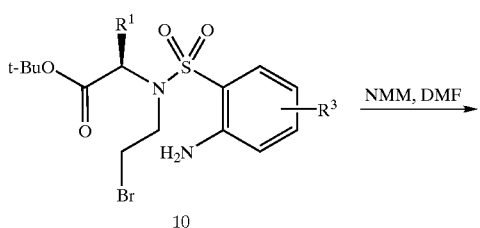

Many of the requisite D-amino acid methyl esters 1 and tert-butyl esters 7 are commercially available or are prepared from commercial material by simple protecting group manipulations. Others are synthesized using Myers method from glycine (Myers, A. G.; Gleason, J. L.; Yoon, T. *J. Am. Chem. Soc.* 1995, 117, 8488), using Mitsunobu conditions from serine (Cherney, R. J.; Wang, L. *J. Org. Chem.* 1996, 61, 2544), or using Evans electrophilic azidations from carboxylic acids (Evans, D. A.; Britton, T. C.; Ellman, J. A.; Dorow, R. L. *J. Am. Chem. Soc.* 1990, 112, 4011).

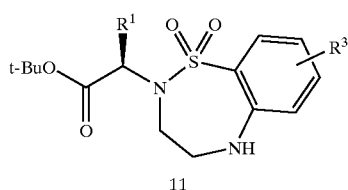

Methyl ester 6 and tert-butyl ester 11 are converted to hydroxamic acid 14 following the route outlined in Scheme 3. Methyl ester hydrolysis with lithium hydroxide and tert-butyl ester hydrolysis with trifluoroacetic acid provide carboxylic acid 12. Coupling with O-benzyl hydroxylamine and reductive removal of benzyl group yield 14. Alternatively, treatment of methyl ester 6 with hydroxylamine and potassium hydroxide in methanol provides hydroxamic acid 14 in a single step.

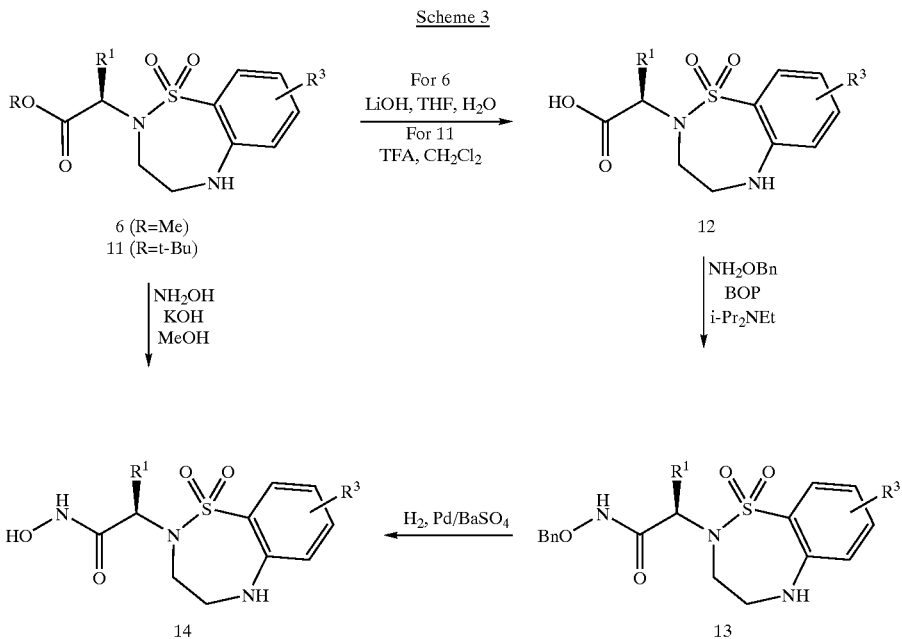

Compounds 6 from Scheme 1 and 11 from Scheme 2 are used as common intermediates for structure diversification. For example, when $R^3$ is an amino group, 11 serves as common starting point for alkylated amine 15, amide 16, sulfonamide 17 and urea 18 (Scheme 4). 15–18 are converted to hydroxamic acids following the sequence outlined in Scheme 3.

Scheme 4

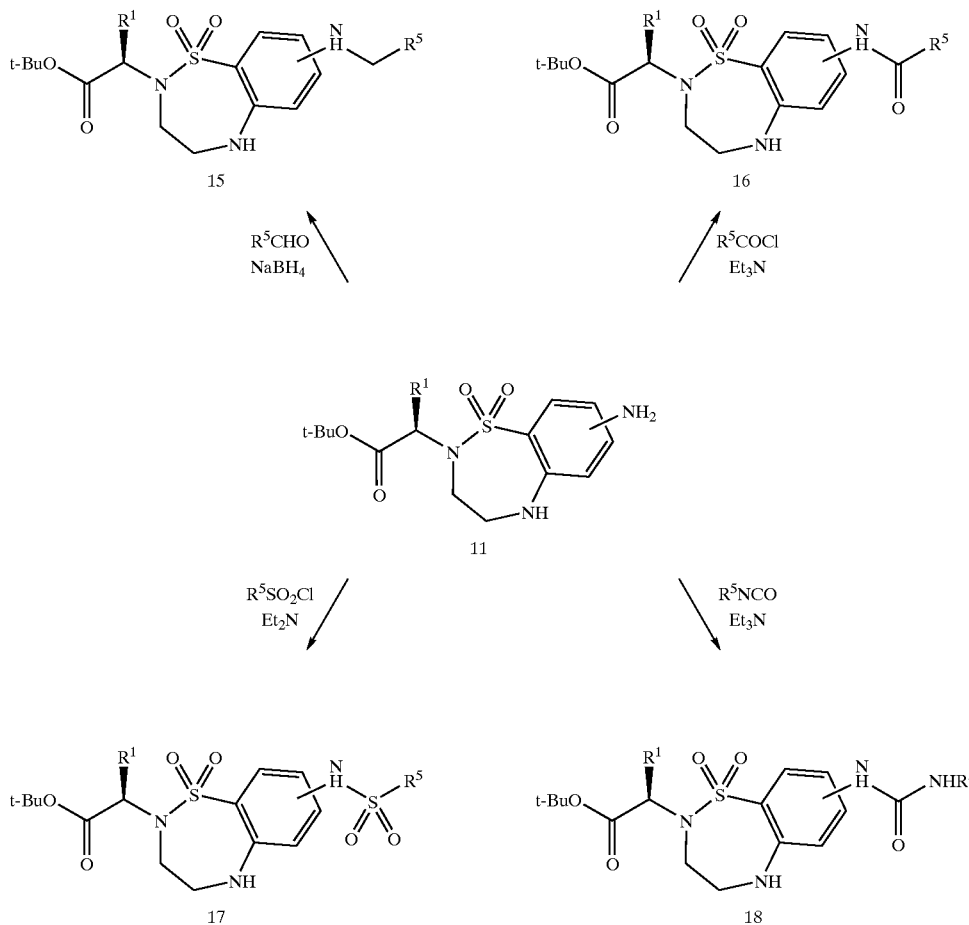

Some of the substituted (2-nitrobenzene)sulfonyl chlorides are commercially available. Others are prepared following known literature procedures. As an illustrated example, Scheme 5 outlines the synthesis of (4-benzyloxy-2-nitrobenzene)sulfonyl chloride (21). Selective protection of the hydroxy group with benzyl bromide and potassium tert-butoxide gives 20. Diazatization of 20 with sodium nitrite and treatment with sulfurous acid and cupric chloride provides the sulfonyl chloride 21.

Scheme 5

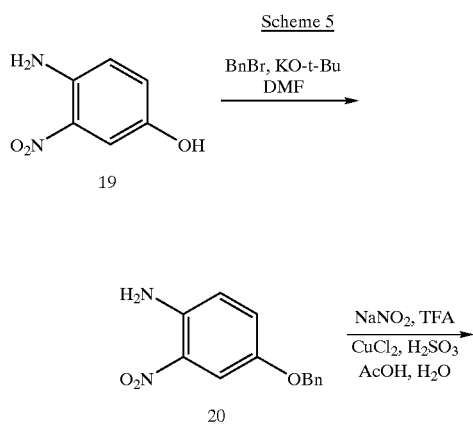

-continued

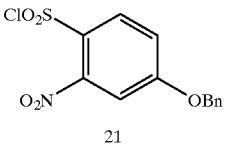

A series of 2-substituted 2,3,4,5-tetrahydro-1,2,5-benzothiadiazepine 1,1-dioxides of formula's 23–26 are prepared by the method outlined in Scheme 6. When $R^3$ is a benzyloxy group, compound 11 prepared from Scheme 2 is converted to phenol 22 by hydrogenolysis. Reaction of 22 with $R^5$—X provides 23, an alternative is the reaction of 22 with $R^5$—OH under Mitsunobu conditions to produce 23. $R^5$ can be appended directly to the aromatic ring by converting 22 to an aryl triflate then reaction with an organometallic in the presence of a palladium (0) catalyst to give 24. 22 can also be reacted with acyl halides or isocyantes to afford 25. Biaryl ethers 26 can be produced by treatment of 22 with aryl boronic acids in the presence of a copper catalyst. 23–26 are then converted to the corresponding hydroxamic acids following the sequence outlined in Scheme 3.

Scheme 6

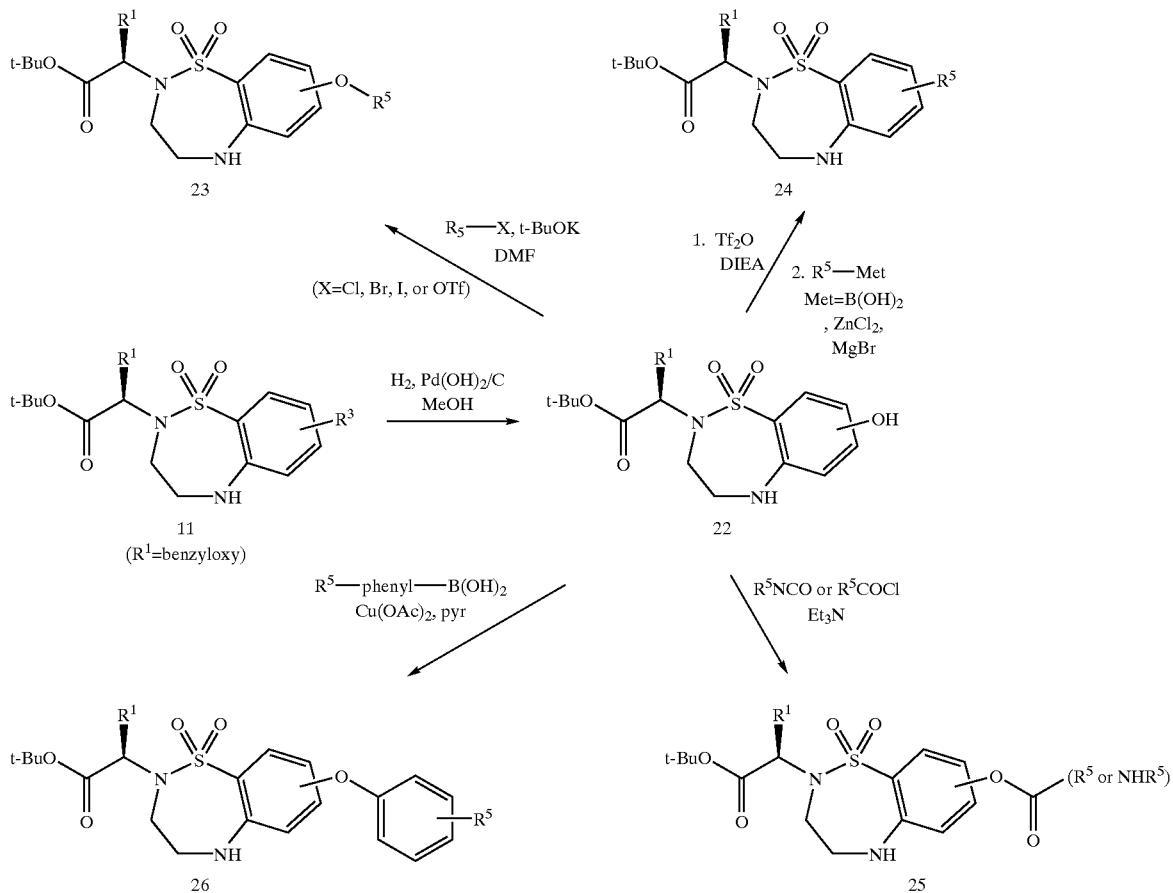

A series of 2,5-disubstituted 2,3,4,5-tetrahydro-1,2,5-benzothiadiazepine 1,1-dioxides of formulas 27–30 are prepared by the method outlined in Scheme 7. Compound 11 is converted to 27 by alkylation, amide 28 by acylation, sulfonamide 29 by sulfonylation, and urea 30 by reaction with isocyanate. 27–30 are then converted to the corresponding hydroxamic acid following the sequence outlined in Scheme 3.

Scheme 7

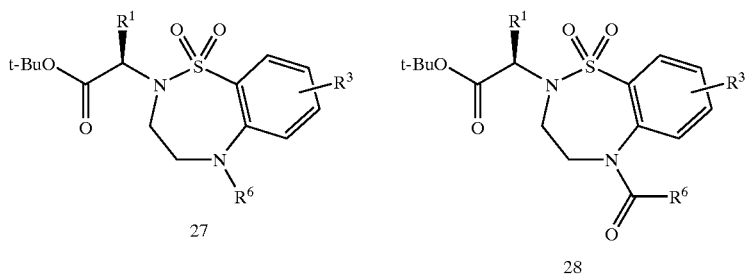

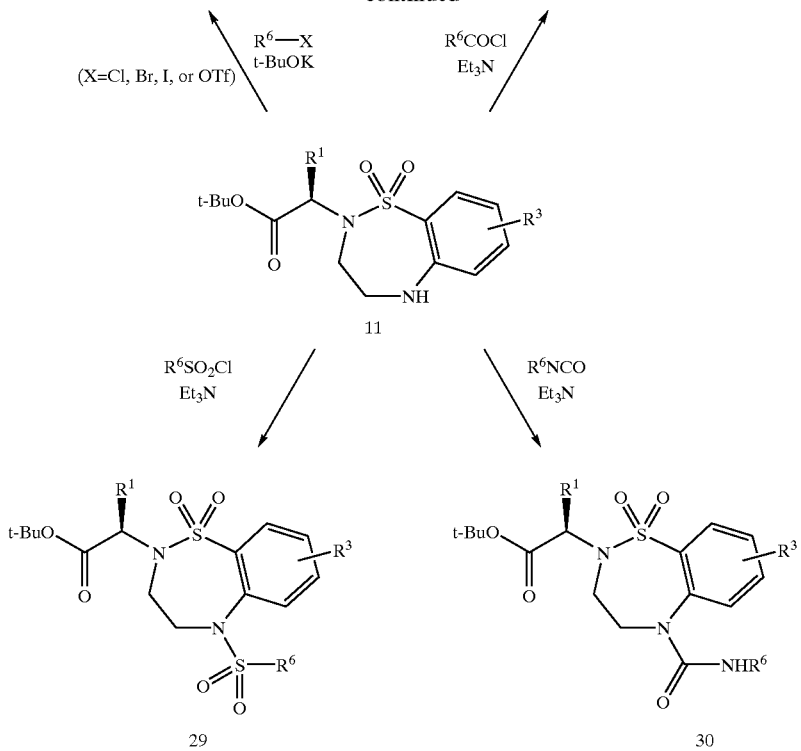

A series of 2-substituted 3,4-dihydro-2H-1,2,4-benzothiadiazine 1,1-dioxides of formula 32 are prepared by the method outlined in Scheme 8. Reduction of 3 gives aniline 31. Treatment of 31 with formaldehyde under acidic conditions provides 32. 32 is then converted to the corresponding hydroxamic acid following the sequence outlined in Scheme 3.

A series of 2-substituted 2,3-dihydro-1,2-benzisothiazole 1,1-dioxides of formula 37 are prepared by the method outlined in Scheme 9. Lithium aluminum hydride reduction of 33 gives benzisothiazole 34. Mitsunobu reaction with hydroxylester 35 or coupling with bromoester 36 under basic conditions provides 37. 37 is then converted to the corresponding hydroxamic acid following the sequence outlined in Scheme 3.

Scheme 8

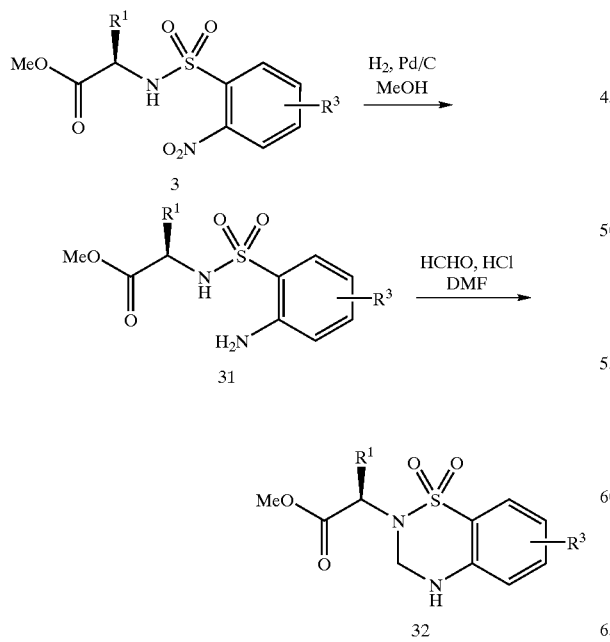

Scheme 9

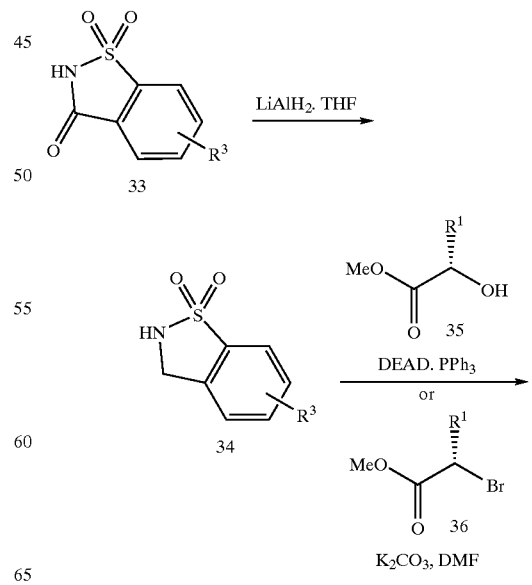

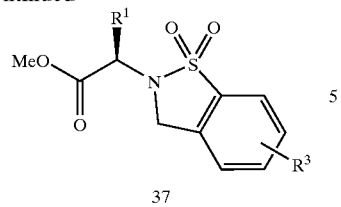

37

A series of 2-substituted 3,4-dihydro-2H-1,2-benzothiazine 1,1-dioxides of formula 44 are prepared by the method outlined in Scheme 10. Following reduction of the nitro group, the resultant aniline is diazatized with sodium nitrite and treated with sulfur dioxide. Hydrolysis of sulfonyl chloride 40 and hydrogenation yield primary amine 42. Benzothiazine formation is accomplished with POCl₃ followed by sodium hydroxide treatment. Mitsunobu reaction with hydroxylester 35 or coupling with bromoester 36 under basic conditions provides 44. 44 is then converted to the corresponding hydroxamic acid following the sequence outlined in Scheme 3.

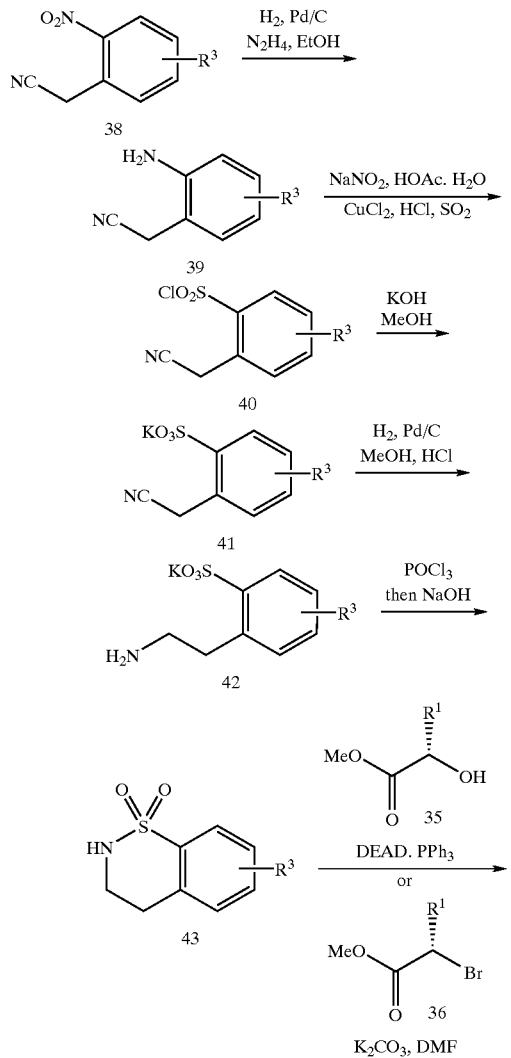

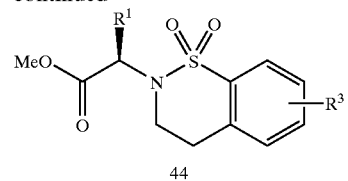

44

Alternatively, the 2-substituted 3,4-dihydro-2H-1,2-benzothiazine 1,1-dioxides of formula 44 are prepared by the method outlined in Scheme 11. Following protection of alcohol 45 with BnBr, lithium bromine exchange and reaction with sulfur dioxide provide the sulfonic acid lithium salt 46. Reaction of 46 with sulfuryl chloride and coupling with amine 1 yield sulfonamide 48. Cleavage of benzyl ether and intramolecular Mitsunobu reaction give 44. 44 is then converted to the corresponding hydroxamic acid following the sequence outlined in Scheme 3.

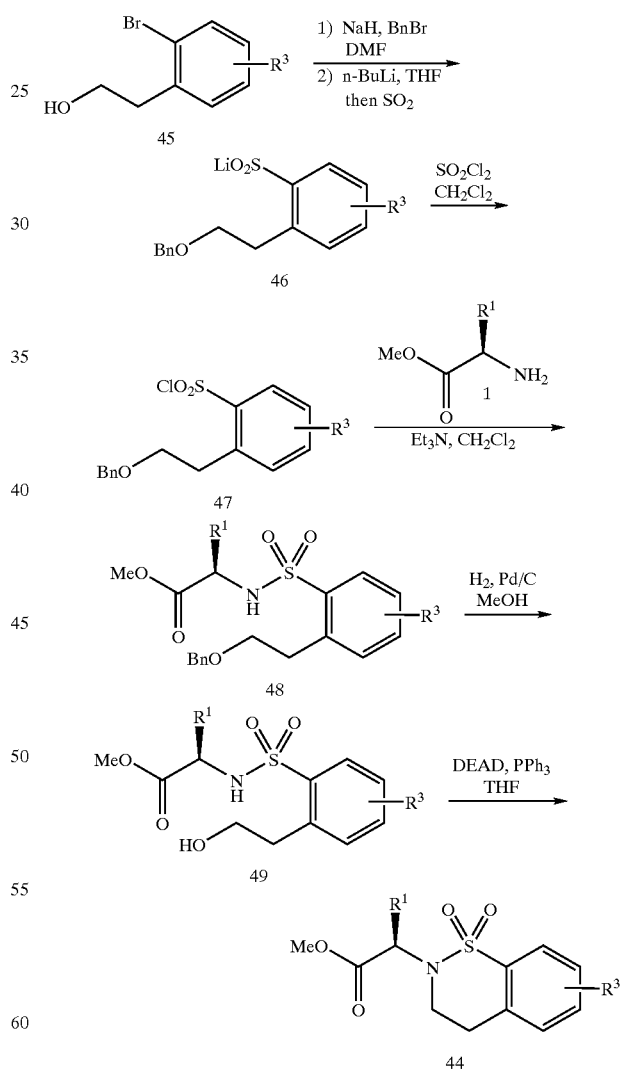

A series of 2-substituted 2,3,4,5-tetrahydro-1,2-benzothiazepine 1,1-dioxides of formula 56 are prepared by the method outlined in Scheme 12. Reaction of amine 7 with sulfonyl chloride 50 yields sulfonamide 51. Heck coupling with methyl acrylate gives 52. 52 is then converted to alcohol 55 by olefin reduction, methyl ester hydrolysis, and hydroboration of the resultant carboxylic acid. The formation of benzothiazepine 56 is accomplished by intramolecular Mitsunobu reaction on 55. 56 is then converted to the corresponding hydroxamic acid following the sequence outlined in Scheme 3.

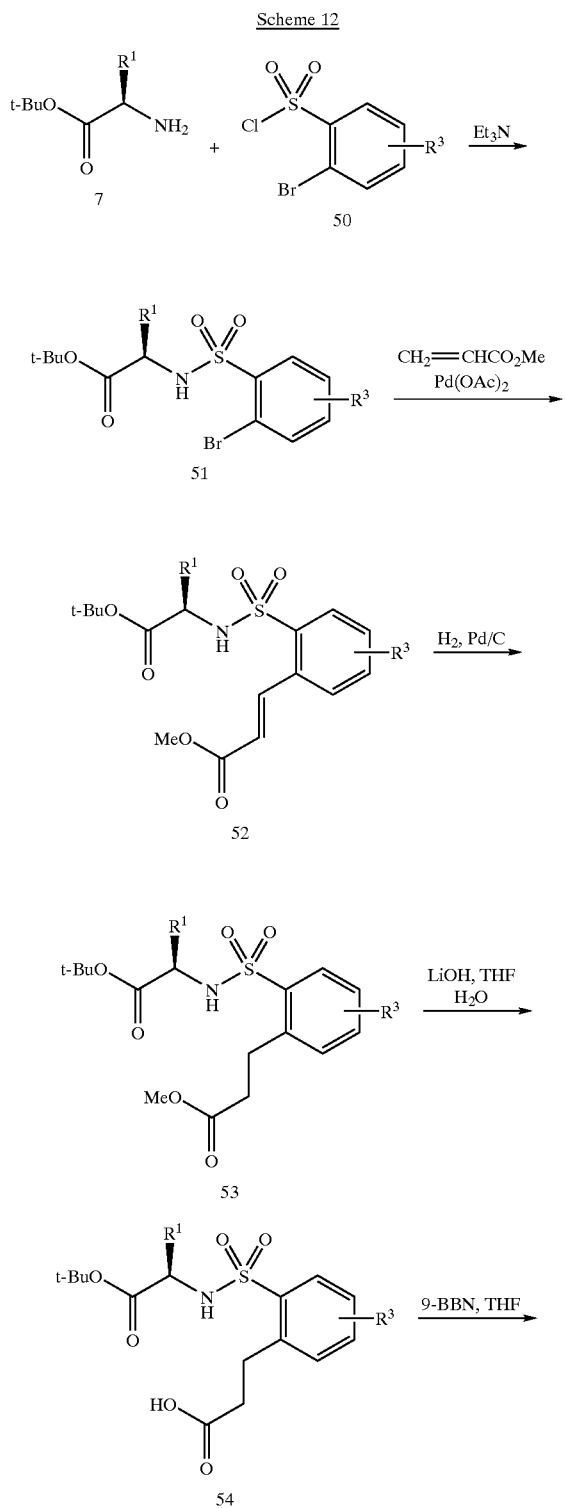

A series of 2-substituted 3,4-dihydro-2H-5,1,2-benzoxathiazepine 1,1-dioxides of formula 61 are prepared by the method outlined in Scheme 13. Coupling of amine 1 with sulfonyl chloride 57 gives sulfonamide 58. Mitsunobu reaction with 2-bromoethanol provides 59. Cleavage of benzyl ether and treatment with base such as cesium carbonate yield benzoxathiazepine 61. 61 is then converted to the corresponding hydroxamic acid following the sequence outlined in Scheme 3.

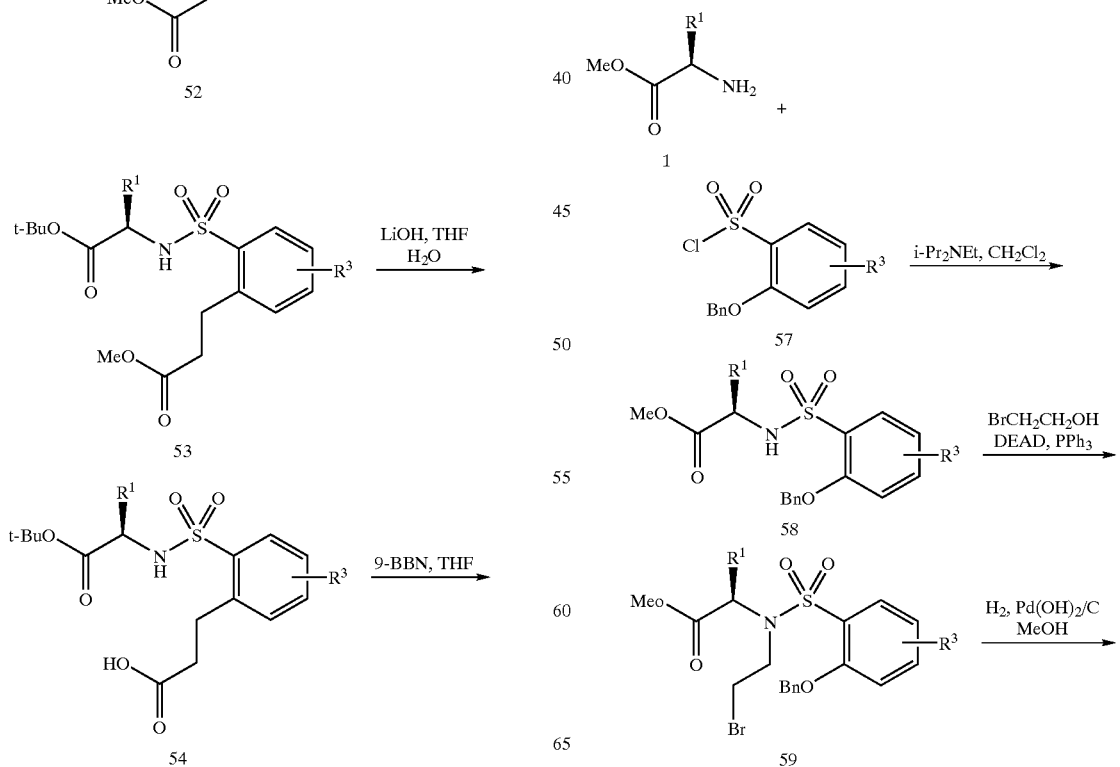

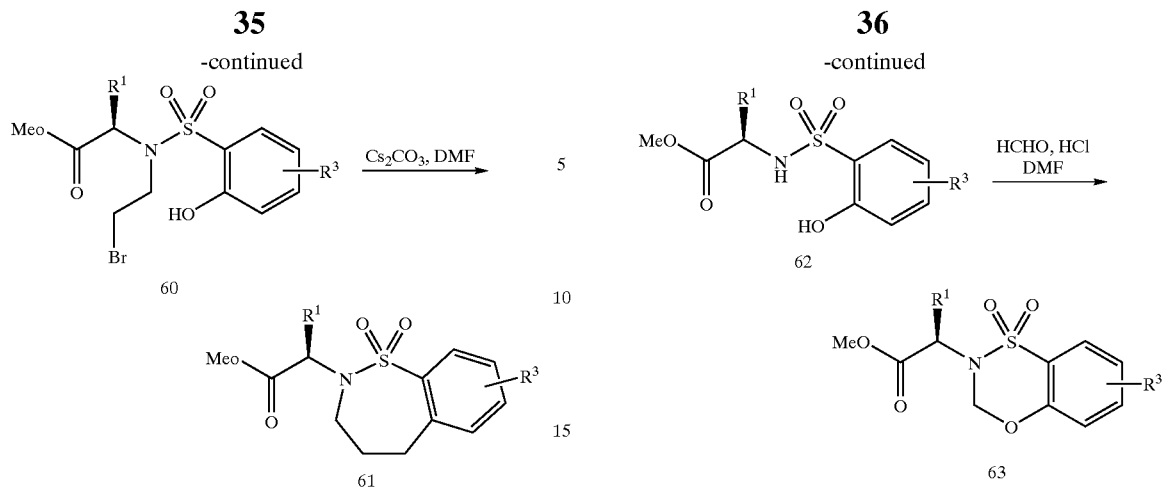

A series of 2-substituted 3,4-dihydro-2H-4,1,2-benzoxathiazepine 1,1-dioxides of formula 63 are prepared by the method outlined in Scheme 14. Employing 58 as common intermediate, cleavage of benzyl ether and reaction with formaldehyde under acidic conditions yield benzoxathiazepine 63. 63 is then converted to the corresponding hydroxamic acid following the sequence outlined in Scheme 3.

Scheme 14

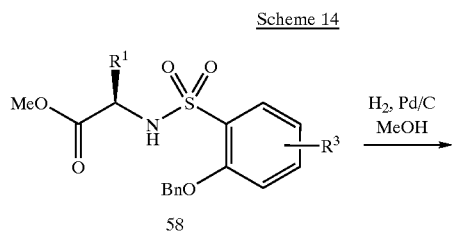

A series of 2,4-substituted 2,3,4,5-tetrahydro-1,2,5-benzothiadiazepine 1,1-dioxides of formula 67–70 are prepared by the method outlined in Scheme 15. The sequence is started with compound 8 from Scheme 2. The Mitsunobu reaction is performed with glycolaldehyde diethyl acetal to yield 64. Reduction is accomplished as before with iron to give 65. The cyclization is performed with pTsOH in warm DMF. The resulting compound 66 is a very versatile intermediate. A Grignard is added to 66 to give 67, which is converted to the hydroxamate as in Scheme 3. A nitrile is added to compound 66 through the use of TMSCN to afford 68. This is reduced to 69 and then substituted to 70. Compounds 68, 69 and 70 are converted to their respective hydroxamates via Scheme 3.

Scheme 15

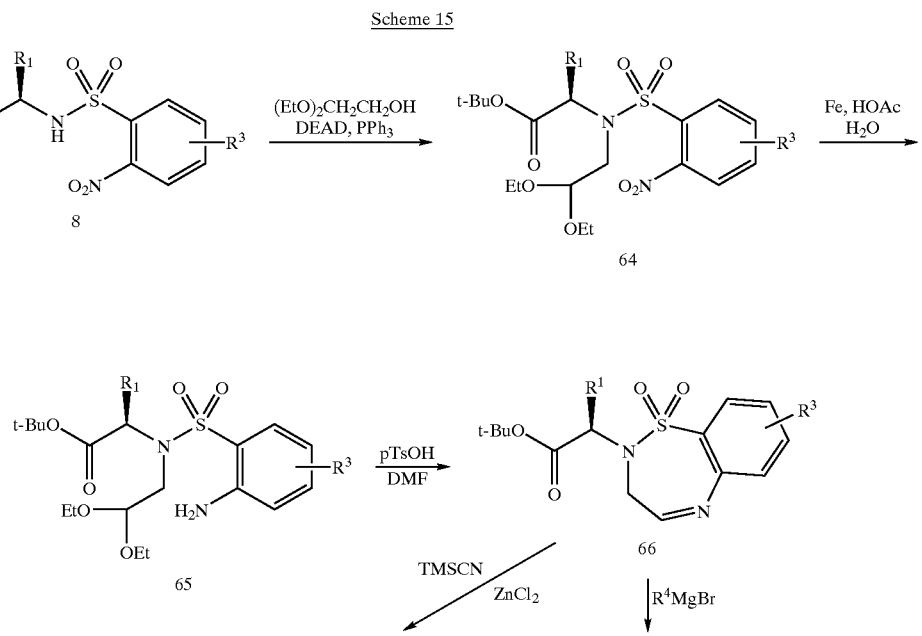

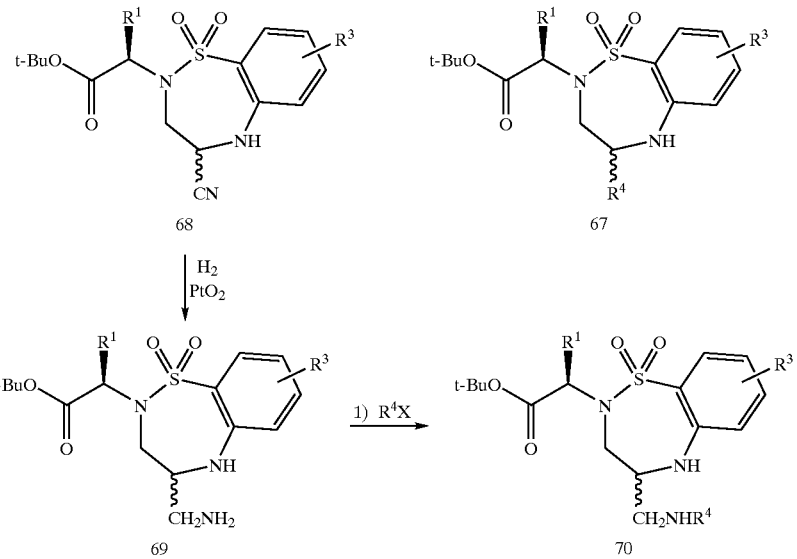

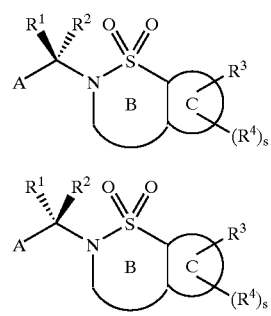

One diastereomer of a compound of Formula I may display superior activity compared with the others. Thus, the following stereochemistries are considered to be a part of the present invention.

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g., Andrew S. Thompson, et al, *Tet. lett.* 1995, 36, 8937–8940).

Other features of the invention will become apparent in the course of the following descriptions of exemplary embodiments which are given for illustration of the invention and are not intended to be limiting thereof.

EXAMPLES

Abbreviations used in the Examples are defined as follows: "1×" for once, "2×" for twice, "3×" for thrice, "°C." for degrees Celsius, "eq" for equivalent or equivalents, "g" for gram or grams, "mg" for milligram or milligrams, "mL" for milliliter or milliliters, "$^1$H" for proton, "h" for hour or hours, "M" for molar, "min" for minute or minutes, "MHz" for megahertz, "MS" for mass spectroscopy, "NMR" for nuclear magnetic resonance spectroscopy, "rt" for room temperature, "tlc" for thin layer chromatography, "v/v" for volume to volume ratio. "α", "β", "R" and "S" are stereochemical designations familiar to those skilled in the art.

Example 1

4,5-dihydro-N-hydroxy-1,2,5-benzothiadiazepine-2 (3H)-acetamide-1,1-dioxide (1a) 2-Nitrobenzenesulfonyl chloride (5.00 g, 22.6 mmol) was added to a solution of aminoacetaldehyde dimethyl acetal (2.61 g, 1.1 eq) and N,N-diisopropylethylamine (11.66 g, 2 eq) in dichloromethane (100 mL) at −78 °C. The cold bath was removed and the mixture was stirred at ambient temperature for 45 min. Following addition of ethyl acetate (600 mL), the mixture was extracted with 5% aqueous sodium bicarbonate (2×100 mL), brine (100 mL), dried (MgSO$_4$) and concentrated to give the desired sulfonamide (6.13 g, 93%). MS found: (M+NH$_4$)$^+$=308.

(1b) Sodium hydride (1.377 g, 2 eq, 60% in mineral oil) was added in several portions to a solution of the sulfonamide (5.00 g, 17.2 mmol) from reaction (1a) and methyl bromoacetate (7.90 g, 3 eq) in N,N-dimethylformamide (100 mL) at rt. After 20 min at this temperature, a pH7 buffer (200 mL) was added and the mixture was extracted with ethyl acetate (3×200 mL). The combined extracts were washed with pH7 buffer (50 mL), water (50 mL), brine (50 mL), dried (Na$_2$SO$_4$) and concentrated. Silica gel column chromatography (ethyl acetate-hexane, 40:60 then 50:50) yielded the desired product (4.93 g, 87%). MS found: (M+H)+=331.

(1c) Zinc powder (21.6 g, 25 eq) was added in several portions to a solution of the sulfonamide (4.80 g, 13.3 mmol) from reaction (1b) in acetic acid (200 mL) at rt. After 3 h at reflux, the mixture was cooled to rt, treated with 1:1 mixture of ethanol-chloroform (250 mL) and filtered. The filter cake was washed with 1:1 mixture of ethanol-chloroform until free of product. The filtrate was concentrated and purified by silica gel column chromatography (ethyl acetate-hexane, 50:50 then 60:40) to give the desired product (1.30 g, 36%). MS found: (M+Na)$^+$= 293.

(1d) Preparation of hydroxylamine/potassium hydroxide solution: A solution of potassium hydroxide (2.81 g, 1.5 eq) in methanol (7 mL) was added to a hot solution of hydroxylamine hydrochloride (2.34 g, 33.7 mmol) in methanol (12 mL). After the mixture was cooled to room temperature, the precipitate was removed by filtration. The filtrate was used fresh and assumed hydroxylamine concentration of 1.76 M.

The freshly prepared 1.76 M solution of hydroxylamine (2.1 mL, 4 eq) was added to the ester (369.2 mg, 1.00 mmol) from reaction (1c) in methanol (3 mL) at rt. After 2 h at this temperature, the solution was acidified to pH 4–5 with 1 N HCl. Following removal of methanol in vacuo, the residue was extracted with ethyl acetate (3×20 mL). The combined extracts were washed with brine, dried (MgSO$_4$) and concentrated. The residue was treated with ethyl acetate (10 mL) and heated gently to dissolve the desired product. Removal of solid by filtration and concentration of filtrate gave the desired hydroxamic acid (119 mg, 47%). MS found: $(M-O+H)^+=256$.

Example 2

4,5-dihydro-N-hydroxy-7-methoxy-1,2,5-benzothiadiazepine-2(3H)-acetamide-1,1-dioxide (2a) Following a procedure analogous to that used in step (1a), 4-methoxy-2-nitrobenzenesulfonyl chloride (5.00 g, 19.9 mmol) was reacted with aminoacetaldehyde dimethyl acetal to give the desired sulfonamide (6.12 g, 95%). MS found: $(M+NH_4)^+=338$.

(2b) Following a procedure analogous to that used in step (1b), the sulfonamide (5.20 g, 16.2 mmol) from reaction (2a) was alkylated with methyl bromoacetate. Silica gel column chromatography (ethyl acetate-hexane, 40:60 then 50:50) yielded the desired product (6.28 g, 99%). MS found: $(M+Na)^+=415$.

(2c) Following a procedure analogous to that used in step (1c), the sulfonamide (6.00 g, 15.3 mmol) from reaction (2b) was treated with zinc in acetic acid. Silica gel column chromatography (ethyl acetate-hexane, 55:45 then 70:30 then 100:0) yielded the desired product (2.14 g, 47%). MS found: $(M+H)^+=301$.

(2d) Following a procedure analogous to that used in step (1d), the methyl ester (371.8 mg, 1.24 mmol) was treated with hydroxylamine to give the desired hydroxamic acid (300 mg, 80%). MS found: $(M-H)^-=300$.

Example 3

(R)-4,5-dihydro-N-hydroxy-alpha-methyl-1,2,5-benzothiadiazepine-2(3H)-acetamide-1,1-dioxide (3a) Following a procedure analogous to that used in step (1a), 2-nitrobenzenesulfonyl chloride (3.96 g, 17.9 mmol) was reacted with D-alanine methyl ester hydrochloride (2.50 g, 1 eq). Silica gel column chromatography (ethyl acetate-hexane, 40:60) yielded the desired product (4.35 g, 84%). MS found: $(M+NH_4)^+=306$.

(3b) Following a procedure analogous to that used in step (1b), the sulfonamide (4.54 g, 14.3 mmol) from reaction (3a) was alkylated with allyl bromide. Silica gel column chromatography (ethyl acetate-hexane, 25:75) yielded the desired product (3.42 g, 71%). MS found: $(M+NH_4)^+=346$.

(3c) Ozone was bubbled through a solution of the olefin (3.32 g, 10.1 mmol) from reaction (3b) in dichloromethane (250 mL) at −78 °C. until blue color persisted. The mixture was then purged with nitrogen, treated with methyl sulfide (3.70 mL, 5 eq) and stirred at rt overnight. Removal of solvent gave the crude aldehyde. This material was used in reaction (3d) without purification.

(3d) Following a procedure analogous to that used in step (1c), the crude aldehyde from reaction (3c) was reacted with zinc in acetic acid. Silica gel column chromatography (ethyl acetate-hexane, 35:65 then 40:60) gave the desired product (0.426 g, 15% for two steps). MS found: $(M+H)^+=285$.

(3e) Following a procedure analogous to that used in step (1d), the ester (330 mg, 1.16 mmol) from reaction (3d) was reacted with hydroxylamine. Preparative thin layer chromatography (methanol-dichloromethane, 10:90) gave the desired hydroxamic acid (0.231 g, 70%). MS found: $(M-H)^-=284$.

Example 4

(R)-4,5-dihydro-N-hydroxy-7-methoxy-alpha-methyl-1,2,5-benzothiadiazepine-2(3H)-acetamide-1,1-dioxide (4a) Following a procedure analogous to that used in step (1a), 4-methoxy-2-nitrobenzenesulfonyl chloride (3.78 g, 15.0 mmol) was reacted with D-alanine methyl ester hydrochloride (2.10 g, 1 eq) to give the desired product (4.66 g, 97%). MS found: $(M+NH_4)^+=336$.

(4b) Following a procedure analogous to that used in step (1b), the sulfonamide (4.54 g, 14.3 mmol) from reaction (4a) was alkylated with allyl bromide. Silica gel column chromatography (ethyl acetate-hexane, 30:70 then 40:60) yielded the desired product (2.85 g, 56%). MS found: $(M+Na)^+=381$.

(4c) Following a procedure analogous to that used in step (3c), the olefin (2.70 g, 7.53 mmol) from reaction (4b) was cleaved by ozonolysis. The crude material from the reaction was used in reaction (4d) without purification.

(4d) Following a procedure analogous to that used in step (1c), the crude aldehyde from reaction (4c) was reacted with zinc in acetic acid. Silica gel column chromatography (ethyl acetate-hexane, 40:60 then 50:50) gave the desired product (0.350 g, 18% for two steps). MS found: $(M+H)^+=315$.

(4e) Following a procedure analogous to that used in step (1d), the ester (368 mg, 1.17 mmol) from reaction (4d) was reacted with hydroxylamine. Preparative thin layer chromatography (methanol-dichloromethane, 7.5:92.5) gave the desired hydroxamic acid (0.90 g, 24%). MS found: $(M-H)^-=314$.

Example 5

(R)-4,5-dihydro-N-hydroxy-7-methoxy-alpha-(1-methylethyl)-1,2,5-benzothiadiazepine-2(3H)-acetamide-1,1-dioxide (5a) Following a procedure analogous to that used in step (1a), 4-methoxy-2-nitrobenzenesulfonyl chloride (4.16 g, 16.5 mmol) was reacted with D-valine ethyl ester hydrochloride (3.00 g, 1 eq). Silica gel column chromatography (ethyl acetate-hexane, 25:75) gave the desired product (4.69 g, 79%). MS found: $(M+NH_4)^+=378$.

(5b) Following a procedure analogous to that used in step (1b), the sulfonamide (4.61 g, 12.8 mmol) from reaction (5a) was alkylated with allyl bromide. Silica gel column chromatography (ethyl acetate-hexane, 25:75) yielded the desired product (2.18 g, 82%). MS found: $(M+H)^-=401$.

(5c) Following a procedure analogous to that used in step (3c), the olefin (4.02 g, 10.1 mmol) from reaction (5b) was cleaved by ozonolysis to give the crude aldehyde (4.63 g). This material was used in reaction (5d) without purification.

(5d) Following a procedure analogous to that used in step (1c), the crude aldehyde (4.50 g) from reaction (5c) was reacted with zinc in acetic acid. Silica gel column chromatography (ethyl acetate-hexane, 30:70 then 40:60) gave the desired product (0.440 g, 13% for two steps). MS found: $(M+H)^+=357$.

(5e) Following a procedure analogous to that used in step (1d), the ester (340 mg, 0.95 mmol) from reaction (5d) was reacted with hydroxylamine at rt for 20 h and at 70–80 °C. for 4 h. Preparative thin layer chromatography (methanol-dichloromethane, 7.5:92.5) gave the desired hydroxamic acid (0.42 g, 13%). MS found: $(M-H)^-=342$.

Example 6

N-hydroxy-2(R)-[7-(3,5-dimethylbenzyloxy)-2,3,4,5-tetrahydrobenzo[1,2,5-f]thiadiazepine-1,1-dioxide]-propanamide A. 4-Benzyloxy-2-nitroaniline 4-Amino-3-nitrophenol (25 g, 162.2 mmol) was dissolved in DMF and cooled to 0° C. 1M potassium tert-butoxide (162.2 mL) was added dropwise over 20 min. After stirring 30 min at 0° C., benzyl bromide (19.8 mL, 162.2 mmol) in DMF was added dropwise. After 30 min at 0° C., the reaction was quenched with $NH_4Cl$ solution. 4-benzyloxy-2-nitroaniline (32 g, 131 mmol) was isolated by filtration. $MS(CI, NH_3)$ m/e 245 $(M+1)^+$.

B. 4-Benzyloxy-2-nitrobenzenesulfonyl Chloride

4-Benzyloxy-2-nitroaniline (1.5 g, 6.14 mmol) was dissolved in TFA (20 mL) and concentrated HCl (2 mL). After cooling to 0° C., $NaNO_2$ (529.6 mg, 7.7 mmol) in $H_2O$ was added dropwise over 30 min. Once the addition was complete the reaction was stirred an additional 5 min. The resulting solution was poured into AcOH (20 mL), $H_2SO_3$ (20 mL), and $CuCl_2$ (412.8 mg, 3.07 mmol) containing a catalytic amount of CuCl (ca. 25 mg) at 0 °C. After 35 min at room temperature, the solid material was filtered off and washed with water. This provided 4-benzyloxy-2-nitrobenzenesulfonyl chloride (1.5 g, 6.14 mmol). MS (ES-neg) m/e 307.8 $(M-Cl+OH-1)^+$.

C. N-(4-benzyloxy-2-nitrobenzenesulfonyl)-D-Alanine Methyl Ester

D-Ala-Me.HCl (5.7 g, 40.8 mmol) was dissolved in $CH_2Cl_2$ diisopropylethyl amine (14.8 mL, 85.1 mmol). At 0° C., 4-benzyloxy-2-nitrobenzenesulfonyl chloride (11.1 g, 34.0 mmol) was added dropwise in $CH_2Cl_2$. After stirring overnight, the solution was washed with 1N HCl. The $CH_2Cl_2$ was dried, filtered and concentrated. Flash chromatography of the resulting residue gave the sulfonamide (10.6 g, 26.9 mmol): MS(ES-pos) m/e 416.9 $(M+Na)^+$.

D. N-(4-benzyloxy-2-nitrobenzenesulfonyl)-N-(bromoethylene)-D-Alanine Methyl Ester The sulfonamide (10.6 g, 26.9 mmol) was dissolved in THF prior to the addition of triphenylphosphine (14.1 g, 53.8 mmol) and 2-bromoethanol (3.8 mL, 53.8 mmol). At room temperature, diethyl azodicarboxylate (8.5 mL, 53.8 mmol) was added dropwise and the reaction was stirred overnight. The THF was removed and flash chromatography of the resulting residue gave the alkylated sulfonamide (11.5 g, 22.9 mmol): MS(ES-pos) m/e 522.8 $(M+Na)^+$.

D. N-(4-benzyloxy-2-aminobenzenesulfonyl)-N-(bromoethylene)-D-Alanine Methyl Ester The nitro sulfonamide (11.5 g, 22.9 mmol) was dissolved in glacial AcOH and $H_2O$ prior to the addition of Fe dust (12.8 g). This solution was heated at 60° C. for 1 hr. After cooling to rt, the Fe was filtered off and the AcOH was removed. The resulting residue was dissolved in EtOAc and washed with sat. $NaHCO_3$ solution. The EtOAc was dried, filtered and concentrated to give the crude aniline (8.9 g, 8.9 mmol), which was directly used in the next procedure: MS(ES-neg) m/e 470.8 $(M-1)^+$.

E. Methyl-2(R)-[7-benzyloxy-2,3,4,5-tetrahydrobenzo[1,2,5-f]thiadiazepine-1,1-dioxide]-propanoate The crude aniline (7.1 g, 15.1 mmol) was dissolved in DMF and N-methylmorpholine (5.1 mL, 47.1 mmol) was added. This mixture was heated at 80° C. for 5 hr. After cooling, the DMF was removed and EtOAc was added. The EtOAc was washed with brine, dried, and concentrated. Flash chromatography of the resulting residue gave the cyclized product (4.4 g, 11.3 mmol): MS(ES-pos) m/e 413.0 $(M+Na)^+$.

F. Methyl-2(R)-[7-hydroxy-2,3,4,5-tetrahydrobenzo[1,2,5-f]thiadiazepine-1,1-dioxide]-propanoate The benzyl phenol (2.4 g, 6.1 mmol) was dissolved in MeOH and 10% Pd/C(240 mg) was added. This mixture was hydrogenated at 50 psi on a Parr for 4 hr. The Pd/C was removed and the MeOH was concentrated to give the phenol (2.0 g, 5.6 mmol): MS(ES-neg) m/e 299.7 $(M-H)^+$.

G. Methyl-2(R)-[7-(3,5-dimethylbenzyloxy)-2,3,4,5-tetrahydrobenzo[1,2,5-f]thiadiazepine-1,1-dioxide]-propanoate The phenol (100 mg, 0.33 mmol) was dissolved in DMF and cooled to 0° C. At 0° C., 1M KOtBu (0.36 mL, 0.36 mmol) in tBuOH was added dropwise. After 20 min, 3,5-dimethylbenzyl bromide (66.3 mg, 0.33 mmol) was added and the reaction warmed to rt. After 15 hr, the reaction was quenched with saturated $NH_4Cl$ solution and EtOAc was added. The EtOAc was washed with brine, dried, and concentrated. Flash chromatography of the resulting residue afforded the alkylated phenol (85 mg, 0.20 mmol): MS(ES-pos) m/e 418.9 $(M+H)^+$.

H. N-hydroxy-2(R)-[7-(3,5-dimethylbenzyloxy)-2,3,4,5-tetrahydrobenzo[1,2,5-f]thiadiazepine-1,1-dioxide]-propanamide To a solution of 25% NaOMe in MeOH (0.62 mL) was added $NH_2OH.HCl$ (133 mg) in MeOH. After cooling to 0° C., the methyl ester (80 mg, 0.19 mmol) in MeOH was added. This mixture was stirred overnight. The reaction was concentrated and partitioned between EtOAc and water. The EtOAc was dried and concentrated. The resulting residue was recrystallized from benzene to give the hydroxamate (30 mg, 0.07 mmol): MS(ES-neg) m/e 417.8 $(M-H)^-$.

Example 7

N-hydroxy-2(R)-[7-(3,5-dichlorobenzyloxy)-2,3,4,5-tetrahydrobenzo[1,2,5-f]thiadiazepine-1,1-dioxide]-propanamide This was produced analogously to example 6 through the use of 3,5-dichlorobenzyl chloride in step G: MS(ES-neg) m/e 457.6 $(M-H)^-$.

Example 8

N-hydroxy-2(R)-[7-(3,5-dimethoxybenzyloxy)-2,3,4,5-tetrahydrobenzo[1,2,5-f]thiadiazepine-1,1-dioxide]-propanamide This was produced analogously to example 6 through the use of 3,5-dimethoxybenzyl chloride in step G: MS(ES-neg) m/e 449.7 (M−H)⁻.

Example 9

N-hydroxy-2(R)-[7-(3,5-dibromobenzyloxy)-2,3,4,5-tetrahydrobenzo[1,2,5-f]thiadiazepine-1,1-dioxide]-propanamide This was produced analogously to example 6 through the use of 3,5-dibromobenzyl bromide in step G: MS(ES-neg) m/e 550.0 (M−H)⁻.

Example 10

N-hydroxy-2(R)-[7-(3,5-diethoxybenzyloxy)-2,3,4,5-tetrahydrobenzo[1,2,5-f]thiadiazepine-1,1-dioxide]-propanamide This was produced analogously to example 6 through the use of 3,5-diethoxybenzyl bromide in step G: MS(ES-pos) m/e 480.1 (M−H)⁻.

Example 11

N-hydroxy-2(R)-[7-(2,6-dichloropyridyl-4-methyleneoxy)-2,3,4,5-tetrahydrobenzo[1,2,5-f]thiadiazepine-1,1-dioxide]-propanamide This was produced analogously to example 6 through the use of 4-(bromomethyl)-2,6-dichloropyridine in step G: MS(ES-neg) m/e 458.8 (M−H)⁻.

Example 12

N-hydroxy-2(R)-[7-(3-amino-5-methylbenzyloxy)-2,3,4,5-tetrahydrobenzo[1,2,5-f]thiadiazepine-1,1-dioxide]-propanamide This was produced analogously to example 6 through the use of 3-methyl-5-nitro-benzylbromide in step G followed by a second Fe/AcOH reduction as in step D: MS(ES-neg) m/e 418.9 (M−H)⁻.

Example 13

N-hydroxy-2(R)-[7-(3,5-dimethylbenzyloxy)-2,3,4,5-tetrahydrobenzo[1,2 5-f]thiadiazepine-1,1-dioxide]-3-methylbutanamide A. Tert-butyl-2(R)-[7-(3,5-dimethylbenzyloxy)-2,3,4,5-tetrahydrobenzo[1,2,5-f]thiadiazepine-1,1-dioxide]-3-methylbutanoate This was produced analogously to example 6 using steps A–G with D-valine-tert-butyl ester and 3,5-dimethylbenzyl bromide: MS(ES-pos) m/e 489.4 (M+H)⁺.

B. N-hydroxy-2(R)-[7-(3,5-dimethylbenzyloxy)-2,3,4,5-tetrahydrobenzo[1,2,5-f]thiadiazepine-1,1-dioxide]-3-methylbutanamide The tert-butyl ester from above (287 mg, 0.58 mmol) was dissolved in CH₂Cl₂ (3 mL) and TFA (15 mL) was added. After stirring for 2 hr, the solution was concentrated to the crude acid. The crude acid was dissolved in DMF and N-methylmorpholine (0.26 mL, 2.4 mmol) was added. The mixture was cooled to 0° C. and BOP (294 mg, 0.66 mmol) was added. After 20 min at 0° C., HONH₂·HCl (82 mg, 1.2 mmol) was added. The reaction was stirred overnight before the solvent was removed. EtOAc and saturated NH₄Cl solution were added to the residue. The EtOAc was dried and concentrated. Flash chromatography provided the hydroxamate (55 mg, 0.12 mmol): MS(ES-neg) m/e 446.0 (M−H)⁻.

Example 14

N-hydroxy-2(R)-[7-(3,5-dimethoxybenzyloxy)-2,3,4,5-tetrahydrobenzo[1,2,5-f]thiadiazepine-1,1-dioxide]-3-methylbutanamide This was produced analogously to example 13 through the use of 3,5-dimethoxybenzyl chloride: MS(ES-neg) m/e 478.0 (M−H)⁻.

Example 15

N-hydroxy-2(R)-[7-(3,5-diethoxybenzyloxy)-2,3,4,5-tetrahydrobenzo[1,2,5-f]thiadiazepine-1,1-dioxide]-3-methylbutanamide This was produced analogously to example 6 through the use of 3,5-diethoxybenzyl bromide in step G: MS(ES-neg) m/e 505.8 (M−H)⁻.

Example 16

N-hydroxy-2(R)-[7-(4,5-dimethylthiazolyl-2-methyleneoxy)-2,3,4,5-tetrahydrobenzo[1,2,5-f]thiadiazepine-1,1-dioxide]-3-methylbutanamide This was produced analogously to example 6 through the use of 2-(bromomethyl)-4,5-dimethylthiazole in step G: MS(ES-neg) m/e 505.8 (M−H)⁻.

Example 17

N-hydroxy-2(R)-[7-(3,5-dimethylbenzyloxy)-2,3,4,5-tetrahydrobenzo[1,2,5-f]thiadiazepine-1,1-dioxide]-4-methylpentanamide This was produced analogously to example 13 through the use of D-leucine-tert-butyl ester and 3,5-dimethylbenzyl bromide: MS(ES-neg) m/e 460.2 (M−H)⁻.

Example 18

N-hydroxy-2(R)-[7-(3,5-dibromobenzyloxy)-2,3,4,5-tetrahydrobenzo[1,2,5-f]thiadiazepine-1,1-dioxide]-4-methylpentanamide This was produced analogously to example 13 through the use of D-leucine-tert-butyl ester and 3,5-dibromobenzyl bromide: MS(ES-neg) m/e 574.6 (M−H)⁻.

Example 19

N-hydroxy-2(R)-[7-(2-nitrophenoxy)-2,3,4,5-tetrahydrobenzo[1,2,5-f]thiadiazepine-1,1-dioxide]-4-methylpentanamide This was produced analogously to example 13 through the use of D-leucine-tert-butyl ester and 2-fluoro-1-nitrobenzene: MS(ES-neg) m/e 462.9 (M−H)⁻.

Example 20

N-hydroxy-2(R)-[7-(2-aminophenoxy)-2,3,4,5-tetrahydrobenzo[1,2,5-f]thiadiazepine-1,1-dioxide]-4-methylpentanamide This was produced from the above material via catalytic hydrogenation: MS(ES-neg) m/e 462.9 (M−H)⁻.

Example 21

N-hydroxy-2(R)-[7-(2,6-dichloropyridyl-4-methyleneoxy)-2,3,4,5-tetrahydrobenzo[1,2,5-f]thiadiazepine-1,1-dioxide]-4-methylpentanamide This was produced analogously to example 13 through the use of D-leucine-tert-butyl ester and 4-(bromomethyl)-2,6-dichloropyridine: MS(ES-neg) m/e 503.1 (M–H)⁻.

Example 22

N-hydroxy-2(R)-[7-(pyridyl-4-methyleneoxy)-2,3,4,5-tetrahydrobenzo[1,2,5-f]thiadiazepine-1,1-dioxide]-4-methylpentanamide This was produced analogously to example 13 through the use of D-leucine-tert-butyl ester and 4-picolyl chloride: MS(ES-neg) m/e 433.0 (M–H)⁻.

Example 23

N-hydroxy-2(R)-[7-(3,5-dichlorobenzyloxy)-2,3,4,5-tetrahydrobenzo[1,2,5-f]thiadiazepine-1,1-dioxide]-4-methylpentanamide This was produced analogously to example 13 through the use of D-leucine-tert-butyl ester and 3,5-dichlorobenzyl chloride: MS(ES-neg) m/e 499.7 (M–H)⁻.

Example 24

N-hydroxy-2(R)-[7-(3,5-dimethoxybenzyloxy)-2,3,4,5-tetrahydrobenzo[1,2,5-f]thiadiazepine-1,1-dioxide]-4-methylpentanamide This was produced analogously to example 13 through the use of D-leucine-tert-butyl ester and 3,5-dimethoxybenzyl chloride: MS(ES-neg) m/e 491.7 (M–H)⁻.

Example 25

N-hydroxy-2(R)-[7-(3,5-diethoxybenzyloxy)-2,3,4,5-tetrahydrobenzo[1,2,5-f]thiadiazepine-1,1-dioxide]-4-methoxycarbonylbutanamide This was produced analogously to example 13 through the use of D-glutamic-α-tert-butyl ester-δ-methyl ester and 3,5-diethoxybenzyl bromide: MS(ES-neg) m/e 549.8 (M–H)⁻.

Example 26

N-hydroxy-2(R)-[7-(3,5-dimethoxybenzyloxy)-2,3,4,5-tetrahydrobenzo[1,2,5-f]thiadiazepine-1,1-dioxide]-4methoxycarbonylbutanamide This was produced analogously to example 13 through the use of D-glutamic-α-tert-butyl ester-δ-methyl ester and 3,5-dimethoxybenzyl bromide: MS(ES-neg) m/e 521.9 (M–H)⁺.

Example 27

N-hydroxy-2(R)-[7-amino-2,3,4,5-tetrahydro-benzo[1,2,5-f]thiadiazepine-1,1-dioxide]-4-methylpentamide (27a) D-Leucine t-butyl ester hydrochloride salt (2.5 g, 11.2 mmol) was dissolved in methylene chloride (40 mL) and washed with 10% sodium carbonate (2×20 mL). After drying over MgSO₄ the solvent was evaporated in vacuo to provide the free base amino acid (1.82 g, 9.72 mmol). N-Methylmorpholine (1.47 g, 14.6 mmol) was added to D-leucine t-butyl ester in dioxane (20 mL) followed by dropwise addition of 2,4-dinitrobenzenesulfonyl chloride (2.85 g, 10.7 mmol) in dioxane (10 mL). After stirring for 24 h at room temperature, the solvent was evaporated in vacuo. The crude product was taken up in ethyl acetate (100 mL) and washed with water, 10% citric acid, saturated NaHCO₃(2×), and brine. After drying over MgSO₄ the solvent was evaporated in vacuo and the crude product was purified by flash chromatography (silica gel, 10 to 20% ethyl acetate/hexane) to afford 27a (3.61 g, 89%, MS, (ESI) m/e 416 (M–H)⁻) as a light yellow solid.

(27b) DEAD (1.12 g, 6.44 mmol) was added dropwise at room temperature to 27a (2.24 g, 5.37 mmol), triphenylphosphine (1.69 gm 6.44 mmol), and 2-bromoethanol (0.80 g, 6.44 mmol) in THF (20 mL). After stirring 24 h the solvent was removed in vacuo and the residue purified by flash chromatography (silica gel, 10 to 20% ethyl acetate/hexane) to provide 27b (2.52 g, 90%, MS, (ESI) m/e 522, 524 (M–H)⁻=) as a viscous oil.

(27c) Methanol (15 mL) was added carefully to 27b (0.26 g, 0.50 mmol) and 10% palladium on carbon (0.20 g) under a stream of nitrogen. A balloon filled with hydrogen was attached via a three way stopcock and the atmosphere above the reaction was removed and replace with hydrogen three times. After 0.5 h the catalyst was filtered washed with methanol and the solvent was removed in vacuo. The crude product was purified by flash chromatography (silica gel, 25–50% ethyl acetate/hexane) to provide 27c (185 mg, 80%, MS, (ESI) m/e 486, 488 (M+Na)⁺) as a clear oil.

(27d) N-Methyl morpholine (0.12 g, 1.16 mmol) was added to 27c (0.18 g, 0.38 mmol) in DMF (30 mL) then heated to 80° C. for 1 h. The solvent was removed in vacuo and the residue taken up in ethyl acetate then washed with water (3×) and brine. After drying over MgSO₄ the crude product was purified by flash chromatography (silica gel, 50–75% ethyl acetate/hexane) to provide 27d (86 mg, 58%, MS, (ESI) m/e 406 (M+Na)⁺) as a white solid.

(27e) Trifluoroacetic acid (3 mL) was added to 27d (55 mg, 0.14 mmol) and stirred at room temperature for 3 h. The trifluoroacetic acid was removed in vacuo followed by dissolving the crude product in chloroform (5 mL) then evaporation in vacuo, repeating three times. Drying overnight under vacuum provided crude 27e (67 mg, 100%, MS, (ESI) m/e 350 (M+Na)⁺) as a brittle foam that was carried forward without further purification.

(27f) Diisopropylethylamine (185 mg, 1.43 mmol) was added dropwise at 0° C. to 27e (0.14 mmol), BOP reagent (70 mg, 0.16 mmol), and hydroxyl amine hydrochloride (50 mg, 0.72 mmol) in DMF (3 mL). The cooling bath was removed after 0.5 h and the reaction allowed to stir overnight at room temperature. The solvent was removed in vacuo and the crude reaction mixture purified by flash chromatography (silica gel, 10% methanol/ethyl acetate) to provide example 27 (10 mg, 21%, MS, (ESI) m/e 341 (M–H)⁻).

Example 28

N-hydroxy-2(R)-[7-(N-acetylamino)-2,3,4,5-tetrahydro-benzo[1,2,5-f]thiadiazepine-1,1-dioxide]-4-methylpentamide (28a) Acetyl Chloride (18 mg, 0.22 mmol) was added to 27d (86 mg, 0.22 mmol) and triethylamine (113 mg, 1.12 mmol) in methylene chloride (2 mL) at room temperature. The reaction was stirred for 6 h then diluted with methylene chloride (10 mL) and washed with saturated NaHCO$_3$, water (3×) and brine. After drying over MgSO$_4$ the crude product was purified by flash chromatography (silica gel, 50–90% ethyl acetate/hexane) to provide 28a (55 mg, 59%, MS, (ESI) m/e 448 (M+Na)$^+$) as clear oil.

(28b) Following a procedure analogous to step 27e, 28a was treated with trifluoroacetic acid (3 mL) to provide 28b (MS, (ESI) m/e 368 (M–H)$^-$) as a clear oil that was carried forward without further purification.

(28c) Diisopropylethylamine (84 mg, 0.65 mmol) was added dropwise at 0° C. to 28b (0.13 mmol), BOP reagent (63 mg, 0.14 mmol), and benzylhydroxyl amine hydrochloride (42 mg, 0.26 mmol) in DMF (3 mL). The ice bath was removed after 0.5 h and the reaction allowed to stir overnight at room temperature. The solvent was removed in vacuo and the residue taken up in ethyl acetate (20 mL) and washed with water (2×), saturated NaHCO$_3$(2×), and brine. After drying over MgSO$_4$ the crude product was purified by flash chromatography (silica gel, 80–100% ethyl acetate/hexane) to provide 28c (35 mg, 56%, MS, (ESI) m/e 497 (M+Na)$^+$) as a white solid.

(28d) 5% Palladium on barium sulfate (unreduced, 100 mg) was added to 28c (35 mg, 0.07 mmol) in methanol (10 mL). A balloon filled with hydrogen was attached via a three way stopcock and the atmosphere above the reaction was removed and replace with hydrogen three times. After 0.45 h the catalyst was filtered washed with methanol then the solvent was removed in vacuo. The crude product was taken up in THF (1 mL) and was crystallized by slow addition of ether (30 mL). The hydroscopic solid was filtered and dried under vacuum to provide example 28 (10 mg, 37%, MS, (ESI) m/e 383 (M–H)$^-$).

Example 29

N-hydroxy-2(R)-[7-(N-(2-phenylacetylamino)-2,3,4,5-tetrahydro-benzo[1,2,5-f]thiadiazepine-1,1-dioxide]-4-methylpentamide Example 29 was prepared in a analogous series of reactions to example 28, beginning with 27d and phenylacetylchloride (MS, (ESI) m/e 459 (M–H)$^-$).

Example 30

N-hydroxy-2(R)-[2,3,4,5-tetrahydro-benzo[1,2,5-f] thiadiazepine-1,1-dioxide]-4-methylpentamide (30a) Sodium Nitrate (15 mg, 0.21 mmol) in water (1 mL) was added dropwise to 27d (74 mg, 0.19 mmol) in a mixture of acetic acid/water (5 mL, 4:1) at 0° C. After 0.25 h potassium iodide (48 mg, 0.29 mmol) and iodine (37 mg, 0.14 mmol) were added to the red solution in one portion. The reaction was stirred 2 h at 0° C. then allowed to warm to room temperature and stirred for an additional 4 h. The reaction was diluted with water (10 mL) then extracted with ethyl acetate (3×). The combined organic layers were washed with water (2×), saturated NaHCO$_3$ (3×) and brine. After drying over MgSO$_4$ the crude product was purified by flash chromatography (silica gel, 10–35% ethyl acetate/hexane) to provide 30a (34 mg, 36%, MS, (ESI) m/e 517 (M+Na)$^+$) yellow oil.

(30b) Following a procedure analogous to step 27e, 30a was treated with trifluoroacetic acid (3 mL) to provide 30b (MS, (ESI) m/e 437 (M–H)$^-$) as a clear oil that was carried forward without further purification.

(30c) Following a procedure analogous to step 28c, 30b was treated with diisopropylethylamine in the presence of BOP reagent, and benzylhydroxylamine hydrochloride to provide 30c (MS, (ESI) m/e 566 (M+Na)$^+$) as a viscous oil that was purified by flash chromatography.

(30d) Following a procedure analogous to step 28d, 30c was treated with hydrogen in the presence of 5% palladium on barium sulfate to provide 30d (MS, (ESI) m/e 440 (M+Na)$^+$) as a brittle foam that was purified by flash chromatography.

(30e) Following a procedure analogous to step 28d, 30d was treated with hydrogen in the presence of 5% palladium on barium sulfate to provide example 30 (MS, (ESI) m/e 350 (M+Na)$^+$) as a brittle foam.

Example 31

N-hydroxy-2(R)-[7-(N-(3,5-dimethoxymethyleneamino)-2,3,4,5-tetrahydro-benzo[1,2,5-f]thiadiazepine-1,1-dioxide]-4-methylpentamide (31a) Ethanol (300 µL) was added to 27d (117 mg, 0.31 mmol) and 3,5-dimethoxybenzaldehyde (51 mg, 0.31 mmol) then stirred 5 h at room temperature. Sodium borohydride (12 mg, 0.31 mmol) was added in one portion and the viscous reaction was stirred overnight at room temperature. The reaction was quenched with saturated ammonium chloride (3 mL) then diluted with water (10 mL). The aqueous solution was extracted with ethyl acetate (3×) and the combined organic layers were washed with water, saturated NaHCO$_3$, and brine. After drying over MgSO$_4$ the solvent was evaporated in vacuo and the crude product was purified by flash chromatography (silica gel, 50–85% ethyl acetate/hexane) to provide 31a (104 mg, 64%, MS, (ESI) m/e 532 (M–H)$^-$).

(31b) Following a procedure analogous to step 27e, 31a was treated with trifluoroacetic acid (3 mL) to provide 31b (MS, (ESI) m/e 476 (M–H)$^-$) as a brittle foam that was carried forward without further purification.

(31c) Following a procedure analogous to step 28c, 31b was treated with diisopropylethylamine in the presence of BOP reagent, and benzylhydroxylamine hydrochloride to provide 31c (MS, (ESI) m/e 605 (M+Na)$^+$) which was purified by flash chromatography.

(31d) Following a procedure analogous to step 28d, 31c was treated with hydrogen in the presence of 5% palladium on barium sulfate to provide example 31 (MS, (ESI) m/e 515 (M+Na)$^+$) as a tan solid.

Example 32

N-hydroxy-2(R)-[7-(N-(3,5-dimethylphenylmethyleneamino)-2,3,4,5-tetrahydro-benzo[1,2,5-f]thiadiazepine-1,1-dioxide] propylamide (32a) Saturated NaHCO$_3$ (10 mL) was added to D-alanine methyl ester hydrochloride salt (1 g, 7.91 mmol) suspended in chloroform (20 mL) followed by addition of 2,4-dinitrobenzenesulfonyl chloride (1.91 g, 7.16 mmol) portionwise over 1 min. After stirring vigorously overnight at room temperature the precipitated solid was filtered and washed successively with water (20 mL) and cold chloroform (20 mL). The solid was dried under vacuum to provide 32a (1.83 g, 77%, MS, (ESI) m/e 332 (M–H)$^-$) as a light yellow solid.

(32b) Following a procedure analogous to step 27b, 32a was treated with DEAD, triphenylphosphine, and 2-bromoethanol to provide 32b (MS, (ESI) m/e 438, 440

(M–H)⁻) as a viscous oil that was purified by flash chromatography.

(32c) Iron dust (7.65 g, 137 mmol) was added in one portion to 32b (6.03 g, 13.7 mmol) in acetic acid/water (84 mL, 20:1) then heated to 60° C. for 1.5 h. The reaction was diluted with ethyl acetate (500 mL) and the solids were filtered. Stirring vigorously saturated NaHCO₃ (200 mL) was added to the ethyl acetate solution followed by addition of solid NaHCO₃ until no gas evolution was noted. The aqueous solution was extracted with ethyl acetate (1×) then the combined ethyl acetate layers were washed with water, saturated NaHCO₃ (2×), and brine. After drying over MgSO₄ the crude product was concentrated then purified by flash chromatography (silica gel, 50–100% ethyl acetate/hexane) to provide 32c (3.21 g, 62%, MS, (ESI) m/e 402, 404 (M+Na)⁺).

(32d) N-Methyl morpholine (1.71 g, 16.9 mmol) was added to 32c (3.21 g, 8.44 mmol) in DMF (250 mL) then heated to 60° C. for 5.5 h. The solvent was removed in vacuo and the residue taken up in ethyl acetate (100 mL) then washed with water (2×), saturated NaHCO₃ (2×), and brine. After drying over MgSO₄ the crude product was concentrated in vacuo then purified by flash chromatography (silica gel, 50–100% ethyl acetate/hexane) to provide 32d (1.76 g, 70%, MS, (ESI) m/e 322 (M+Na)⁺) as a white solid.

(32e) 3,5-Dimethylbenzaldehyde (0.15 g, 1.14 mmol) was added to 32d (0.17 g, 0.57 mmol) in methanol (2 mL) and stirred at room temperature for 0.25 h. 10% Palladium on carbon (70 mg) was added carefully followed by additional methanol (5 mL). A balloon filled with hydrogen was attached via a three way stopcock and the atmosphere above the reaction was removed and replace with hydrogen three times. After stirring overnight the catalyst was filtered washed with methanol and the solvent was removed in vacuo. The crude product was purified by flash chromatography (silica gel, 50% ethyl acetate/hexane) to provide 32e (174 mg, 73%, MS, (ESI) m/e 440 (M+Na)⁺).

(32f) Lithium hydroxide hydrate (52 mg, 1.25 mmol) in water (1 mL) was added to 32e (174 mg, 0.42 mmol) in THF (3 mL) at room temperature. The reaction was complete in 2 h and the solvent was removed in vacuo. The residue was taken up in water (10 mL) and washed with ether (2×). The ether layer was discarded and the aqueous layer was acidified with 1N HCl. The aqueous layer was then extracted with ethyl acetate (3×) and the combined organic layers were washed with brine, dried over MgSO₄, then evaporated in vacuo to provide 32f (MS, (ESI) m/e 402 (M–H)⁻) which was carried forward without further purification.

(32g) Following a procedure analogous to step 28c, 32f was treated with diisopropylethylamine in the presence of BOP reagent, and benzylhydroxylamine hydrochloride to provide 32g (MS, (ESI) m/e 531 (M+Na)⁺).

(32h) Following a procedure analogous to step 28d, 32g was treated with hydrogen in the presence of 5% palladium on barium sulfate to provide example 32 after purification by flash chromatography (silica gel, 0–20% methanol/ethyl acetate 16 mg, 14%, MS, (ESI) m/e 441 (M+Na)⁺) as an amorphous white solid.

Example 33

N-hydroxy-2(R)-[7-(N-benzoylamino)-2,3,4,5-tetrahydro-benzo[1,2,5-f]thiadiazepine-1,1-dioxide] propylamide (33a) Following a procedure analogous to step 32f, 32c was treated with lithium hydroxide in the THF/water to provide example 33a (1.55 g, 93%, MS, (ESI) m/e 284 (M–H)⁻) which was carried forward without further purification.

(33b) Following a procedure analogous to step 28c, 33a was treated with diisopropylethylamine in the presence of BOP reagent, and benzylhydroxylamine hydrochloride to provide 33b (MS, (ESI) m/e 413 (M+Na)⁺).

(33c) Benzoyl chloride (60 µL, 0.50 mmol) was added to 33b (130 mg, 0.33 mmol) in a mixture of dioxane/water/saturated NaHCO₃ (4 mL, 2:1:1) then stirred 2 h at room temperature. The reaction was diluted with ethyl acetate (30 mL) and washed with saturated NaHCO₃ and brine. After drying over MgSO₄ the crude product was concentrated then purified by flash chromatography (silica gel, 50–85% ethyl acetate/hexane) to provide 33c (92 mg, 56%, MS, (ESI) m/e 517 (M+Na)⁺).

(33d) Following a procedure analogous to step 28d, 33c was treated with hydrogen in the presence of 5% palladium on barium sulfate to provide example 33 (MS, (ESI) m/e 427 (M+Na)⁺) as an amorphous white solid.

Example 34

N-hydroxy-2(R)-[7-(N-3,5-dimethoxybenzoylamino)-2,3,4,5-tetrahydro-benzo[1,2,5-f]thiadiazepine-1,1-dioxide]propylamide Example 34 was prepared in a analogous series of reactions to example 33, beginning with 33b and 3,5-dimethoxybenzoyl chloride (MS, (ESI) m/e 487 (M+Na)⁺).

Example 35

N-hydroxy-2(R)-[7-(N-3,5-dimethylbenzoylamino)-2,3,4,5-tetrahydro-benzo[1,2,5-f]thiadiazepine-1,1-dioxide]propylamide Example 35 was prepared in a analogous series of reactions to example 33, beginning with 33b and 3,5-dimethybenzoyl chloride (MS, (ESI) m/e 455 (M+Na)⁺).

Example 36

N-hydroxy-2(R)-[7-(phenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl) methyl]acetamide (36a) DEAD (2.31 g, 13.3 mmol) was added dropwise at room temperature to N-trityl-D-serine methyl ester (4.00 g, 11.1 mmol), triphenylphosphine (3.48 gm 13.3 mmol), and 5,5-dimethylhydantoin (1.70 g, 13.3 mmol) in benzene (100 mL). After stirring 3 h the precipitated solids were removed by filtration through celite and the crude reaction mixture was concentrated in vacuo. The product was purified by flash chromatography (silica gel, 35 to 65% ethyl acetate/hexane) to afford 36a (5.24 g, 100%, MS, (ESI) m/e 494 (M+Na)⁺) as a light yellow solid.

(36b) Sodium hydride (60% in mineral oil, 0.44 g, 11.1 mmol) was added in one portion to 36a (5.24 g, 11.1 mmol) in DMF (25 mL) at 0° C. The reaction was stirred 0.5 h at 0° C. then 0.5 h at room temperature, followed by dropwise addition of iodomethane (1.88 g, 13.3 mmol). After stirring overnight the reaction was quenched with saturated NH₄Cl (2 mL). The solvent was removed in vacuo and the residue taken up in ethyl acetate (100 mL), washed with water, saturated NaHCO₃, and brine then dried over MgSO₄. The product was concentrated in vacuo and purified by flash chromatography (silica gel, 50 to 65% ethyl acetate/hexane) to provide 36b (3.94 g, 73%, MS, (ESI) m/e 508 (M+Na)$^{30}$ ).

(36c) 36b (2.89 g, 5.95 nmol) was taken up in 1N HCl in ethanol (20 mL) and refluxed for 10 min. The solvent was removed in vacuo and the resulting solid triturated with ether (2x). The hydroscopic solid was filtered then dried under vacuum to provide 36c (1.62 g, 97%, MS, (ESI) m/e 244 (M+H)$^+$) as hydroscopic white solid.

(36d) 2-nitro-4-benzyloxybenzenesulfonyl chloride (2.29 g, 6.99 mmol) was added in one portion to 36c (1.62 g, 5.79 mmol) in mixture of saturated NaHCO$_3$ and chloroform (30 mL, 1:2). After stirring vigorously overnight the solvent was removed in vacuo and the residue taken up in a mixture of ethyl acetate/water (50 mL, 1:1). After extracting with ethyl acetate (3x) the combined organic layers were washed with water, 1N HCl, saturated NaHCO$_3$, and brine. The organic layer was dried over MgSO$_4$, concentrated in vacuo, then purified by flash chromatography (silica gel, 20 to 80% ethyl acetate/ hexane) to provide 36d (1.68 g, 54%, MS, (ESI) m/e 557 (M+Na)$^+$).

(36e) DEAD (0.81 g, 4.66 mmol) was added dropwise at room temperature to 36d (1.66 g, 3.11 mmol), triphenylphosphine (1.25 gm 4.66 mmol), and 2-bromoethanol (0.58 g, 4.66 mmol) in benzene (100 mL). After stirring overnight the precipitated solids were removed by filtration through celite and the crude reaction mixture was concentrated in vacuo. The product was purified by flash chromatography (silica gel, 50 to 70% ethyl acetate/ hexane) to afford 36e (2.11 g, 100%, MS, (ESI) m/e 639,641 (M–H)$^-$) as a viscous yellow oil.

(36f) Iron dust (1.61 g, 28.8 mmol) was added in one portion to 36e (1.85 g, 2.88 mmol) in acetic acid/water (32 mL, 15:1) then heated to 50° C. for 3 h. The reaction was diluted with ethyl acetate (300 mL) and the solids were filtered. Stirring vigorously saturated NaHCO$_3$ (200 mL) was added to the ethyl acetate solution followed by addition of solid NaHCO$_3$ until no gas evolution was noted. The aqueous solution was extracted with ethyl acetate (1x) then the combined ethyl acetate layers were washed with water, saturated NaHCO$_3$ (2x), and brine. The product was concentrated in vacuo and taken up in DMF (35 mL). N-Methyl morpholine (0.58 g, 5.76 mmol) was added and the reaction was heated to 60° C. for 6 h. The solvent was removed in vacuo and the residue taken up in ethyl acetate/water (100 mL, 1:1) The resulting solid was filtered and dried under vacuum to provide 36f (0.68 g, 45%, MS, (ESI) m/e 531 (M+H)$^+$).

(36g) Following a procedure analogous to step 32f, 36f was treated with lithium hydroxide in the THF/water to provide 36 g (1.55 g, 93%, MS, (145 mg, 100%, MS, (ESI) m/e 515 (M–H)$^-$) which was carried forward without further purification.

(36h) Diisopropylethylamine (174 mg, 1.35 mmol) was added dropwise at 0° C. to 37g (0.27 mmol), BOP reagent (131 mg, 0.30 mmol), and hydroxyl amine hydrochloride (56 mg, 0.81 mmol)in DMF (3 mL). The cooling bath was removed after 0.5 h and the reaction allowed to stir overnight at room temperature. The solvent was removed in vacuo and the residue taken up in ethyl acetate (20 mL) and washed with water (2x), 10% citric acid, saturated NaHCO$_3$ (2x), and brine. After drying over MgSO$_4$ the crude product was concentrated then purified by reverse phase HPLC(C$_{18}$, water/acetonitrile) to provide example 36 (41 mg, 29%, MS, (ESI) m/e 554 (M+Na)$^+$) as a white powder.

Example 37

N-hydroxy-2(R)-[7-(3,5-dimethoxyphenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl)methyl] acetamide (37a) Methanol (30 mL) was added carefully to 36g (0.68 g, 1.28 mmol) and 10% palladium on carbon (0.25 g) under a stream of nitrogen. A balloon filled with hydrogen was attached via a three way stopcock and the atmosphere above the reaction was removed and replaced with hydrogen three times. After 2 h the catalyst was filtered washed with methanol then the solvent was removed in vacuo. The crude product was recrystallized from ethyl acetate/ hexane to provide 37a (0.58 g, 100%, MS, (ESI) m/e 463 (M+Na)$^+$) as white solid.

(37b) Potassium t-butoxide (1M in THF, 0.18 mL, 0.18 mmol) was added dropwise to 37a (81 mg, 0.18 mmol) in anhydrous DMF at 0° C. After 0.5 h 3,5-dimethoxybenzylchloride (51 mg, 0.28 mmol) was added in one portion. The reaction was allowed to warm to room temperature and stirred overnight. The solvent was evaporated in vacuo and the residue taken up in ethyl acetate/ water (20 mL, 1:1). After extracting with ethyl acetate (3x) the combined organic layers were washed with water, saturated NaHCO$_3$ (2x), and brine then dried over MgSO$_4$. The solvent was removed in vacuo and the crude product purified by flash chromatography (50–80% ethyl acetate/hexanes, 49 mg, 38%, MS, (ESI) m/e 589 (M–H)$^-$) to provide 37b as a waxy solid.

(37c) Following a procedure analogous to step 32f, 37b was treated with lithium hydroxide in the THF/water to provide 38c (MS, (ESI) m/e 575 (M–H)$^-$) which was carried forward without further purification.

(37d) Following a procedure analogous to step 36h, 37c was treated with diisopropylethylamine, BOP reagent, and hydroxylamine hydrochloride to provide example 37 (17 mg, 36%, MS, (ESI) m/e 614 (M+Na)$^+$) as a white powder.

Example 38

N-hydroxy-2(R)-[7-(3,5-dimethylphenylmethyleneoxy)-2,3,4,5-tetrahydro-benzo[1,2,5-f]thiadiazepine-1,1-dioxide]2-[(3,4,4-trimethyl-2,5-dioxa-1-imidazolidinyl)methyl] acetamide Example 38 was prepared in a analogous series of reactions to example 37, beginning with 37a and 3,5-dimethylbenzyl bromide (MS, (ESI) m/e 582 (M+Na)$^+$)

Example 39

N-hydroxy-2(R)-[7-(3,5-dibromophenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl)methyl] acetamide Example 39 was prepared in a analogous series of reactions to example 37, beginning with 37a and 3,5-dibromobenzyl bromide (MS, (ESI) m/e 712 (M+Na)$^+$).

Example 40

(R)-3,4-Dihydro-N-hydroxy-alpha-(1-methylethyl)-2H-1,2-benzothiazine-2-acetamide-1,1-dioxide (40a) Sodium hydride (1.92 g, 1.2 eq, 60% in mineral oil) was added in several portions to a dry solution of 2-bromophenethyl alcohol (8.43 g 42 mmol) in a mixture of THF (50 mL) and DMF (25 mL) at rt. Allowed to stir for 10 min before the addition of benzyl bromide (4.98 g, 1.0 eq) to the reaction mixture. After 1 h at 80° C., water (100 mL) was added at rt then extracted with ethyl acetate (3×200 mL). The combined extracts were washed with water (50 mL), brine (50 mL), dried (MgSO$_4$) and concentrated. SiO$_2$ column chromatography (ethyl acetate-hexane, 25:75) yielded the desired product (10 g, 82%) (MS found: M+H=292).

(40b) n-BuLi (10.73 mL, 1.6 M in hexanes) was added in a dropwise fashion to a solution of 40a (5.0 g) dissolved in dry THF (110 mL) at −60° C. over 5 min. The mixture was then canulated into a solution of SO$_2$ (52 g) gas condensed into freshly distilled THF (110 mL) at −60° C. over 10 min. The cold bath was removed and the mixture was stirred at ambient temperature for 1 h. The reaction mixture was concentrated to afford the desired lithium arylsulfinate (5.0 g) (MS found: M+H=283)

(40c) Sulfuryl chloride (1.42 mL, 1.0 eq) was added dropwise to a solution of the lithium arylsulfinate suspended in a mixture of dichlormethane (100 mL) and hexane (100 mL). After one hour the reaction mixture was concentrated to provide the desired arylsulfonyl chloride (4.0 g, 73%) (MS found: M+H=311).

(40d) The arylsulfonyl chloride (1.00 g, 3.2 mmol) was added to a solution of D-valine methyl ester (0.85 g, 2.0 eq) and triethylamine (1.81 mL, 4.0 eq) in CH$_2$Cl$_2$ (50 mL) at 0° C. The cold bath was removed and the mixture was stirred at ambient temperature overnight. Following addition of citric acid (150 mL), the mixture was extracted with CH$_2$Cl$_2$ (3×250 mL), water (1×100 mL), brine (50 mL), dried (MgSO$_4$) and concentrated to give the desired sulfonamide (1.0 g, 77%) (MS found: M+H=406).

(40e) Sulfonamide (0.84 g, 2.07 mmol) was added to a suspended solution of Pd-C (0.10 g, 10% by weight) in methanol (20 mL) in a Parr-bottle. The solution was hydrogenated for 3 h at 50 psi (H$_2$). Filtration and concentration gave the desired alcohol (0.60 g, 92%) (MS found: M+H=316).

(40f) Triphenylphosphine (0.60 g, 1.2 eq) was added to the alcohol (0.60 g, 1.9 mmol) dissolved in THF (5 mL) at 0° C. DEAD (0.38 mL, 1.2 eq) was added dropwise to the reaction. The cold bath was removed and the mixture was stirred at ambient temperature for 3 h. The reaction was concentrated and purified by SiO$_2$ column chromatography (ethyl acetate-hexane, 25:75) to give the desired product (0.46 g, 81%) (MS found: M+H=298).

(40g) Lithium hydroxide (260 mg, 5 eq) was added to the methyl ester dissolved into a mixture of THF (3 mL) and water (3 mL) at ambient temperature for 2 days. Following addition of 1 N HCl (30 mL), the mixture was extracted with ethyl acetate (3×50 mL), water (50 mL), brine (25 mL), dried (MgSO$_4$), concentrated to give the desired carboxylic acid (250 mg, 100%) (MS found: M+H=283).

(40h) TBTU (2-(1H-benzotriazol-1-yl)-1,1,3,3-tetramethyluronium tetrafluoroborate) (0.425 g, 1.5 eq) was added to a solution of carboxylic acid (0.250 g, 0.89 mmol), O-Benzylhydroxylamine (1.09 g, 10 eq, free base) and NMM (0.29 mL, 3.0 eq) in DMF (5 mL) at rt. After stirring overnight the mixture was heated at 80° C. for 30 min, then concentrated. Following addition of citric acid (50 mL), the mixture was extracted with ethyl acetate (3×50 mL), washed with NaHCO$_3$ (sat) (2×50 mL), water (3×50 mL), brine (50 mL), dried (MgSO$_4$) and concentrated. Purified by SiO$_2$ column chromatography (ethyl acetate-hexane, 25:75 then 50:50) to give the desired product (0.120 g, 35%) (MS found: M+H=389).

(40i) The O-benzylhydroxamic acid (0.120 g, 31 mmol) was added to a suspended solution of Pd—Ba$_2$SO$_4$ (0.350 g, 5% by weight) in methanol (10 mL). The solution was treated with H$_2$ at 1 atm (balloon). After 1 h the mixture was filtered and concentrated to give the desired hydroxamic acid (100 mg, 100%) (MS found: M+H=299).

Example 41

(R)-3,4-Dihydro-N-hydroxy-alpha-2H-1,2-benzothiazine-2-acetamide-1,1-dioxide (41a) 10 g of 2-nitrophenylacetronitrile was dissolved in 60 mL of ethanol. To this was added 980 mg of 10% Pd/C. A solution of hydrazine hydrate (9.2 mL) was added slowly to the solution over a period of an hour, so that the reaction didn't warm above 35° C. When the reaction was judged complete by TLC, the mixture was filtered and concentrated in vacuo to provide crude product 8.53 g (100%). $^1$H NMR (400 MHz, CDCl$_3$) d 7.31 (m, 3H), 7.07 (m, 1H), 3.66 (s, 2H).

(41b) A solution of NaNO$_2$ (3.75 g) in H$_2$O (17.55 mL) was added slowly to a well stirred suspension of the amine (8.27 g) in glacial acetic (57.8 mL) and concentrated HCl (103 mL) at 0° C. After the addition was complete, the mixture was stirred at 0° C. for 30 min. To a second flask was added 3.92 g of cupric chloride (CuCl$_2$, anhydrous), 80.5 mL of glacial acetic acid, 13.67 mL of water and 39 mL of SO$_2$ at 0° C. The first flask was slowly added in portions to the second flask at 0° C. and allowed to stir at 0° C. for 15 min then warmed to rt and allowed to stir for 2 h. The reaction was quickly added to 600 mL of water containing solid ice. A brown precipitate formed and this was filtered and provided 5.7 g of brown product (42%). $^1$H NMR (400 MHz, CDCl$_3$) d 8.17 (d, J=8.42 Hz, 1H), 7.88 (t, J=7.69 Hz, 1H), 7.84 (d, J=7.32 Hz, 1H), 7.64 (t, J=7.32 Hz, 1H), 4.39 (s, 2H).

(41c) The acid chloride (0.148 g) was dissolved in 7.75 mL of MeOH. To this was added 0.079 g (2.0 equiv.) of KOH pellets. The reaction turned brown. After judged complete by TLC, the reaction was filtered to remove KCl and the flask was washed with MeOH. The reaction was concentrated to remove most of the MeOH. The flask was put in the freezer to give crystals of product (0.15 g, 100%). $^1$H NMR (400 MHz, DMSO-D$_6$) d 7.73 (d, J=7.33 Hz, 1H), 7.27–7.38 (m, 3H), 4.32 (s, 2H).

(41d) To the salt was added 0.43 g of 10% Pd/C, followed by 100 mL of MeOH and 5.5 mL of concentrated HCl. This was then subjected to a balloon of hydrogen and allowed to stir overnight. The reaction was then filtered and concentrated to provide 2.3 g of crude product (96%). $^1$H NMR (400 MHz, CD$_3$OD) d 7.93 (d, J=7.69 Hz, 1H), 7.43–7.31 (m, 3H), 3.43–3.21 (m, 4H).

(41e) The sulfonic acid (0.45 g) was dissolved in 6 mL of POCl$_3$ and allowed to reflux for 1.5 h. The reaction was allowed to cool and the solvent was removed in vacuo. The residue was put in an ice-bath and carefully treated with 20% NaOH solution until basic. This was allowed to reflux for 1 h and then allowed to cool again to 0° C. The reaction was then treated with 2 N HCl until acidic and the solution was concentrated until dryness. The residue was then washed with MeOH, filtered to remove inorganic salts, and concentrated to dryness. The residue was then chromatographed with 35% EtOAc/hex to give pure product (0.13 g, 45%). $^1$H NMR (400 MHz, CD$_3$OD) d 7.66 (d, J=7.69 Hz, 1H), 7.48 (t, J=7.69 Hz, 1H), 7.39 (d, J=7.32 Hz, 1H), 7.32 (t, J=7.69 Hz, 1H), 3.52 (q, J=6.23 Hz, 2H), 3.20 (bs, 1H), 2.88 (t, J=6.23 Hz, 2H).

(41f) The sulfonamide (59 mg) was dissolved in 1 mL of DMF and to this solution was added 0.45 g (10.0 eq) of powdered $K_2CO_3$ at rt. After 10 min, tert-butyl bromoacetate (0.058 mL) was added and this was allowed to stir overnight at rt. The reaction was diluted with ethyl acetate, filtered to remove $K_2CO_3$, and the filtrate was extracted with 1 N HCl and $NaHCO_3$. The organic layer was concentrated in vacuo and chromatographed with 30% EtOAc/hex to provide 0.085 g (89%) of pure product. $^1$H NMR (400 MHz, $CDCl_3$) d 7.79 (d, J=7.69 Hz, 1H), 7.36 (t, J=7.32 Hz, 1H), 7.26 (t, J=7.32 Hz, 1H), 7.24 (d, J=7.69 Hz, 1H), 3.91 (s, 2H), 3.89 (t, J=6.23 Hz, 2H), 3.08 (t, J=6.23 Hz, 2H), 1.41 (s, 9H).

(41g) The tert-butyl acetate (0.079 g) was treated with 5 mL of $CH_2Cl_2$ and 0.75 mL of TFA and allowed to stir overnight. The solvent was removed in vacuo to provide 0.064 g (100%) of crude product. $^1$H NMR (400 MHz, $CDCl_3$) d 7.79 (d, J=8.05 Hz, 1H), 7.49 (t, J=7.69 Hz, 1H), 7.39 (t, J=7.32 Hz, 1H), 7.27 (d, J=6.59 Hz, 1H), 3.93 (t, J=6.22 Hz, 2H), 3.09 (t, J=6.22 Hz, 2H).

(41h) The acid (0.060 g) was dissolved in 2 mL of DMF and brought down to 0° C. To this was added diisopropylethylamine (0.277 mL) and BOP (0.14 g) and allowed to stir overnight at rt. The reaction was diluted with ethyl acetate and washed with 1 N HCl and $NaHCO_3$. The organic layer was dried ($MgSO_4$), concentrated in vacuo, and chromatographed with 60% EtOAc/hex to provide pure product (0.076 g, 88%). $^1$H NMR (400 MHz, DMSO-$D_6$) d 7.68 (d, J=7.69 Hz, 1H), 7.53 (t, J=7.69 Hz, 1H), 7.42 (d, J=7.32 Hz, 1H), 7.36 (m, 6H), 4.77 (s, 2H), 3.78 (t, J=6.23 Hz, 2H), 2.98 (t, J=6.23 Hz, 2H).

(41i) The hydroxamic ester (21.5 mg) was dissolved in 10 mL of 40% $CHCl_3$/MeOH and treated with 100 mg of Pd/$BaSO_4$ and subjected to hydrogenation at 50 PSI overnight. The solvent was then removed in vacuo to provide crude product (0.0153 g, 96%)which was pure by NMR and M.S. $^1$H NMR (400 MHz, $CD_3OD$) d 7.69 (d, J=7.32 Hz, 1H), 7.46 (t, J=6.96 Hz, 1H), 7.39 (t, J=6.96 Hz, 1H), 7.32 (d, J=7.32 Hz, 1H), 4.87 (s, 2H), 3.88 (m, 2H), 3.05 (m, 2H). MS(CI) m/e 273 (M+$NH_4$)$^+$.

Example 42

N-hydroxy-2(R)-[7-(3,5-dimethoxybenzyloxy)-2,3,4,5-tetrahydrobenzo[1,2,5-f]thiadiazepine-1,1-dioxide]-5-methoxycarbonylpentanamide 42a. Tert-butyl-2(R)-[7-benzyloxy-2,3,4,5-tetrahydrobenzo[1,2,5-f]thiadiazepine-1,1-dioxide]-3-methoxycarbonylpropanoate was produced analogously to example 6(E) by the use of D-Asp(Me)tBu in step (C): MS(ES-pos) m/e 512.9 (M+Na)$^+$.

42b. The above material (800 mg, 1.6 mmol) was dissolved in $CH_2Cl_2$ and cooled to −78° C. Then 1M Dibal (3.7 mL, 3.7 mmol) was added in three portions. After 30 min, the reaction was quenched with a solution of Rochelle's salt. The organic layer was concentrated. Chromatography of the resulting residue gave the aldehyde (570 mg, 1.2 mmol): MS(ES-pos) m/e 483.2 (M+Na)$^+$.

42c. The above material (570 mg, 1.2 mmol) was dissolved in THF and methyl (triphenylphosphoranylidene) acetate (829 mg) was added. After 1.5 h the solution was concentrated. Chromatography of the resulting residue gave the olefin (600 mg, 1.1 mmol): MS(ES-pos) m/e 539.0 (M+Na)$^+$.

42d. The above material (600 mg, 1.1 mmol) was dissolved in MeOH prior to the addition of 10% Pd/C (60 mg). This solution was placed on a Parr at 50 psi. After stirring overnight, the palladium was removed and the solution was concentrated. This gave the phenol (470 ng): MS(ES-neg) m/e 427.0 (M−H)$^−$.

42e. The above material (230 mg, 0.54 mmol) was dissolved in DMF prior to the addition of 3,5-dimethoxybenzyl chloride(110 mg) and NaI (81 mg). At room temperature $Cs_2CO_3$ (315 mg) was added. After 4 h, the solution was concentrated and quenched with aqueous $NH_4Cl$ then extracted with EtOAc. The organic layer was concentrated. Chromatography of the resulting residue gave the alkylated product (170 mg): MS(ES-pos) m/e 601.0 (M+Na)$^+$.

42f. The above material (170 mg) was dissolved in $CH_2Cl_2$ prior to the addition of TFA (3 mL). After 7 h, the solution was concentrated to the crude acid. The crude acid was dissolved in DMF and diisopropylethylamine (0.55 mL) was added. The mixture was cooled to 0° C. and BOP (140 mg) was added. After 20 min at 0° C., $HONH_2$·HCl (80 mg) was added. The reaction was stirred 1 hr and then HPLC chromatography gave the title hydroxamate (70 mg): MS(ES-neg) m/e 650.1 (M−1+TFA)$^−$.

Example 43

N-hydroxy-2(R)-[7-(3,5-diethoxybenzyloxy)-2,3,4,5-tetrahydrobenzo[1,2,5-f]thiadiazepine-1,1-dioxide]-5-methoxycarbonylpentanamide This was produced analogously to example 42 through the use of 3,5-diethoxybenzyl bromide in step (e): MS(ES-pos) m/e 566.2 (M+H)$^+$.

Example 44

N-hydroxy-2 (R)-[7-(3,5-dimethoxybenzyloxy)-2,3,4,5-tetrahydrobenzo[1,2,5-f]thiadiazepine-1,1-dioxide]-6-methoxycarbonylhexanamide This was produced analogously to example 42 through the use of D-Glu(Me)tBu in step (a): MS(ES-neg) m/e 550.2 (M−H)$^−$.

Example 45

N-hydroxy-2 (R)-[7-(3,5-dimethoxybenzyloxy)-2,3,4,5-tetrahydrobenzo[1,2,5-f]thiadiazepine-1,1-dioxide]-6-hydroxycarbonylhexanamide The material from Example 44 (82 mg) was dissolved in THF and water. At room temperature, 1M LiOH (0.15 mL) solution was added. After 6 h, TFA was added and the solution was concentrated. HPLC chromatography of the resulting residue gave the title hydroxamate (10 mg): MS(ES-neg) m/e 536.1 (M−H)$^−$.

Example 46

N-hydroxy-2(R)-[7-4-nitrophenoxy)-2,3,4,5-tetrahydrobenzo[1,2,5-f]thiadiazepine-1,1-dioxide]-propanamide 46a. The phenol from example 6F (200 mg, 0.67 mmol) was dissolved in DMF prior to the addition of 1-fluoro-4-nitrobenzene (0.08 mL, 0.74 mmol). At room temperature, $Cs_2CO_3$ (391 mg, 1.2 mmol) was added. After 2.5 h, the solution was quenched with aqueous $NH_4Cl$ and extracted with EtOAc. The organic layer was concentrated. Chromatography of the resulting residue gave methyl-2(R)-[7-(4-nitrophenoxy) -2,3,4,5-tetrahydrobenzo[1,2,5-f]thiadiazepine-1,1-dioxide]-propanoate (170 mg): MS(ES-neg) m/e 420.1 (M−H)⁻.

46b. Following a procedure analogous to that in step (1d),the ester (165 mg) from above was reacted with the hydroxylamine solution (4 mL) at room temperature. After 1 h, water and EtOAc were added. The organic layer was concentrated. Chromatography of the resulting residue gave the title hydroxamate (120 mg): MS(AP-pos) m/e 423.1 (M+H)⁺.

Example 47

N-hydroxy-2(R)-[7-(4-aminoihenoxy)-2,3,4,5-tetrahydrobenzor[1,2,5-f]thiadiazepine-1,1-dioxide]propanamide The material from Example 46 (110 mg, 0.26 mmol) was dissolved in MeOH prior to the addition of 5% Pd/BaSO₄ (150 mg). This solution was placed on a Parr and hydrogenated at 50 psi for 1 h. The Pd/BaSO₄ was filtered off and the solution was concentrated. This gave the title hydroxamate (36 mg): MS(AP-neg) m/e 391.2 (M−H)⁻.

Example 48

N-hydroxy-2(R)-[7-(3-methyl-4-nitrophenoxy)-2,3,4,5-tetrahydrobenzo[1,2,5-f]thiadiazepine1,1-dioxide]-propanamide.

This was produced analogously to Example 46 through the use of 5-fluoro-2-nitrotoluene: MS(ES-pos) m/e 435.1 (M−H)⁺.

Example 49

N-hydroxy-2(R)-[7-(2-nitrophenoxy)-2,3,4,5-tetrahydrobenzo[1,2,5-f]thiadiazepine1,1-dioxide]-4-methylpentanamide This was produced analogously to example 13 through the use of D-Leu-OtBu and 1-fluoro-2-nitrobenzene: MS(ES-neg) m/e 462.9 (M−H)⁻.

Example 50

N-hydroxy-2 (R)-[7-(2-aminophenoxy)-2,3,4,5-tetrahydrobenzo[1,2,5-f]thiadiazepine-1,1-dioxide]-4-methylpentanamide This was produced analogously to example 47 through the use of the above material (example 49): MS(ES-neg) m/e 432.9 (M−H)⁻

Example 51

N-hydroxy-2(R)-[7-(3-nitrophenoxy)-2,3,4,5-tetrahydrobenzo[1,2,5-f]thiadiazepine-1,1-dioxide]-propanamide 51a. The phenol from example 6F (200 mg) was dissolved in CH₂Cl₂ prior to the addition Cu(OAc)₂ (133 mg), 3-nitrobenzeneboronic acid (223 mg), powdered 4A molecular seives (480 mg), and triethylamine (0.93 mL). After 2 h, the solution was filtered and then washed with 1N HCl and 0.5N NaOH. The organic layer was concentrated. Chromatography of the resulting residue gave methyl-2(R)-[7-(3-nitrophenoxy)-2,3,4,5-tetrahydrobenzo[1,2,5-f]thiadiazepine-1,1-dioxide]-propanoate (100 mg): MS(AP-pos) m/e 422.2 (M+H)⁺.

51b. Following a procedure analogous to that in step 1d, the ester (90 mg) from above was reacted with the hydroxylamine solution (3 mL) at room temperature. After 1 h, water and EtOAc were added. The organic layer was concentrated. Chromatography of the resulting residue gave the title hydroxamate (60 mg): MS(ES-neg) m/e 421.1 (M−H)⁻.

Example 52

N-hydroxy-2 (R)-[7-phenoxy-2,3,4,5-tetrahydrobenzo[1,2,5-f]thiadiazepine-1,1-dioxide]-propanamide This was produced analogously to example 51 through the use of phenylboronic acid: MS(ES-neg) m/e 376.1 (M−H)⁻.

Example 53

N-hydroxy-2(R)-[7-(4-methylthio-phenoxy)-2,3,4,5-tetrahydrobenzo[1,2,5-f]thiadiazepine-1,1-dioxide]-propanamide This was produced analogously to example 51 through the use of 4-(methylthio)benzeneboronic acid: MS(ES-neg) m/e 422.1 (M−H)⁻

Example 54

N-hydroxy-2(R)-[7-(4-methoxyphenoxy)-2,3,4,5-tetrahydrobenzo[1,2,5-f]thiadiazeine1,1-dioxide]-propanamide This was produced analogously to example 51 through the use of 4-methoxybenzeneboronic acid: MS(ES-neg) m/e 406.1 (M−H)⁻.

Example 55

N-hydroxy-2(R)-[7-(4-trifluoromethylphenoxy)-2,3,4,5-tetrahydrobenzo[1,2,5-f]thiadiazepine1,1-dioxide]-propanamide This was produced analogously to example 51 through the use of 4-trifluoromethylbenzeneboronic acid: MS(ES-neg) m/e 444.1 (M−H)⁻.

Example 56

N-hydroxy-2(R)-[7-(4-methylsulfonylrhenoxy)-2,3,4,5-tetrahydrobenzo[1,2,5-f]thiadiazepine-1,1-dioxide]-propanamide This was produced analogously to example 53 with a subsequent MCPBA oxidation: MS(ES-neg) m/e 454.1 (M−H)⁻.

Example 57

N-hydroxy-2(R)-[7-(4-methoxycarbonylphenoxy)-2,3,4,5-tetrahydrobenzo[1,2,5-f]thiadiazepine-1,1-dioxide]-propanamide This was produced analogously to example 51 through the use of 4-methoxycarbonylbenzeneboronic acid: MS(ES-neg) m/e 434.1 (M−H)⁻.

Example 58

N-hydroxy-2(R)-[7-(4-phenylphenoxy)-2,3,4,5-tetrahydrobenzo[1,2,5-f]thiadiazepine-1,1-dioxide]-propanamide This was produced analogously to example 51 through the use of 4-phenylbenzeneboronic acid: MS(ES-neg) m/e 452.1 (M−H)⁻.

Example 59

N-hydroxy-2(R)-[7-(benzyloxy)-2,3,4,5-tetrahydro-benzo[1,2,5-f]thiadiazeiine1,1-dioxide]-2-[(5,5-dimethyl-2,4-dioxa-3-oxazolidinyl)methyl] acetamide and

Example 60

N-hydroxy-2(R)-[7-(benzyloxy)-2,3,4,5-tetrahydro-benzo[1,2,5-f]thiadiazepine1,1-dioxide]-3-N-(2-hydroxy-2-methylpropylamidyl)propylamide (59a,60a) Examples 59 and 60 were prepared in a analogous series of reactions to example 36, beginning with 5,5-dimethyloxazolidine-2,4-dione and N-trityl-D-serine methyl ester leaving out step 36b. In the step analogous to 36 g the oxazolidine-2,4-dione ring system was partially opened to give an inseperable mixture of the expected product and the dimethyl-hydroxyacetamide ring fragmented product. After the step analogous to 36h example 59 (MS, (ESI) m/e 517 (M−H)$^-$) and example 60(MS, (ESI) m/e 491 (M−H)$^-$) were isolated by C18 HPLC.

Example 61

N-hydroxy-2(R)-[7-(benzyloxy)-2,3,4,5-tetrahydro-benzo[1,2,5-f]thiadiazepine1,1-dioxide]-6-N-[(1,1-dimethylethoxy)carbonyl]hexylamide (61a) 6B (1.30 g, 3.97 mmol) in dioxane (15 mL) was added dropwise to N-ε-Boc-D-Lysine (1 g, 4.06 mmol) in 10% Na$_2$CO$_3$ (30 mL) over 10 min. Additional water (15 mL) was added to make the reaction homogeneous and the mixture was stirred vigorously overnight at room temperature. A small amount of ice was added to the reaction mixture and the pH was adjusted to ≈2 using concentrated HCl The solution was extracted with ethyl acetate (3×30 mL) and the combined extracts were washed with brine (1×30 mL) then dried over MgSO$_4$. The drying agent was filtered and the solvent removed in vacuo to afford 61a (1.75 g, 82%, MS: (ESI) m/e 560 (M+Na)$^+$) as a viscous oil.

(61b) 1,8-Diazabicyclo[5.4.0]undec-7-ene (0.50 g, 3.26 mmol) was added dropwise to 61a in benzene (1.75 g, 3.26 mmol) in benzene (50 mL) at room temperature under nitrogen. After ten minutes, methyl iodide (0.55 g, 3.91 mmol) was added and the mixture allowed to stir overnight. The reaction was diluted to 200 mL with ethyl acetate then washed with water (1×40 mL), saturated ammonium chloride (1×40 mL), saturated sodium bicarbonate (2×40 mL), and brine (1×40 mL). After drying over MgSO$_4$, the solvent was removed in vacuo and the resulting oil purified by silica gel flash chromatagraphy to afford 61b (1.24 g, 69%, MS: (ESI) m/e 574 (M+Na)$^+$) as a viscous oil.

(61c) DEAD (0.58 g, 3.32 mmol) was added dropwise at room temperature to 61b (1.22 g, 2.21 mmol), triphenylphosphine (0.89 g, 3.32 mmol), and 2-bromoethanol (0.41 g, 3.32 mmol) in benzene (20 mL). After stirring 3 h the solvent was removed in vacuo and the residue purified by flash chromatography (silica gel, 25 to 40% ethyl acetate/hexane) to provide 61c (1.25 g, 86%, MS: (ESI) m/e 680, 682 (M+Na)$^+$) as a viscous oil.

(61d) Following a procedure analogous to step 32c, 61c was treated with iron in acetic acid/water to provide 61d (MS: (ESI) m/e 650, 652 (M+Na)$^+$) as a brittle foam.

(61e) Following a procedure analogous to step 32d, 61d was treated with N-methyl morpholine in DMF to provide 61e (MS: (ESI) m/e 570 (M+Na)$^+$) as a low melting solid.

(61f) Following a procedure analogous to step 32f, 61e was treated with lithium hydroxide in THF/water to provide 61f (MS: (ESI) m/e 534 (M+H)$^+$) as viscous oil.

(61g) Following a procedure analogous to step 36h, 61f was treated with BOP reagent, hydroxylamine hydrochloride, and DIEA to provide example 61 (MS: (ESI) m/e 549 (M+H)$^+$) as a white powder.

Example 62

N-hydroxy-2(R)-[7-(3,5-dimethoxybenzyloxy)-2,3,4,5-tetrahydro-benzo[1,2,5-f]thiadiazepine1,1-dioxide]-6-N-[(1,1-dimethylethoxy)carbonyl]hexylamide (62a) Methanol (25 mL) was added carefully to 61e (732 mg, 1.39 mmol) and 10% palladium on carbon (0.30 g) under a stream of nitrogen. A balloon filled with hydrogen was attached via a three way stopcock and the atmosphere above the reaction was removed and replace with hydrogen three times. After 0.5 h the catalyst was filtered washed with methanol and the solvent was removed in vacuo. The crude product was purified by flash chromatography (silica gel, 50–70% ethyl acetate/hexane) to provide 62a (586 mg, 95%, MS: (ESI) m/e 458 (M+H)$^+$) as a clear oil.

(62b) Cesium carbonate (0.83 g, 2.56 mmol) was added in one portion to 62a (586 mg, 1.28 mmol), sodium iodide (0.19 g, 1.28 mmol), and 3,5-dimethoxybenzylchloride (0.29 g, 1.54 mmol) in DMF (10 mL) at room temperature. After 3 h the reactin was quenched with saturated ammonium chloride the extracted with ether (3×). The combined organic extracts were washed with water (2×), saturated NaHCO$_3$ (1×), and brine (1×) then dried over MgSO$_4$. After filtration the solvent was removed in vacuo and the residue purified by flash chromatography (silica gel) to afford 62b (701 mg, 90%, MS: (ESI) m/e 608 (M+H)$^+$) as a viscous oil.

(62c) Following a procedure analogous to step 32f, 62b was treated with lithium hydroxide in THF/water to provide 62c (MS: (ESI) m/e 594 (M+H)$^+$) as viscous oil.

(62d) Following a procedure analogous to step 36h, 62c was treated with BOP reagent, hydroxylamine hydrochloride, and DIEA to provide example 62 (MS: (ESI) m/e 609 (M+H)$^+$) as a white powder.

Example 63

N-hydroxy-2(R)-[7-(3,5-dimethoxybenzyloxy)-2,3,4,5-tetrahydro-benzo[1,2,5-f]thiadiazepine1,1-dioxide]-6-amino-hexylamide Trifluoroacetic Acid Salt (63a) Trifluoroacetic acid (1 mL) was added to example 62 (20 mg, 0.033 mmol) in methylene chloride (1 mL) at room temperature. After 20 min the solvent was removed in vacuo then chloroform was added (3 mL) and removed in vacuo (3×). The residue was taken up in water (2 mL) and frozen and the water remove under high vacuum to afford example 63 (MS: (ESI) m/e 509 (M+H)$^+$) as a white powder.

Example 64

N-hydroxy-2(R)-[7-(3,5-dimethoxybenzyloxy)-2,3,4,5-tetrahydro-benzo[1,2,5-f]thiadiazepine1,1-dioxide]-6-N-(acetamidyl)-hexylamide (64a) Trifluoroacetic acid (1 mL) was added to 62b (72 mg, 0.033 mmol) in methylene chloride (1 mL) at room temperature. After 20 min the solvent was removed in vacuo then chloroform was added (3 mL) and removed in vacuo (3x). The residue 64a was taken forward without any further purification (MS: (ESI) m/e 508 (M+H)$^+$).

(64b) Acetyl chloride (11 mg, 0.14 mmol) was added to 62b and triethylamine (60 mg, 0.59 mmol) in dry methylene chloride (2 mL) at room temperature under nitrogen. The reactin was stirred 4 h the quenched with saturated ammonium chloride, the extracted with ethyl acetate(3x). The combined organic extracts were washed with brine (1x) then dried over MgSO$_4$. After filtration the solvent was removed in vacuo and the residue purified by flash chromatography (silica gel) to afford 64b (23 mg, 33%, MS: (ESI) m/e 550 (M+H)$^+$).

(64c) Following a procedure analogous to step 32f, 64b was treated with lithium hydroxide in THF/water to provide 64c (MS: (ESI) m/e 534 (M−H)$^-$).

(64d) Following a procedure analogous to step 36h, 64c was treated with BOP reagent, hydroxylamine hydrochloride, and DIEA to provide example 64 (MS: (ESI) m/e 551 (M+H)$^+$) as a white powder.

Example 65

N-hydroxy-2(R)-[7-(3,5-dimethoxybenzyloxy)-2,3,4, 5-tetrahydro-benzo[1,2,5-f]thiadiazepine1,1-dioxide]-6-N-(methanesulfonyl)-hexylamide Example 65 was prepared in a analogous series of reactions to example 64, beginning with 64b and methanesulfonyl chloride (MS, (ESI) m/e 587 (M+Na)$^+$).

Example 66

N-hydroxy-2(R)-[7-(2,6-dimethoxypyridyl-4-methyleneoxy)-2,3,4,5-tetrahydro-benzo[1,2,5-f]thiadiazepine1,1-dioxide]-6-N-[(1,1-dimethylethoxy)carbonyl]hexylamide Example 66 was prepared in a analogous series of reactions to example 62, beginning with 62b and 4-chloromethyl-2,6-dimethoxypyridine (MS, (ESI) m/e 610 (M+H)$^+$).

Example 67

N-hydroxy-2(R)-[7-(2,6-dimethoxypyridyl-4-methyleneoxy)-2,3,4,5-tetrahydro-benzo[1,2,5-f]thiadiazepine1,1-dioxide]-6-aminohexylamide trifluoroacetic acid salt (67a) Following a procedure analogous to step 63a, example 66 was treated with trifluoroacetic acid in methylene chloride to provide example 67 (MS: (ESI) m/e 510 (M+H)$^+$) as a white powder.

Example 68

N-hydroxy-2(R)-[7-(3,5-dimethoxybenzyloxy)-2,3,4, 5-tetrahydro-benzo[1,2,5-f]thiadiazepine1,1-dioxide]-6-N-(benzenesulfonyl)-hexylamide Example 68 was prepared in a analogous series of reactions to example 64, beginning with 64b and benzenesulfonyl chloride (MS, (ESI) m/e 649 (M+H)$^+$).

Example 69

N-hydroxy-2(R)-[7-(3,5-dimethoxybenzyloxy)-2,3,4, 5-tetrahydro-benzo[1,2,5-f]thiadiazepine1,1-dioxide]-6-N-(butylsulfonyl)-hexylamide Example 69 was prepared in a analogous series of reactions to example 64, beginning with 64b and n-butylsulfonyl chloride (MS, (ESI) m/e 629 (M+H)$^+$).

Example 70

N-hydroxy-2(R)-[7-(3,5-dimethoxybenzyloxy)-2,3,4, 5-tetrahydro-benzo[1,2,5-f]thiadiazepine1,1-dioxide]-6-N-[(3,5-dimethyl-4-isoxazolyl)sulfonyl]-hexylamide Example 70 was prepared in a analogous series of reactions to example 64, beginning with 64b and 3,5-Dimethyl-4-isoxazolylsulfonyl chloride (MS, (ESI) m/e 666 (M−H)$^-$).

Example 71

N-hydroxy-2(R)-[7-(3,5-dimethoxybenzyloxy)-2,3,4, 5-tetrahydro-benzo[1,2,5-f]thiadiazepine1,1-dioxide]-6-N-[(5-chloro-1,3-dimethyl-1H-pyrazol-4-yl)sulfonyl]-hexylamide Example 71 was prepared in a analogous series of reactions to example 64, beginning with 64b 5-Chloro-1,3-dimethyl-4-pyrazolesulfonyl chloride (MS, (ESI) m/e 699, 701 (M−H)$^-$).

Example 72

N-hydroxy-2(R)-[7-phenyl-2,3,4,5-tetrahydro-benzo[1,2,5-f]thiadiazepine1,1-dioxide]propylamide (72a) Trifluromethanesufonic anhydride (48 mg, 0.17 mmol) was added to 6f (51 mg, 0.17 mmol) and DIEA (66 mg, 0.51 mmol) in methylene chloride (5 mL) at −78° C. under nitrogen. The reaction was stirred 2.5 h and was quenched at −78° C. by the addition of saturated ammonium chloride. After warming to room temperature the solution was extracted with methylene chloride (3x) and the combined extracts were washed with brine (1x) then dried over MgSO$_4$. After filtration the solvent was removed in vacuo and the residue purified by flash chromatography (silica gel) to afford 72a (47 mg, 64%, MS: (ESI) m/e 433 (M+H)$^+$).

(72b) Palladium acetate (5 mg, 0.022 mmol) was added to 72a (47 mg, 0.11 mmol), phenylboronic acid (27 mg, 0.22 mmol), tripheylphosphine (28 mg, 0.11 mmol), and potassium carbonate (60 mg, 0.43 mmol) in degassed toluene (10 mL) under nitrogen. The reaction was heated to reflux for 45 min then cooled to room temperature. Water (10 mL) was added and the mixture was extracted with ethyl acetate (3x). The combined extracts were washed with water (1x), 10% citric acid (1x), saturated NaHCO$_3$ (1x), and brine (1x) then dried over MgSO$_4$. After filtration the solvent was removed in vacuo and the residue purified by flash chromatography (silica gel) to afford 72b (25 mg, 64%, MS: (ESI) m/e 361 (M+H)$^+$).

(72c) Following a procedure analogous to step 32f, 72b was treated with lithium hydroxide in THF/water to provide 72c (MS: (ESI) m/e 345 (M−H)$^-$).

(72d) Following a procedure analogous to step 36h, 64c was treated with BOP reagent, hydroxylamine hydrochloride, and DIEA to provide example 72 (MS: (ESI) m/e 362 (M+H)$^+$) as a white powder.

Example 73

N-hydroxy-2(R)-[7-(2-trifluoromethylphenyl)-2,3,4, 5-tetrahydro-benzo[1,2,5-f]thiadiazepine1,1-dioxide]propylamide Example 73 was prepared in a analogous series of reactions to example 72, beginning with 72a and 2-trifluoromethylphenylboronic acid (MS, (ESI) m/e 430 (M+H)$^+$).

Example 74

N-hydroxy-2(R)-[7-(phenylethynyl)-2,3,4,5-tetrahydro-benzo[1,2,5-f]thiadiazemine 1,1-dioxide] propylamide (74a) Dichlorobis(tripheylphosphine)palladium(II) (11 mg, 0.115 mmol), phenylacetylene (46 mg, 0.45 mmol), and 72a (65 mg 0.15 mmol) was taken up in degassed DMF/triethylamine (4/1, 5 mL) and heated to 90° C. under nitrogen. After 2 h the reaction was cooled to room temperature and diluted to 40 mol with ethyl acetate. The solution was washed with water (2×), saturated NaHCO3 (2×), and brine (1×) then dried over MgSO$_4$. After filtration the solvent was removed in vacuo and the residue purified by flash chromatography (silica gel) to afford 74a (52 mg, 90%, MS: (ESI) m/e 385 (M+H)$^+$).

(74b) Following a procedure analogous to step 32f, 74a was treated with lithium hydroxide in THF/water to provide 74b (MS: (ESI) m/e 371 (M+H)$^+$).

(72c) Following a procedure analogous to step 36h, 74b was treated with BOP reagent, hydroxylamine hydrochloride, and DIEA to provide example 74 (MS: (ESI) m/e 386 (M+H)$^+$) as a white powder.

Example 75

N-hydroxy-2(R)-[7-(4-biphenylyl)-2,3,4,5-tetrahydro-benzo[1,2,5-f]thiadiazepine1,1-dioxide] propylamide Example 75 was prepared in a analogous series of reactions to example 72, beginning with 72a and biphenylboronic acid (MS, (ESI) m/e 438 (M+H)$^+$).

TABLE 1

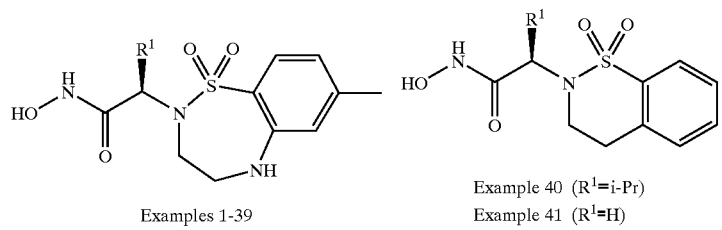

Examples 1-39

Example 40 (R$^1$=i-Pr)
Example 41 (R$^1$=H)

| Ex # | R$^1$ | R$^3$ | MS (M − H)$^-$ |
|---|---|---|---|
| 1 | H | H | 256 [M − O + H]$^+$ |
| 2 | H | methoxy | 300 |
| 3 | methyl | H | 284 |
| 4 | methyl | methoxy | 314 |
| 5 | isopropyl | methoxy | 342 |
| 6 | methyl | (3,5-dimethylphenyl)methoxy | 418 |
| 7 | methyl | (3,5-dichlorophenyl)methoxy | 458 |
| 8 | methyl | (3,5-dimethoxyphenyl)methoxy | 450 |
| 9 | methyl | (3,5-dibromophenyl)methoxy | 550 |
| 10 | methyl | (3,5-diethoxyphenyl)methoxy | 480 |
| 11 | methyl | (3,5-dichloro-4-pyridinyl)methoxy | 459 |
| 12 | methyl | (3-amino-5-methylphenyl)methoxy | 419 |
| 13 | isopropyl | (3,5-dimethylphenyl)methoxy | 446 |
| 14 | isopropyl | (3,5-dimethoxyphenyl)methoxy | 478 |
| 15 | isopropyl | (3,5-diethoxyphenyl)methoxy | 506 |
| 16 | isopropyl | (4,5-dimethyl-2-thiazolyl)methoxy | 453 |
| 17 | isobutyl | (3,5-dimethylphenyl)methoxy | 460 |
| 18 | isobutyl | (3,5-dibromophenyl)methoxy | 575 |
| 19 | isobutyl | 2-nitrophenoxy | 463 |
| 20 | isobutyl | 2-aminophenoxy | 433 |
| 21 | isobutyl | (3,5-dichloro-4-pyridinyl)methoxy | 503 |
| 22 | isobutyl | (4-pyridinyl)methoxy | 433 |
| 23 | isobutyl | (3,5-dichlorophenyl)methoxy | 500 |
| 24 | isobutyl | (3,5-dimethoxyphenyl)methoxy | 492 |
| 25 | 3-methoxy-3-oxopropyl | (3,5-diethoxyphenyl)methoxy | 550 |
| 26 | 3-methoxy-3-oxopropyl | (3,5-dimethoxyphenyl)methoxy | 522 |
| 27 | isobutyl | amino | 341 |
| 28 | isobutyl | acetylamino | 383 |
| 29 | isobutyl | phenylacetylamino | 459 |
| 30 | isobutyl | H | 350 [M + Na]$^+$ |
| 31 | isobutyl | (3,5-dimethoxy-phenyl)methylamino | 515 [M + Na]$^+$ |
| 32 | methyl | (3,5-dimethyl-phenyl)methylamino | 441 [M + Na]$^+$ |
| 33 | methyl | benzoylamino | 427 [M + Na]$^+$ |

TABLE 1-continued

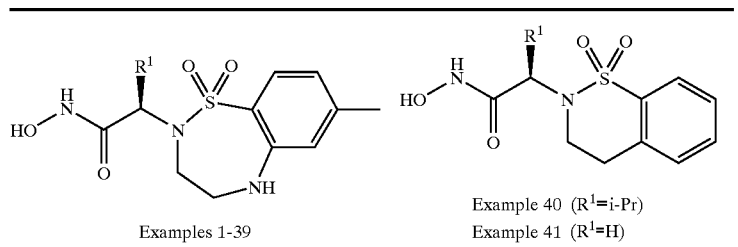

Examples 1-39

Example 40 (R$^1$=i-Pr)
Example 41 (R$^1$=H)

| Ex # | R$^1$ | R$^3$ | MS (M − H)$^-$ |
|---|---|---|---|
| 34 | methyl | 3,5-dimethoxybenzoylamino | 487 [M + Na]$^+$ |
| 35 | methyl | 3,5-dimethylbenzoylamino | 455 [M + Na]$^+$ |
| 36 | (3,4,4-trimethyl-2,5-dioxa-1-imidazolidinyl)methyl | benzyloxy | 554 [M + Na]$^+$ |
| 37 | (3,4,4-trimethyl-2,5-dioxa-1-imidazolidinyl)methyl | (3,5-dimethoxyphenyl)methoxy | 614 [M + Na]$^+$ |
| 38 | (3,4,4-trimethyl-2,5-dioxa-1-imidazolidinyl)methyl | (3,5-dimethylphenyl)methoxy | 582 [M + Na]$^+$ |
| 39 | (3,4,4-trimethyl-2,5-dioxa-1-imidazolidinyl)methyl | (3,5-dibromophenyl)methoxy | 712 [M + Na]$^+$ |
| 40 | see structure above | | 273 [M + NH$_4$]$^+$ |
| 41 | see structure above | | 229 [M + H]$^+$ |
| 42 | 4-methoxy-4-oxobutyl | (3,5-dimethoxyphenyl)methoxy | 538 [M + H]$^+$ |
| 43 | 4-methoxy-4-oxobutyl | (3,5-diethoxyphenyl)methoxy | 566 [M + H]$^+$ |
| 44 | 5-methoxy-5-oxopentyl | (3,5-dimethoxyphenyl)methoxy | 550 |
| 45 | 5-hydroxy-5-oxopentyl | (3,5-dimethoxyphenyl)methoxy | 536 |
| 46 | methyl | 4-nitrophenoxy | 423 [M + H]$^+$ |
| 47 | methyl | 4-aminophenoxy | 391 |
| 48 | methyl | 3-methyl-4-nitrophenoxy | 435 [M + H]$^+$ |
| 49 | isobutyl | 2-nitrophenoxy | 463 |
| 50 | isobutyl | 2-aminophenoxy | 433 |
| 51 | methyl | 3-nitrophenoxy | 421 |
| 52 | methyl | phenoxy | 376 |
| 53 | methyl | 4-(methylthio)phenoxy | 422 |
| 54 | methyl | 4-methoxyphenoxy | 406 |
| 55 | methyl | 4-(trifluoromethyl)phenoxy | 444 |
| 56 | methyl | 4-(methylsulfonyl)phenoxy | 454 |
| 57 | methyl | 4-(1-methoxy-1-oxomethyl)phenoxy | 434 |
| 58 | methyl | 4-phenylphenoxy | 454 |
| 59 | 5,5-dimethyl-2,4-dioxo-3-oxazolidinyl)methyl | benzyloxy | 517 |
| 60 | (2-hydroxy-2-methyl-propylamidyl)methyl | benzyloxy | 491 |
| 61 | 4-[[(1,1-dimethyl-ethoxy)carbonyl]amino]butyl | benzyloxy | 549 [M + H]$^+$ |
| 62 | 4-[[(1,1-dimethyl-ethoxy)carbonyl]amino]butyl | (3,5-dimethoxyphenyl)methoxy | 609 [M + H]$^+$ |
| 63 | 4-aminobutyl | (3,5-dimethoxyphenyl)methoxy | 509 [M + H]$^+$ |
| 64 | 4-(acetylamino)butyl | (3,5-dimethoxyphenyl)methoxy | 551 [M + H]$^+$ |
| 65 | 4-[(methylsulfonyl)amino]butyl | (3,5-dimethoxyphenyl)methoxy | 587 [M + H]$^+$ |
| 66 | 4-[[(1,1-dimethylethoxy)carbonyl]amino]butyl | (3,5-dimethoxyphenyl)methoxy | 610 [M + H]$^+$ |
| 67 | 4-aminobutyl | (3,5-dimethoxyphenyl)methoxy | 510 [M + H]$^+$ |
| 68 | 4-[(phenylsulfonyl)amino]butyl | (3,5-dimethoxyphenyl)methoxy | 649 [M + H]$^+$ |
| 69 | 4-[(butylsulfonyl)amino]butyl | (3,5-dimethoxyphenyl)methoxy | 629 [M + H]$^+$ |
| 70 | 4-(3,5-dimethyl-4-isoxazolyl)sulfonyl]butyl | (3,5-dimethoxyphenyl)methoxy | 666 |
| 71 | 4-[(5-chloro-1,3-dimethyl-1H-pyrazol-4- | (3,5-dimethoxyphenyl)methoxy | 699 |

TABLE 1-continued

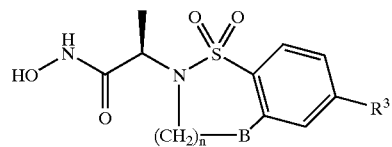

Examples 1-39

Example 40 (R¹=i-Pr)
Example 41 (R¹=H)

| Ex # | R¹ | R³ | MS (M − H)⁻ |
|---|---|---|---|
| | yl)sulfonyl]butyl | | |
| 72 | methyl | phenyl | 362 [M + H]⁺ |
| 73 | methyl | 2-(trifluoromethyl)phenyl | 430 [M + H]⁺ |
| 74 | methyl | 2-phenylethynyl | 386 [M + H]⁺ |
| 75 | methyl | 4-phenylphenyl | 438 [M + H]⁺ |

The following tables contain representative examples of the present invention. Each entry in each table is intended to be paired with each formula at the start of the table. For example, in Table 2, example 1 is intended to be paired with of formulae A1–09.

TABLE 2

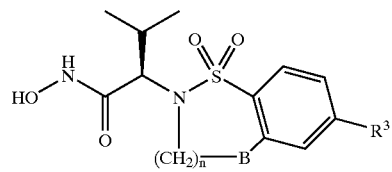

A1 (n=0, B=CH₂)
A2 (n=1, B=CH₂)
A3 (n=1, B=NH)
A4 (n=1, B=O)
A5 (n=1, B=S)
A6 (n=2, B=CH₂)
A7 (n=2, B=NH)
A8 (n=2, B=O)
A9 (n=2, B=S)

B1 (n=0, B=CH₂)
B2 (n=1, B=CH₂)
B3 (n=1, B=NH)
B4 (n=1, B=O)
B5 (n=1, B=S)
B6 (n=2, B=CH₂)
B7 (n=2, B=NH)
B8 (n=2, B=O)
B9 (n=2, B=S)

TABLE 2-continued

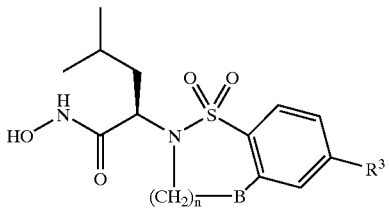

C1 (n=0, B=CH₂)
C2 (n=1, B=CH₂)
C3 (n=1, B=NH)
C4 (n=1, B=O)
C5 (n=1, B=S)
C6 (n=2, B=CH₂)
C7 (n=2, B=NH)
C8 (n=2, B=O)
C9 (n=2, B=S)

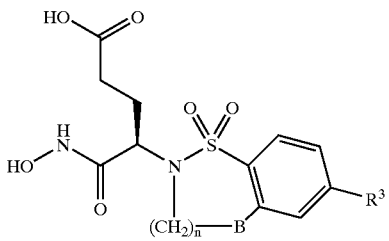

D1 (n=0, B=CH₂)
D2 (n=1, B=CH₂)
D3 (n=1, B=NH)
D4 (n=1, B=O)
D5 (n=1, B=S)
D6 (n=2, B=CH₂)
D7 (n=2, B=NH)
D8 (n=2, B=O)
D9 (n=2, B=S)

TABLE 2-continued

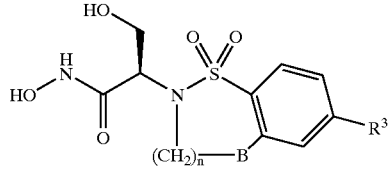

E1 (n=0, B=CH₂)
E2 (n=1, B=CH₂)
E3 (n=1, B=NH)
E4 (n=1, B=O)
E5 (n=1, B=S)
E6 (n=2, B=CH₂)
E7 (n=2, B=NH)
E8 (n=2, B=O)
E9 (n=2, B=S)

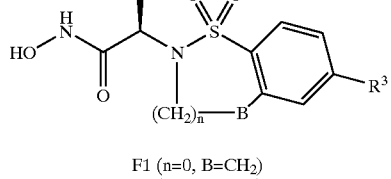

F1 (n=0, B=CH₂)
F2 (n=1, B=CH₂)
F3 (n=1, B=NH)
F4 (n=1, B=O)
F5 (n=1, B=S)
F6 (n=2, B=CH₂)
F7 (n=2, B=NH)
F8 (n=2, B=O)
F9 (n=2, B=S)

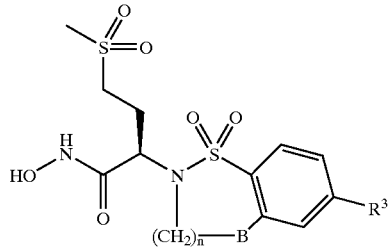

G1 (n=0, B=CH₂)
G2 (n=1, B=CH₂)
G3 (n=1, B=NH)
G4 (n=1, B=O)
G5 (n=1, B=S)
G6 (n=2, B=CH₂)
G7 (n=2, B=NH)
G8 (n=2, B=O)
G9 (n=2, B=S)

TABLE 2-continued

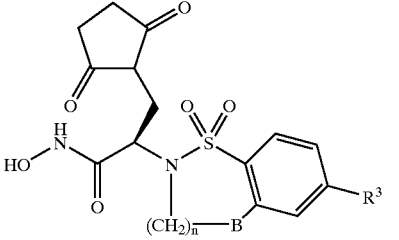

H1 (n=0, B=CH₂)
H2 (n=1, B=CH₂)
H3 (n=1, B=NH)
H4 (n=1, B=O)
H5 (n=1, B=S)
H6 (n=2, B=CH₂)
H7 (n=2, B=NH)
H8 (n=2, B=O)
H9 (n=2, B=S)

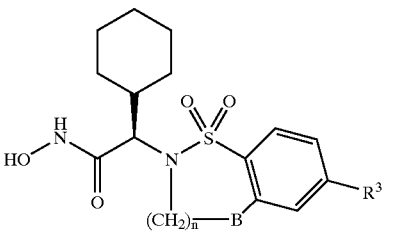

I1 (n=0, B=CH₂)
I2 (n=1, B=CH₂)
I3 (n=1, B=NH)
I4 (n=1, B=O)
I5 (n=1, B=S)
I6 (n=2, B=CH₂)
I7 (n=2, B=NH)
I8 (n=2, B=O)
I9 (n=2, B=S)

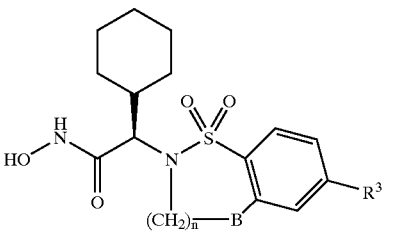

J1 (n=0, B=CH₂)
J2 (n=1, B=CH₂)
J3 (n=1, B=NH)
J4 (n=1, B=O)
J5 (n=1, B=S)
J6 (n=2, B=CH₂)
J7 (n=2, B=NH)
J8 (n=2, B=O)
J9 (n=2, B=S)

TABLE 2-continued

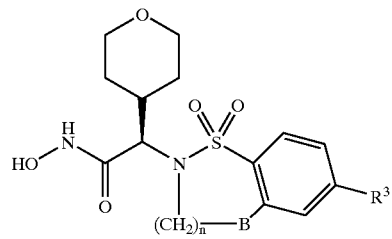

K1 (n=0, B=CH$_2$)
K2 (n=1, B=CH$_2$)
K3 (n=1, B=NH)
K4 (n=1, B=O)
K5 (n=1, B=S)
K6 (n=2, B=CH$_2$)
K7 (n=2, B=NH)
K8 (n=2, B=O)
K9 (n=2, B=S)

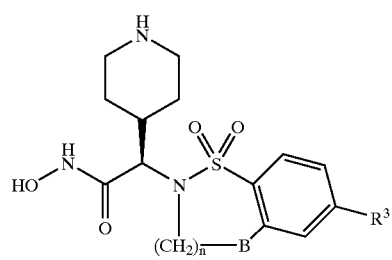

L1 (n=0, B=CH$_2$)
L2 (n=1, B=CH$_2$)
L3 (n=1, B=NH)
L4 (n=1, B=O)
L5 (n=1, B=S)
L6 (n=2, B=CH$_2$)
L7 (n=2, B=NH)
L8 (n=2, B=O)
L9 (n=2, B=S)

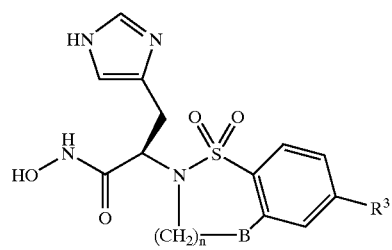

M1 (n=0, B=CH$_2$)
M2 (n=1, B=CH$_2$)
M3 (n=1, B=NH)
M4 (n=1, B=O)
M5 (n=1, B=S)
M6 (n=2, B=CH$_2$)
M7 (n=2, B=NH)
M8 (n=2, B=O)
M9 (n=2, B=S)

TABLE 2-continued

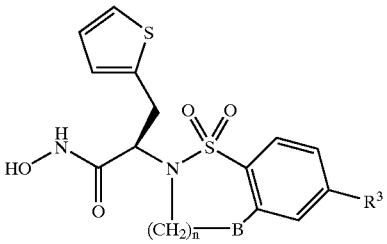

N1 (n=0, B=CH$_2$)
N2 (n=1, B=CH$_2$)
N3 (n=1, B=NH)
N4 (n=1, B=O)
N5 (n=1, B=S)
N6 (n=2, B=CH$_2$)
N7 (n=2, B=NH)
N8 (n=2, B=O)
N9 (n=2, B=S)

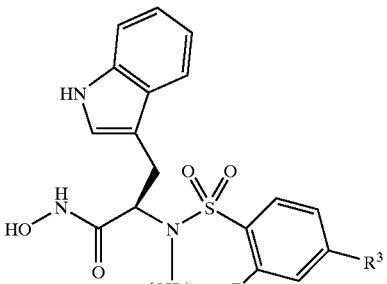

O1 (n=0, B=CH$_2$)
O2 (n=1, B=CH$_2$)
O3 (n=1, B=NH)
O4 (n=1, B=O)
O5 (n=1, B=S)
O6 (n=2, B=CH$_2$)
O7 (n=2, B=NH)
O8 (n=2, B=O)
O9 (n=2, B=S)

| Ex # | R$^3$ |
|---|---|
| 1 | H |
| 2 | methyl |
| 3 | methoxy |
| 4 | 1-methylethyl |
| 5 | 1-methylethoxy |
| 6 | phenyl |
| 7 | [1,1'-biphenyl]-4-yl |
| 8 | phenoxy |
| 9 | 2-phenylethyl |
| 10 | 2-(3,5-dimethylphenyl)ethyl |
| 11 | 1-(2,6-dimethylphenyl)ethyl |
| 12 | 2-phenylethenyl |
| 13 | phenoxymethyl |
| 14 | (2-methylphenyl)methoxy |
| 15 | (3-methylphenyl)methoxy |
| 16 | 3-methylphenoxy |
| 17 | 2,6-dimethylphenoxy |
| 18 | (2,6-dimethylphenyl)methoxy |
| 19 | 3,5-dimethylphenoxy |
| 20 | (3,5-dimethylphenyl)methoxy |
| 21 | 2-(3,5-dimethylphenyl)ethyl |
| 22 | 2-(3,5-dimethylphenyl)ethenyl |
| 23 | (3-amino-5-methylphenyl)methoxy |
| 24 | (2-amino-6-methylphenyl)methoxy |
| 25 | (3-cyano-5-methylphenyl)methoxy |
| 26 | (3-cyano-5-methylphenoxy)methyl |
| 27 | (3-cyano-5-nitrophenyl)methoxy |
| 28 | (3,5-diethoxyphenyl)methoxy |

TABLE 2-continued

| | |
|---|---|
| 29 | (3,5-dimethoxyphenyl)methoxy |
| 30 | 3,5-dimethoxyphenoxy |
| 31 | 2-(3,5-dimethoxyphenyl)ethyl |
| 32 | 1-(3,5-dimethoxyphenyl)ethoxy |
| 33 | (3,5-dichlorophenyl)methoxy |
| 34 | (2,6-dichlorophenyl)methoxy |
| 35 | (3,5-dibromophenyl)methoxy |
| 36 | 3,5-dibromophenoxy |
| 37 | (3-amino-5-cyanophenyl)methoxy |
| 38 | [2,6-bis(trifluoromethyl)phenyl]methoxy |
| 39 | 2,6-bis(trifluoromethyl)phenoxy |
| 40 | (3-aminocarbonyl-5-methylphenyl)methoxy |
| 41 | ([1,1'-biphenyl]-2-yl)methoxy |
| 42 | ([1,1'-biphenyl]-3-yl)methoxy |
| 43 | [5-methyl-3-(methylsulfonyl)phenyl]methoxy |
| 44 | 5-methyl-3-(methylsulfonyl)phenoxy |
| 45 | (2-pyridinyl)methoxy |
| 46 | (4-pyridinyl)methoxy |
| 47 | (2,6-dimethyl-4-pyridinyl)methoxy |
| 48 | 2,6-dimethyl-4-pyridinyloxy |
| 49 | 1-(2,6-dimethyl-4-pyridinyl)ethoxy |
| 50 | (3,5-dimethyl-4-pyridinyl)methoxy |
| 51 | (2,6-diethyl-4-pyridinyl)methoxy |
| 52 | (2,6-dichloro-4-pyridinyl)methoxy |
| 53 | (2,6-dimethoxy-4-pyridinyl)methoxy |
| 54 | (2-chloro-6-methyl-4-pyridinyl)methoxy |
| 55 | (2-chloro-6-methoxy-4-pyridinyl)methoxy |
| 56 | (2-methoxy-6-methyl-4-pyridinyl)methoxy |
| 57 | (1-naphthalenyl)methoxy |
| 58 | 1-naphthalenyloxy |
| 59 | (2-naphthalenyl)methoxy |
| 60 | (2-methyl-1-naphthalenyl)methoxy |
| 61 | (4-methyl-2-naphthalenyl)methoxy |
| 62 | (4-quinolinyl)methoxy |
| 63 | 1-(4-quinolinyl)ethoxy |
| 64 | 4-quinolinyloxy |
| 65 | (4-quinolinyloxy)methyl |
| 66 | 2-(4-quinolinyl)ethyl |
| 67 | (2-methyl-4-quinolinyl)ethoxy |
| 68 | 2-methyl-4-quinolinyloxy |
| 69 | (2-chloro-4-quinolinyl)methoxy |
| 70 | (2-methoxy-4-quinolinyl)methoxy |
| 71 | (2-hydroxy-4-quinolinyl)methoxy |
| 72 | (2-trifluoromethyl-4-quinolinyl)methoxy |
| 73 | (2-phenyl-4-quinolinyl)methoxy |
| 74 | (2,6-dimethyl-4-quinolinyl)methoxy |
| 75 | (2,7-dimethyl-4-quinolinyl)methoxy |
| 76 | (5-quinolinyl)methoxy |
| 77 | (7-methyl-5-quinolinyl)methoxy |
| 78 | (7-methoxy-5-quinolinyl)methoxy |
| 79 | (8-quinolinyl)methoxy |
| 80 | 2-(1,2,3-benzotriazol-1-yl)ethyl |
| 81 | (2-benzimidazolyl)methoxy |
| 82 | (1,4-dimethyl-5-imidazolyl)methoxy |
| 83 | (3,5-dimethyl-4-isoxazolyl)methoxy |
| 84 | (4,5-dimethyl-2-oxazolyl)methoxy |
| 85 | (2,5-dimethyl-4-thiazolyl)methoxy |
| 86 | (3,5-dimethyl-1-pyrazolyl)ethyl |
| 87 | (1,3-benzodioxo-4-yl)methoxy |
| 88 | (1,3,5-trimethyl-4-pyrazolyl)methoxy |
| 89 | (2,6-dimethyl-4-pyrimidinyl)methoxy |
| 90 | (4,5-dimethyl-2-furanyl)methoxy |
| 91 | (4,5-dimethyl-2-thiazolyl)methoxy |
| 92 | 2-(2-oxazolyl)ethyl |

Utility

The compounds of formula I are expected to possess matrix metalloproteinase and/or aggrecanase and/or TNF inhibitory activity. The MMP-3 inhibitory activity of the compounds of the present invention is demonstrated using assays of MMP-3 activity, for example, using the assay described below for assaying inhibitors of MMP-3 activity. The compounds of the present invention are expected to be bioavailable in vivo as demonstrated, for example, using the ex vivo assay described below. The compounds of formula I are expected to have the ability to suppress/inhibit cartilage degradation in vivo, for example, as demonstrated using the animal model of acute cartilage degradation described below.

The compounds provided by this invention should also be useful as standards and reagents in determining the ability of a potential pharmaceutical to inhibit MPs. These would be provided in commercial kits comprising a compound of this invention.

Metalloproteinases have also been implicated in the degradation of basement membranes to allow infiltration of cancer cells into the circulation and subsequent penetration into other tissues leading to tumor metastasis. (Stetler-Stevenson, Cancer and Metastasis Reviews, 9, 289–303, 1990.) The compounds of the present invention should be useful for the prevention and treatment of invasive tumors by inhibition of this aspect of metastasis.

The compounds of the present invention should also have utility for the prevention and treatment of osteopenia associated with matrix metalloproteinase-mediated breakdown of cartilage and bone which occurs in osteoporosis patients.

Compounds which inhibit the production or action of TNF and/or Aggrecanase and/or MP's are potentially useful for the treatment or prophylaxis of various inflammatory, infectious, immunological or malignant diseases. These include, but are not limited to inflammation, fever, cardiovascular effects, hemorrhage, coagulation and acute phase response, an acute infection, septic shock, haemodynamic shock and sepsis syndrome, post ischaemic reperfusion injury, malaria, Crohn's disease, mycobacterial infection, meningitis, psoriasis, periodontits, gingivitis, congestive heart failure, fibrotic disease, cachexia, and aneroxia, graft rejection, cancer, corneal ulceration or tumor invasion by secondary metastases, autoimmune disease, skin inflammatory diseases, multiple osteo and rheumatoid arthritis, multiple sclerosis, radiation damage, HIV, and hyperoxic alveolar injury.

Some compounds of the present invention have been shown to inhibit TNF production in lipopolysacharride stimulated mice, for example, using the assay for TNF Induction in Mice and in human whole blood as described below.

Some compounds of the present invention have been shown to inhibit aggrecanase a key enzyme in cartilage breakdown as determined by the aggrecanase assay described below.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar and "nm" denotes nanometer. "Sigma" stands for the Sigma-Aldrich Corp. of St. Louis, Mo.

A compound is considered to be active if it has an $IC_{50}$ $K_i$ value of less than about 1 mM for the inhibition of MMP-3.

Aggrecanase Enzymatic Assay

A novel enzymatic assay was developed to detect potential inhibitors of aggrecanase. The assay uses active aggrecanase accumulated in media from stimulated bovine nasal cartilage (BNC) or related cartilage sources and purified cartilage aggrecan monomer or a fragment thereof as a substrate.

The substrate concentration, amount of aggrecanase, time of incubation and amount of product loaded for Western analysis were optimized for use of this assay in screening putative aggrecanase inhibitors. Aggrecanase is generated by stimulation of cartilage slices with interleukin-1 (IL-1), tumor necrosis factor alpha (TNFα) or other stimuli. Matrix metalloproteinases (MMPs) are secreted from cartilage in an inactive, zymogen form following stimulation, although active enzymes are present within the matrix. We have shown that following depletion of the extracellular aggrecan matrix, active MMPs are released into the culture media. (Tortorella, M. D. et. al. Trans. Ortho. Res. Soc. 20, 341, 1995). Therefore, in order to accumulate BNC aggrecanase in culture media, cartilage is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. In order to decrease the amounts of other matrix metalloproteinases released into the media during aggrecanase accumulation, agents which inhibit MMP-1, -2, -3, and -9 biosynthesis are included during stimulation. This BNC conditioned media, containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, CE, et al., Biochem J 306:799–804, 1995). This antibody recognizes aggrecan fragments with the N-terminus, 374ARGSVIL, generated upon cleavage by aggrecanase. The BC-3 antibody recognizes this neoepitope only when it is at the N-terminus and not when it is present internally within aggrecan fragments or within the aggrecan protein core. Other proteases produced by cartilage in response to IL-1 do not cleave aggrecan at the Glu373-Ala374 aggrecanase site; therefore, only products produced upon cleavage by aggrecanase are detected. Kinetic studies using this assay yield a Km of 1.5+/−0.35 uM for aggrecanase.

To evaluate inhibition of aggrecanase, compounds are prepared as 10 mM stocks in DMSO, water or other solvents and diluted to appropriate concentrations in water. Drug (50 ul) is added to 50 ul of aggrecanase-containing media and 50 ul of 2 mg/ml aggrecan substrate and brought to a final volume of 200 ul in 0.2 M Tris, pH 7.6, containing 0.4 M NaCl and 40 mM $CaCl_2$. The assay is run for 4 hr at 37° C., quenched with 20 mM EDTA and analyzed for aggrecanase-generated products. A sample containing enzyme and substrate without drug is included as a positive control and enzyme incubated in the absence of substrate serves as a measure of background.

Removal of the glycosaminoglycan side chains from aggrecan is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 ug GAG) for 2 hr at 37° C. and then with keratanase (0.1 units/10 ug GAG) and keratanase II (0.002 units/10 ug GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 ul of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

MMP Screens

The enzymatic activities of recombinant MMP-1, 3 and 9 were measured at 25° C. with a fluorometric assay (Copeland, R. A.; Lombardo, D.; Giannaras, J. and Decicco, C. P. Bioorganic Med. Chem. Lett. 1995, 5, 1947–1952). Final enzyme concentrations in the assay were between 0.05 and 10 nM depending on the enzyme and the potency of the inhibitor tested. The permisive peptide substrate, MCA-Pro-Leu-Gly-Leu-DPA-Ala-Arg-$NH_2$, was present at a final concentration of 10 uM in all assays. Initial velocities, in the presence or absence of inhibitor, were measured as slopes of the linear portion of the product progress curves. IC50 values were determined by plotting the inhibitor concentration dependence of the fractional velocity for each enzyme, and fitting the data by non-linear least squares methods to the standard isotherm equation (Copeland, R. A. Enzymes: A practical Introduction to Structure, Mechanism and Data Analysis, Wiley-VHC, New York, 1996, pp 187–223). All of the hydroxamic acids studied here were assumed to act as competitive inhibitors of the enzyme, binding to the active site Zn atom as previously demonstrated by crystallographic studies of MMP-3 completed with related hydroxamic acids (Rockwell, A.; Melden, M.; Copeland, R. A.; Hardman, K.; Decicco, C. P. and DeGrado, W. F. J. Am. Chem. Soc. 1996, 118, 10337–10338). Based on the assumption of competitive inhibiton, the IC50 values were converted to Ki values.

Acute Cartilage Degradation Rat Model

A novel in vivo model of acute cartilage degradation in rats has been characterized as a method to determine the proteoglycan content in the synovial fluid after the induction of cartilage degradation. Experimental groups exhibit increased levels of proteoglycan content in their synovial fluid versus control rats. The criteria to demonstrate a compound's activity in this model, is the ability to inhibit the demonstration of cartilage degradation, as measured by increased proteoglycan content in the synovial fluid of rats after compound administration. Indomethacin, a non-steroidal anti-inflammatory drug is inactive in this model. Indomethacin administration does not inhibit the demonstration of cartilage degradation in experimental animals. In contrast, administration of a compound of this invention significantly inhibited the demonstration of cartilage degradation in this model.

TNF Human Whole Blood Assay

Blood is drawn from normal donors into tubes containing 143 USP units of heparin/10 ml. 225 ul of blood is plated directly into sterile polypropylene tubes. Compounds are diluted in DMSO/serum free media and added to the blood samples so the final concentration of compounds are 50, 10, 5, 1, 0.5, 0.1, and .01 $\mu$M. The final concentration of DMSO does not exceed 0.5%. Compounds are preincubated for 15 minutes before the addition of 100 ng/ml LPS. Plates are incubated for 5 hours in an atmosphere of 5% $CO_2$ in air. At the end of 5 hours, 750 ul of serum free media is added to each tube and the samples are spun at 1200 RPM for 10 minutes. The supernatant is collected off the top and assayed for TNF-alpha production by a standard sandwich ELISA. The ability of compounds to inhibit TNF-alpha production by 50% compared to DMSO treated cultures is given by the IC50 value.

TNF Induction In Mice

Test compounds are administered to mice either I.P. or P.O. at time zero. Immediately following compound administration, mice receive an I.P. injection of 20 mg of D-galactosamine plus 10 μg of lipopolysaccharide. One hour later, animals are anesthetized and bled by cardiac puncture. Blood plasma is evaluated for TNF levels by an ELISA specific for mouse TNF. Administration of representative compounds of the present invention to mice results in a dose-dependent suppression of plasma TNF levels at one hour in the above assay.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory and antiarthritic agent.

The compounds of this invention can be administered by any means that produces contact of the active agent with the agent's site of action in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition. The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also prepared by filling standard two-piece hard gelatin capsules each with 100 milligrams of powdered active ingredient, 150 milligrams of lactose, 50 milligrams of cellulose, and 6 milligrams magnesium stearate.

| Syrup | |
|---|---|
| | Wt. % |
| Active Ingredient | 10 |
| Liquid Sugar | 50 |
| Sorbitol | 20 |
| Glycerine | 5 |
| Flavor, Colorant and Preservative | as required |
| Water | as required |

The final volume is brought up to 100% by the addition of distilled water.

| Aqueous Suspension | |
|---|---|
| | Wt. % |
| Active Ingredient | 10 |
| Sodium Saccharin | 0.01 |
| Keltrol ® (Food Grade Xanthan Gum) | 0.2 |
| Liquid Sugar | 5 |

| Aqueous Suspension -continued | |
|---|---|
| | Wt. % |
| Flavor, Colorant and Preservative | as required |
| Water | as required |

Xanthan gum is slowly added into distilled water before adding the active ingredient and the rest of the formulation ingredients. The final suspension is passed through a homogenizer to assure the elegance of the final products.

| Resuspendable Powder | |
|---|---|
| | Wt. % |
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel | |
|---|---|
| | Wt. % |
| Active Ingredient | 10 |
| Sodium Saccharin | 0.02 |
| Gelatin | 2 |
| Flavor, Colorant and Preservative | as required |
| Water | as required |

Gelatin is prepared in hot water. The finely pulverized active ingredient is suspended in the gelatin solution and then the rest of the ingredients are mixed in. The suspension is filled into a suitable packaging container and cooled down to form the gel.

| Semi-Solid Paste | |
|---|---|
| | Wt. % |
| Active Ingredient | 10 |
| Gelcarin ® (Carrageenin gum) | 1 |
| Sodium Saccharin | 0.01 |
| Gelatin | 2 |
| Flavor, Colorant and Preservative | as required |
| Water | as required |

Gelcarin® is dissolved in hot water (around 80° C.) and then the fine-powder active ingredient is suspended in this solution. Sodium saccharin and the rest of the formulation ingredients are added to the suspension while it is still warm. The suspension is homogenized and then filled into suitable containers.

| Emulsifiable Paste | |
|---|---|
| | Wt. % |
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent, especially non-steroidal anti-inflammatory drugs (NSAID's). The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of osteoarthritis or rheumatoid arthritis, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What it claimed is:

1. A compound of formula I:

$$\underset{\text{B}}{\overset{R^1\ R^2\ \overset{O}{\underset{}{}}\ \overset{O}{\underset{}{}}}{A\diagdown\underset{N}{\diagup}\diagdown\underset{S}{\diagup}\diagdown\underset{C}{\diagup}R^3\ (R^4)_s}}$$ I or a stereoisomer or pharmaceutically acceptable salt form thereof, wherein;

A is selected from $COR^5$, $-CO_2H$, $CH(R)CO_2H$, $-CO_2R^6$, $-CONHOH$, $-CH(R)CONHOH$, $-CONHOR^5$, $-CONHOR^6$, $-NHR^a$, $-N(OH)COR^5$, $-SH$, $-CH_2SH$, $-SONHR^a$, $SN_2H_2R^a$, $PO(OH)_2$, and $PO(OH)NHR^a$;

ring B is a 5–10 membered cyclic sulfonamiide containing from 0–2 additional heteroatoms selected from O, $NR^b$, and $S(O)_p$, 0–1 carbonyl groups and 0–1 double bonds and ring B is substituted with 0–1 $R^{b'}$;

ring C is phenyl $R^1$ is selected from H, Q, $C_{1-10}$ alkylene-Q, $C_{2-10}$ alkenylene-Q, $C_{2-10}$ alkynylene-Q, $(CRR')_rO(CRR')_r$—Q, $(CRR')_rNR^a(CRR')_r$—Q, $(CRR')_rC(O)(CRR')_r$—Q, $(CRR')_rC(O)O(CRR')_r$—Q, $(CRR')_rOC(O)(CRR')_r$—Q, $(CRR')_rC(O)NR_a(CRR')_r$—Q, $(CRR')_rNR^aC(O)(CRR')_r$—Q, $(CRR')_rOC(O)O(CRR')_r$—Q, $(CRR')_rOC(O)NR^a(CRR')_r$—Q, $(CRR')_rNR^aC(O)O(CRR')_r$—Q, $(CRR')_rNR^aC(O)NR^a(CRR')_r$—Q, $(CRR')_rS(O)_p(CRR')_r$—Q, $(CRR')_rSO_2NR^a(CRR')_r$—Q, $(CRR')_rNR^aSO_2(CRR')_r$—Q, $(CRR')_rNR^aSO_2NR^a(CRR')_r$—Q, $(CRR')_rNR^aC(O)(CRR')_r$NHQ, $(CRR')_rNR^aC(O)(CRR')_r$NHC(O)OR^a$, and $(CRR')_rNR^aC(O)(CRR')_rNHC(O)(CRR')_rNHC(O)OR^a$;

R, at each occurrence, is independently selected from H, $CH_3$, $CH_2CH_3$, $CH(CH_3)_2$, $CH=CH_2$, $CH=CHCH_3$, and $CH_2CH=CH_2$;

R', at each occurrence, is independently selected from H, $CH_3$, $CH_2CH_3$, and $CH(CH_3)_2$;

alternatively, R and R' together with the carbon to which they are attached form a cyclopropyl, cyclobutyl or cyclopentyl group;

Q, at each occurence, is selected from H, a $C_{3-13}$ carbocyclic residue substituted with 0–5 $R^c$ and a 5–14 membered heterocyclic system containing from 1–4 heteroatoms selected from the group consisting of N, O, and S and substituted with 0–5 $R^c$;

$R^2$ is selected from H, $C_{1-10}$ alkylene-H, $C_{2-10}$ alkenylene-H, $C_{2-10}$ alkynylene-H, $(CRR')_rO(CRR')_r$—H, $(CRR')_rNR^a(CRR')_r$—H, $(CRR')_rC(O)(CRR')_r$—H, $(CRR')_rC(O)O(CRR')_r$—H, $(CRR')_rOC(O)(CRR')_r$—H, $(CRR')_rC(O)NR^a(CRR')_r$—H, $(CRR')_rNR^aC(O)(CRR')_r$—H, $(CRR')_rOC(O)O(CRR')_r$—H, $(CRR')_rOC(O)NR^a(CRR')_r$—H, $(CRR')_rNR^aC(O)O(CRR')_r$—H, $(CRR')_rNR^aC(O)NR^a(CRR')_r$—H, $(CRR')_rS(O)_p(CRR')_r$—H, $(CRR')_rSO_2NR^a(CRR')_r$—H, $(CRR')_{r'}NR^aSO_2(CRR')_r$—H, and $(CRR')_{r'}NR^aSO_2NR^a(CRR')_r$—H;

$R^3$ is $U-X-Y-X^1-Z$;

U is absent or is selected from: O, $NR^a$, $C(O)$, $C(O)O$, $OC(O)$, $C(O)NR^a$, $NR^aC(O)$, $OC(O)O$, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from $C_{1-10}$ alkylene, $C_{2-10}$ alkenylene, and $C_{2-10}$ alkynylene;

$X^1$ is absent or selected from $C_{1-10}$ alkylene, $C_{2-10}$ alkenylene, and $C_{2-10}$ alkynylene;

Y is absent or selected from O, $NR^a$, $S(O)_p$, $S(O)_pNR^a$, $C(O)NR^a$, and $C(O)$, provided that when U and Y are present, X is present;

Z is selected from H, a $C_{3-13}$ carbocyclic residue substituted with 0–5 $R^d$ and a 5–14 membered heterocyclic system containing from 1–4 heteroatoms selected from the group consisting of N, O, and S and substituted with 0–5 $R^d$;

$R^4$, at each occurence, is selected from $C_{1-6}$ alkyl, $OR^a$, Cl, F, Br, I, $=O$, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{3-6}$ carbocyclic residue, and a 5–10 membered heterocyclic system containing from 1–4 heteroatoms selected from the group consisting of N, O, and S;

$R^a$, at each occurrence, is independently selected from H, $C_{1-4}$ alkyl, phenyl or benzyl;

$R^{a'}$, at each occurrence, is independently selected from H, $C_{1-4}$ alkyl, phenyl or benzyl;

$R^{a''}$, at each occurrence, is independently selected from $C_{1-4}$ alkyl, phenyl or benzyl;

alternatively, $R^a$ and $R^{a'}$ taken together with the nitrogen to which they are attached form a 5 or 6 membered ring containing from 0–1 additional heteroatoms selected from the group consisting of N, O, and S;

$R^b$ is selected from H, $C_{1-6}$ alkyl, phenyl, benzyl, $C(O)R^a$, $C(O)NR^aR^{a'}$, $S(O)_2NR^aR^{a'}$, and $S(O)_pR^{a''}$;

$R^{b'}$ is selected from H, Q, $C_{1-10}$ alkylene-Q, $C_{2-10}$ alkenylene-Q, $C_{2-10}$ alkynylene-Q, $(CRR')_rO(CRR')_r$—Q, $(CRR')_rNR^a(CRR')_r$—Q, $(CRR')_rC(O)(CRR')_r$—Q, $(CRR')_rC(O)O(CRR')_r$—Q, $(CRR')_rOC(O)(CRR')_r$—Q, $(CRR')_rC(O)NR^a(CRR')_r$—Q, $(CRR')_rNR^aC(O)(CRR')_r$—Q, $(CRR')_rOC(O)O(CRR')_r$—Q, $(CRR')_rOC(O)NR^a(CRR')_r$—Q, $(CRR')_rNR^aC(O)O(CRR')_r$—Q, $(CRR')_rNR^aC(O)NR^a(CRR')_r$—Q, $(CRR')_rS(O)_p(CRR')_r$—Q, $(CRR')_rSO_2NR^a(CRR')_r$—Q, $(CRR')_rNR^aSO_2(CRR')_r$—Q, $(CRR')_rNR^aSO_2NR^a(CRR')_r$—Q, $(CRR')_rNR^aC(O)(CRR')_r$NHQ, $(CRR')_rNR^aC(O)(CRR')_rNHC(O)OR^a$, and $(CRR')_rNR^aC(O)(CRR')_rNHC(O)(CRR')_rNHC(O)OR^a$;

$R^c$, at each occurrence, is independently selected from $C_{1-6}$ alkyl, $OR^a$, Cl, F, Br, I, $=O$, CN, $NO_2$, $NR^aR^{a'}$, $C(O)R^a$, $C(O)OR^a$, $C(O)NR^aR^{a'}$, $NR^aC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $-CH(=NOH)$, $-C(=NOH)CH_3$, $(CRR')_sO(CRR')_sR^{c'}$, $(CRR')_sS(O)_p(CRR')_sR^{c'}$, $(CRR')_sNR^a(CRR')_sR^{c'}$, $C_{3-10}$ carbocyclic residue and a 5–14 membered heterocyclic system containing from 1–4 heteroatoms selected from the group consisting of N, O, and S;

$R^{c'}$, at each occurrence, is independently selected from phenyl substituted with 0–3 $R^b$, biphenyl substituted with 0–2 $R^b$, naphthyl substituted with 0–3 $R^b$ and a 5–10 membered heteroaryl system containing from 1–4 heteroatoms selected from the group consisting of N, O, and S and substituted with 0–3 $R^b$;

$R^d$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $NR^aC(O)NR^aR^{a'}$, $OC(O)NR^aR^{a'}$, $NR^aC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{3-10}$ carbocyclic residue and a 5–14 membered heterocyclic system containing from 1–4 heteroatoms selected from the group consisting of N, O, and S;

$R^5$, at each occurrence, is selected from H, $C_{1-10}$ alkyl substituted with 0–2 $R^e$, and $C_{1-8}$ alkyl substituted with 0–2 $R^f$;

$R^e$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $S(O)_2NR^aR^{a'}$, $S(O)_pR^{a''}$, $CF_3$, and $CF_2CF_3$;

$R^f$, at each occurrence, is selected from phenyl substituted with 0–2 $R^e$ and biphenyl substituted with 0–2 $R^e$;

$R^6$, at each occurrence, is selected from phenyl, naphthyl, $C_{1-10}$ alkyl-phenyl-$C_{1-6}$ alkyl-, $C_{3-11}$ cycloalkyl, $C_{1-6}$ alkylcarbonyloxy-$C_{1-3}$ alkyl-, $C_{1-6}$ alkoxycarbonyloxy-$C_{1-3}$ alkyl-, $C_{2-10}$ alkoxycarbonyl, $C_{3-6}$ cycloalkylcarbonyloxy-$C_{1-3}$ alkyl-, $C_{3-6}$ cycloalkoxycarbonyloxy-$C_{1-3}$ alkyl-, $C_{3-6}$ cycloalkoxycarbonyl, phenoxycarbonyl, phenyloxycarbonyloxy-$C_{1-3}$ alkyl-, phenylcarbonyloxy-$C_{1-3}$ alkyl-, $C_{1-6}$ alkoxy-$C_{1-6}$ alkylcarbonyloxy-$C_{1-3}$ alkyl-, [5-($C_1$–$C_5$ alkyl)-1,3-dioxa-cyclopenten-2-one-yl]methyl, (5-aryl-1,3-dioxa-cyclopenten-2-one-yl)methyl, —$C_{1-10}$ alkyl-$NR^7R^{7a}$, —$CH(R^8)OC(=O)R^9$, —$CH(R^8)OC(=O)OR^9$, and

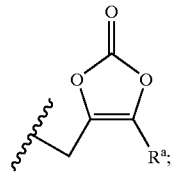

$R^7$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^{7a}$ is selected from H and $C_{1-10}$ alkyl, $C_{2-6}$ alkenyl, $C_{3-6}$ cycloalkyl-$C_{1-3}$ alkyl-, and phenyl-$C_{1-6}$ alkyl-;

$R^8$ is selected from H and $C_{1-4}$ linear alkyl;

$R^9$ is selected from H, $C_{1-8}$ alkyl substituted with 1–2 $R^g$, $C_{3-8}$ cycloalkyl substituted with 1–2 $R^g$, and phenyl substituted with 0–2 $R^e$;

$R^g$, at each occurrence, is selected from $C_{1-4}$ alkyl, $C_{3-8}$ cycloalkyl, $C_{1-5}$ alkoxy, phenyl substituted with 0–2 $R^e$;

p, at each occurrence, is selected from 0, 1, and 2;

r, at each occurrence, is selected from 0, 1, 2, 3, 4, 5, 6, 7, 8, 9, and 10;

r', at each occurrence, is selected from 1, 2, 3, 4, 5, 6, 7, 8, 9, and 10; and, s, at each occurence, is selected from 0, 1, 2, and 3.

2. A compound according to claim 1, wherein;

A is selected from $COR^5$, —$CO_2H$, $CH_2CO_2H$, —CONHOH, —$CONHOR^5$, —$CONHOR^6$, —N(OH)$COR^5$, —SH, and —$CH_2SH$;

ring B is a 6–8 membered cyclic sulfonamide containing from 0–2 additional heteroatoms selected from O, $NR^b$, and $S(O)_p$, and 0–1 carbonyl groups;

$R^1$ is selected from H, $C_{1-10}$ alkylene-Q, $C_{2-10}$ alkenylene-Q, $C_{2-10}$ alkynylene-Q, $(CH_2)_rO(CH_2)_{r'}$—Q, $(CH_2)_{r'}NR^a(CH_2)_{r'}$—Q, $(CH_2)_rC(O)(CH_2)_{r'}$—Q, $(CH_2)_rC(O)NR^a(CH_2)_{r'}$—Q, $(CH_2)_rNR^aC(O)(CH_2)_{r'}$—Q, $(CH_2)_rOC(O)NR^a(CH_2)_{r'}$—Q, $(CH_2)_rNR^aC(O)O(CH_2)_{r'}$—Q, $(CH_2)_rNR^aC(O)NR^a(CH_2)_{r'}$—Q, $(CH_2)_rS(O)_p(CH_2)_{r'}$—Q, $(CH_2)_rSO_2NR^a(CH_2)_{r'}$—Q, $(CH_2)_{r'}NR^aSO_2(CH_2)_{r'}$—Q, and $(CH_2)_rNR^aSO_2NR^a(CH_2)_{r'}$—Q;

Q is selected from H, a $C_{3-10}$ carbocyclic residue substituted with 0–5 $R^c$ and a 5–10 membered heterocyclic system containing from 1–4 heteroatoms selected from the group consisting of N, O, S and substituted with 0–5 $R^c$;

$R^2$ is selected from H, $C_{1-6}$ alkylene-H, $C_{2-6}$ alkenylene-H, $C_{2-6}$ alkynylene-H, $(CH_2)_rO(CH_2)_{r'}$—H, $(CH_2)_{r'}NR^a(CH_2)_{r'}$—H, $(CH_2)_rC(O)(CH_2)_{r'}$—H, $(CH_2)_rC(O)NR^a(CH_2)_{r'}$—H, $(CH_2)_rNR^aC(O)(CH_2)_{r'}$—H, $(CH_2)_{r'}SO_2NR^a(CH_2)_{r'}$—H, and $(CH_2)_rNR^aSO_2(CH_2)_{r'}$—H;

U is absent or is selected from: O, $NR^a$, $C(O)$, $C(O)NR^a$, $NR^aC(O)$, $OC(O)O$, $OC(O)NR^a$, $NR^aC(O)O$, $NR^aC(O)NR^a$, $S(O)_p$, $S(O)_pNR^a$, $NR^aS(O)_p$, and $NR^aSO_2NR^a$;

X is absent or selected from $C_{1-6}$ alkylene, $C_{2-6}$ alkenylene, $C_{2-6}$ alkynylene;

$X^1$ is absent or selected from $C_{1-6}$ alkylene, $C_{2-6}$ alkenylene, and $C_{2-6}$ alkynylene;

Z is selected from H, a $C_{5-10}$ carbocyclic residue substituted with 0–5 $R^d$ and a 5–10 membered heterocyclic system containing from 1–4 heteroatoms selected from the group consisting of N, O, S and substituted with 0–5 $R^d$;

$R^4$, at each occurrence, is selected from $C_{1-6}$ alkyl, $OR^a$, Cl, F, Br, I, =O, CN, $NO_2$, $NR^aR^{a'}$, $C(O)R^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2 NR^aR^{a'}$, $NR^aS(O)_2O$, $S(O)_pR^{a''}$, $CF_3$, $CF_2CF_3$, and a 5–10 membered heterocyclic system containing from 1–4 heteroatoms selected from the group consisting of N, O, and S;

$R^c$, at each occurrence, is independently selected from $C_{1-6}$ alkyl, $OR^a$, Cl, F, Br, I, =O, CN, $NO_2$, $NR^aR^{a'}$, $C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{5-10}$ carbocyclic residue and a 5–10 membered heterocyclic system containing from 1–4 heteroatoms selected from the group consisting of N, O, and S;

$R^d$, at each occurrence, is independently selected from $C_{1-6}$ alkyl, $OR^a$, Cl, F, Br, I, =O, CN, $NO_2$, $NR^aR^{a'}C(O)R^a$, $C(O)OR^a$, $C(O)NR^aR^{a'}$, $R^aNC(O)NR^aR^{a'}$, $OC(O)NR^aR^{a'}$, $R^aNC(O)O$, $S(O)_2NR^aR^{a'}$, $NR^aS(O)_2R^{a''}$, $NR^aS(O)_2NR^aR^{a'}$, $OS(O)_2NR^aR^{a'}$, $NR^aS(O)_2O$, $S(O)_pR^{a''}$, $CF_3$, $CF_2CF_3$, $C_{3-10}$ carbocyclic residue and a 5–10 membered heterocyclic system containing from 1–4 heteroatoms selected from the group consisting of N, O, and S;

r, at each occurrence, is selected from 0, 1, 2, 3, 4, and 5; and, r', at each occurrence, is selected from 1, 2, 3, 4, and 5.

3. A compound according to claim 2, wherein;

A is selected from —CO$_2$H, CH$_2$CO$_2$H, —CONHOH, —CONHOR$^5$, and —N(OH)COR$^5$;

ring B is a 6–8 membered cyclic sulfonamide containing from 0–1 additional heteroatoms selected from O, NR$^b$, and S(O)$_p$, and 0–1 carbonyl groups;

Q is selected from H, a C$_{5-10}$ carbocyclic residue substituted with 0–3 R$^c$ and a 5–10 membered heterocyclic system containing from 1–4 heteroatoms selected from the group consisting of N, O, and S and substituted with 0–3 R$^c$;

R$^2$ is selected from H, CH$_3$, and CH$_2$CH$_3$; U is absent or is selected from: O, NR$^a$, C(O), C(O)NR$^a$, NR$^a$C(O), NR$^a$C(O)NR$^a$, S(O)$_p$, S(O)$_p$NR$^a$, NR$^a$S(O)$_p$, and NR$^a$SO$_2$NR$^a$;

X is absent or selected from C$_{1-2}$ alkylene, C$_{2-3}$ alkenylene, and C$_{2-3}$ alkynylene;

X$^1$ is absent or selected from C$_{1-2}$ alkylene, C$_{2-3}$ alkenylene, and C$_{2-3}$ alkynylene;

Z is selected from H, a C$_{5-6}$ carbocyclic residue substituted with 0–5 R$^d$ and a 5–10 membered heterocyclic system containing from 1–4 heteroatoms selected from the group consisting of N, O, and S and substituted with 0–5 R$^d$; and, R$^d$, at each occurrence, is selected from C$_{1-6}$ alkyl, OR$^a$, Cl, F, Br, I, =O, CN, NO$_2$, NR$^a$R$^{a'}$, C(O)R$^a$, C(O) NR$^a$R$^{a'}$, R$^a$NC(O)NR$^a$R$^{a'}$, OC(O)NR$^a$R$^{a'}$, R$^a$NC(O)O, S(O)$_2$NR$^a$R$^{a'}$, NR$^a$S(O)$_2$R$^{a''}$, NR$^a$S(O)$_2$NR$^a$R$^{a'}$, OS(O)$_2$ NR$^a$R$^{a'}$, NR$^a$S(O)$_2$O, S(O)$_p$R$^{a''}$, CF$_3$, CF$_2$CF$_3$, and a 5–6 membered heterocyclic system containing from 1–4 heteroatoms selected from the group consisting of N, O, and S.

4. A compound according to claim 3, wherein;

A is selected from —CO$_2$H, CH$_2$CO$_2$H, —CONHOH, and —CONHOR$^5$;

ring B is a 6–7 membered cyclic sulfonamide containing from 0–1 additional heteroatoms selected from NR$^b$;

R$^1$ is selected from H, C$_{1-6}$ alkylene-Q, C$_{2-6}$ alkenylene-Q, C$_{2-6}$ alkynylene-Q, (CH$_2$)$_r$O(CH$_2$)$_r$—Q, (CH$_2$)$_r$ NR$^a$(CH$_2$)$_r$—Q, (CH$_2$)$_r$C(O)(CH$_2$)$_r$—Q, (CH$_2$)$_r$C(O) NR$^a$(CH$_2$)$_r$—Q, (CH$_2$)$_r$NR$^a$C(O)(CH$_2$)$_r$—Q, (CH$_2$)$_r$ OC(O)NR$^a$(CH$_2$)$_r$—Q, (CH$_2$)$_r$NR$^a$C(O)O(CH$_2$)$_r$—Q, (CH$_2$)$_r$NR$^a$C(O)NR$^a$(CH$_2$)$_r$—Q, (CH$_2$)$_r$S(O)$_p$(CH$_2$)$_r$ —Q, (CH$_2$)$_r$SO$_2$NR$^a$(CH$_2$)$_r$—Q, (CH$_2$)$_r$ NR$^a$SO$_2$ (CH$_2$)$_r$—Q, and (CH$_2$)$_r$NR$^a$SO$_2$NR$^a$(CH$_2$)$_r$ —Q;

Q is selected from H, a C$_{5-6}$ carbocyclic residue substituted with 0–3 R$^c$ and a 5–6 membered heterocyclic system containing from 1–4 heteroatoms selected from the group consisting of N, O, and S and substituted with 0–3 R$^c$;

R$^2$ is H;

X is absent or selected from CH$_2$ and CH$_2$CH$_2$;

X$^1$ is absent;

Y is absent or selected from S(O)$_p$NR$^a$ and C(O)NR$^a$, provided that when U and Y are present, X is present;

Z is selected from H, phenyl substituted with 0–5 R$^d$ and a 5–10 membered aromatic heterocyclic system containing from 1–4 heteroatoms selected from the group consisting of N, O, and S and substituted with 0–5 R$^d$;

R$^c$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, R$^a$NC(O)NR$^a$R$^{a'}$, OC(O)NR$^a$R$^{a'}$, R$^a$NC(O)O, S(O)$_2$NR$^a$R$^{a'}$, NR$^a$S(O)$_2$ R$^{a''}$, NR$^a$S(O)$_2$NR$^a$R$^{a'}$, OS(O)$_2$NR$^a$R$^{a'}$, NR$^a$S(O)$_2$O, S(O)$_p$R$^{a''}$, CF$_3$, CF$_2$CF$_3$, C$_{5-6}$ carbocyclic residue and a 5–6 membered heterocyclic system containing from 1–4 heteroatoms selected from the group consisting of N, O, and S;

R$^d$, at each occurrence, is independently selected from C$_{1-6}$ alkyl, OR$^a$, Cl, F, Br, I, =O, CN, NO$_2$, NR$^a$R$^{a'}$, C(O)R$^a$, C(O)OR$^a$, C(O)NR$^a$R$^{a'}$, R$^a$NC(O)NR$^a$R$^{a'}$, OC(O)NR$^a$R$^{a'}$, R$^a$NC(O)O, S(O)$_2$NR$^a$R$^{a'}$, NR$^a$S(O)$_2$ R$^{a''}$, NR$^a$S(O)$_2$NR$^a$R$^{a'}$, OS(O)$_2$NR$^a$R$^{a'}$, NR$^a$S(O)$_2$O, S(O)$_p$R$^{a''}$, CF$_3$, CF$_2$CF$_3$, C$_{3-6}$ carbocyclic residue and a 5–6 membered heterocyclic system containing from 1–4 heteroatoms selected from the group consisting of N, O, and S; and, s, at each occurrence, is selected from 0 and 1.

5. A compound according to claim 4, wherein the compound is of formula Ia;

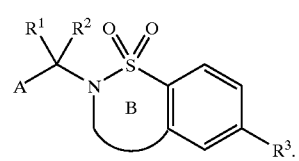

6. A compound according to claim 1, wherein the compound is selected from:

4,5-dihydro-N-hydroxy-1,2,5-benzothiadiazepine-2(3H)-acetamide-1,1-dioxide;

4,5-dihydro-N-hydroxy-7-methoxy-1,2,5-benzothiadiazepine-2(3H)-acetamide-1,1-dioxide;

(R)-4,5-dihydro-N-hydroxy-alpha-methyl-1,2,5-benzothiadiazepine-2(3H)-acetamide-1,1-dioxide;

(R)-4,5-dihydro-N-hydroxy-7-methoxy-alpha-methyl-1,2,5-benzothiadiazepine-2(3H)-acetamide-1,1-dioxide;

(R)-4,5-dihydro-N-hydroxy-7-methoxy-alpha-(1-methylethyl)-1,2,5-benzothiadiazepine-2(3H)-acetamide-1,1-dioxide;

N-hydroxy-2(R)-[7-(3,5-dimethylbenzyloxy)-2,3,4,5-tetrahydrobenzo[1,2,5-f]thiadiazepine-1,1-dioxide]-propanamide;

N-hydroxy-2(R)-[7-(3,5-dichlorobenzyloxy)-2,3,4,5-tetrahydrobenzo[1,2,5-f]thiadiazepine-1,1-dioxide]-propanamide;

N-hydroxy-2(R)-[7-(3,5-dimethoxybenzyloxy)-2,3,4,5-tetrahydrobenzo[1,2,5-f]thiadiazepine-1,1-dioxide]-propanamide;

N-hydroxy-2(R)-[7-(3,5-dibromobenzyloxy)-2,3,4,5-tetrahydrobenzo[1,2,5-f]thiadiazepine-1,1-dioxide]-propanamide;

N-hydroxy-2(R)-[7-(3,5-diethoxybenzyloxy)-2,3,4,5-tetrahydrobenzo[1,2,5-f]thiadiazepine-1,1-dioxide]-propanamide;

N-hydroxy-2(R)-[7-(2,6-dichloropyridyl-4-methyleneoxy)-2,3,4,5-tetrahydrobenzo[1,2,5-f]thiadiazepine-1,1-dioxide]-propanamide;

N-hydroxy-2(R)-[7-(3-amino-5-methylbenzyloxy)-2,3,4,5-tetrahydrobenzo[1,2,5-f]thiadiazepine-1,1-dioxide]-propanamide;

N-hydroxy-2(R)-[7-(3,5-dimethylbenzyloxy)-2,3,4,5-tetrahydrobenzo[1,2,5-f]thiadiazepine-1,1-dioxide]-3-methylbutanamide;

N-hydroxy-2(R)-[7-(3,5-dimethoxybenzyloxy)-2,3,4,5-tetrahydrobenzo[1,2,5-f]thiadiazepine-1,1-dioxide]-3-methylbutanamide;

N-hydroxy-2(R)-[7-(3,5-diethoxybenzyloxy)-2,3,4,5-tetrahydrobenzo[1,2,5-f]thiadiazepine-1,1-dioxide]-3-methylbutanamide;

N-hydroxy-2(R)-[7-(4,5-dimethylthiazolyl-2-methyleneoxy)-2,3,4,5-tetrahydrobenzo[1,2,5-f]thiadiazepine-1,1-dioxide]-3-methylbutanamide;

N-hydroxy-2 (R)-[7-(3,5-dimethylbenzyloxy)-2,3,4,5-tetrahydrobenzo[1,2,5-f]thiadiazepine-1,1-dioxide]-4-methylpentanamide;

N-hydroxy-2(R)-[7-(3,5-dibromobenzyloxy)-2,3,4,5-tetrahydrobenzo[1,2,5-f]thiadiazepine-1,1-dioxide]-4-methylpentanamide;

N-hydroxy-2(R)-[7-(2-nitrophenoxy)-2,3,4,5-tetrahydrobenzo[1,2,5-f]thiadiazepine-1,1-dioxide]-4-methylpentanamide;

N-hydroxy-2(R)-[7-(2-aminophenoxy)-2,3,4,5-tetrahydrobenzo[1,2,5-f]thiadiazepine-1,1-dioxide]-4-methylpentanamide;

N-hydroxy-2(R)-[7-(2,6-dichloropyridyl-4-methyleneoxy)-2,3,4,5-tetrahydrobenzo[1,2,5-f]thiadiazepine-1,1-dioxide]-4-methylpentanamide;

N-hydroxy-2(R)-[7-(pyridyl-4-methyleneoxy)-2,3,4,5-tetrahydrobenzo[1,2,5-f]thiadiazepine-1,1-dioxide]-4-methylpentanamide;

N-hydroxy-2(R)-[7-(3,5-dichlorobenzyloxy)-2,3,4,5-tetrahydrobenzo[1,2,5-f]thiadiazepine-1,1-dioxide]-4-methylpentanamide;

N-hydroxy-2(R)-[7-(3,5-dimethoxybenzyloxy)-2,3,4,5-tetrahydrobenzo[1,2,5-f]thiadiazepine-1,1-dioxide]-4-methylpentanamide;

N-hydroxy-2(R)-[7-(3,5-diethoxybenzyloxy)-2,3,4,5-tetrahydrobenzo[1,2,5-f]thiadiazepine-1,1-dioxide]-4-methoxycarbonylbutanamide;

N-hydroxy-2(R)-[7-(3,5-dimethoxybenzyloxy)-2,3,4,5-tetrahydrobenzo[1,2,5-f]thiadiazepine-1,1-dioxide]-4 methoxycarbonylbutanamide;

N-hydroxy-2(R)-[7-amino-2,3,4,5-tetrahydro-benzo[1,2,5-f]thiadiazepine-1,1-dioxide]-4-methylpentamide;

N-hydroxy-2(R)-[7-(N-acetylamino)-2,3,4,5-tetrahydro-benzo[1,2,5-f]thiadiazepine-1,1-dioxide]-4-methylpentamide;

N-hydroxy-2(R)-[7-(N-(2-phenylacetylamino)-2,3,4,5-tetrahydro-benzo[1,2,5-f]thiadiazepine-1,1-dioxide]-4-methylpentamide;

N-hydroxy-2(R)-[2,3,4,5-tetrahydro-benzo[1,2,5-f]thiadiazepine-1,1-dioxide]-4-methylpentamide;

N-hydroxy-2(R)-[7-(N-(3,5-dimethoxymethyleneamino)-2,3,4,5-tetrahydro-benzo[1,2,5-f]thiadiazepine-1,1-dioxide]-4-methylpentamide;

N-hydroxy-2(R)-[7-(N-(3,5-dimethylphenylmethyleneamino)-2,3,4,5-tetrahydro-benzo[1,2,5-f]thiadiazepine-1,1-dioxide]propylamide;

N-hydroxy-2(R)-[7-(N-benzoylamino)-2,3,4,5-tetrahydro-benzo[1,2,5-f]thiadiazepine-1,1-dioxide]propylamide;

N-hydroxy-2(R)-[7-(N-3,5-dimethoxybenzoylamino)-2,3,4,5-tetrahydro-benzo[1,2,5-f]thiadiazepine1,1-dioxide]propylamide;

N-hydroxy-2(R)-[7-(N-3,5-dimethylbenzoylamino)-2,3,4,5-tetrahydro-benzo[1,2,5-f]thiadiazepine-1,1-dioxide]propylamide;

N-hydroxy-2(R)-[7-(phenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl)methyl]acetamide;

N-hydroxy-2(R)-[7-(3,5-dimethoxyphenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl)methyl]acetamide;

N-hydroxy-2(R)-[7-(3,5-dimethylphenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl)methyl]acetamide;

N-hydroxy-2(R)-[7-(3,5-dibromophenylmethyleneoxy)-2,3,4,5-tetrahydro-benzo[1,2,5-f]thiadiazepine-1,1-dioxide]-2-[(3,4,4-trimethyl-2,5-dioxa-1-imidazolidinyl)methyl]acetamide;

(R)-3,4-Dihydro-N-Hydroxy-alpha-(1-methylethyl)-2H-1,2-benzothiazine-2-acetamide-1,1-dioxide;

(R)-3,4-Dihydro-N-Hydroxy-alpha-2H-1,2-benzothiazine-2-acetamide-1,1-dioxide;

N-hydroxy-2(R)-[7-(3,5-dimethoxybenzyloxy)-2,3,4,5-tetrahydrobenzo[1,2,5-f]thiadiazepine-1,1-dioxide]-5-methoxycarbonylpentanamide;

N-hydroxy-2(R)-[7-(3,5-diethoxybenzyloxy)-2,3,4,5-tetrahydrobenzo[1,2,5-f]thiadiazepine-1,1-dioxide]-5-methoxycarbonylpentanamide;

N-hydroxy-2(R)-[7-(3,5-dimethoxybenzyloxy)-2,3,4,5-tetrahydrobenzo[1,2,5-f]thiadiazepine-1,1-dioxide]-6-methoxycarbonylhexanamide;

N-hydroxy-2(R)-[7-(3,5-dimethoxybenzyloxy)-2,3,4,5-tetrahydrobenzo[1,2,5-f]thiadiazepine-1,1-dioxide]-6-hydroxycarbonylhexanamide;

N-hydroxy-2(R)-[7-(4-nitrophenoxy)-2,3,4,5-tetrahydrobenzo[1,2,5-f]thiadiazepine-1,1-dioxide]-propanamide;

N-hydroxy-2(R)-[7-(4-aminophenoxy)-2,3,4,5-tetrahydrobenzo[1,2,5-f]thiadiazepine-1,1-dioxide]-propanamide;

N-hydroxy-2(R)-[7-(3-methyl-4-nitrophenoxy)-2,3,4,5-tetrahydrobenzo[1,2,5-f]thiadiazepine-1,1-dioxide]-propanamide;

N-hydroxy-2(R)-[7-(2-nitrophenoxy)-2,3,4,5-tetrahydrobenzo[1,2,5-f]thiadiazepine-1,1-dioxide]-4-methylpentanamide;

N-hydroxy-2(R)-[7-(2-aminophenoxy)-2,3,4,5-tetrahydrobenzo[1,2,5-f]thiadiazepine-1,1-dioxide]-4-methylpentanamide;

N-hydroxy-2(R)-[7-(3-nitrophenoxy)-2,3,4,5-tetrahydrobenzo[1,2,5-f]thiadiazepine-1,1-dioxide]-propanamide;

N-hydroxy-2(R)-[7-phenoxy-2,3,4,5-tetrahydrobenzo[1,2,5-f]thiadiazepine-1,1-dioxide]-propanamide;

N-hydroxy-2(R)-[7-(4-methylthio-phenoxy)-2,3,4,5-tetrahydrobenzo[1,2,5-f]thiadiazepine-1,1-dioxide]-propanamide;

N-hydroxy-2(R)-[7-(4-methoxyphenoxy)-2,3,4,5-tetrahydrobenzo[1,2,5-f]thiadiazepine-1,1-dioxide]-propanamide;

N-hydroxy-2(R)-[7-(4-trifluoromethylphenoxy)-2,3,4,5-tetrahydrobenzo[1,2,5-f]thiadiazepine-1,1-dioxide]-propanamide;

N-hydroxy-2(R)-[7-(4-methylsulfonylphenoxy)-2,3,4,5-tetrahydrobenzo[1,2,5-f]thiadiazepine-1,1-dioxide]-propanamide;

N-hydroxy-2(R)-[7-(4-methoxycarbonylphenoxy)-2,3,4,5-tetrahydrobenzo[1,2,5-f]thiadiazepine-1,1-dioxide]-propanamide;

N-hydroxy-2(R)-[7-(4-phenylphenoxy)-2,3,4,5-tetrahydrobenzo[1,2,5-f]thiadiazepine-1,1-dioxide]-propanamide;

N-hydroxy-2(R)-[7-(benzyloxy)-2,3,4,5-tetrahydro-benzo[1,2,5-f]thiadiazepine1,1-dioxide]-2-[(5,5-dimethyl-2,4-dioxa-3-oxazolidinyl)methyl]acetamide;

N-hydroxy-2(R)-[7-(benzyloxy)-2,3,4,5-tetrahydro-benzo[1,2,5-f]thiadiazepine 1,1-dioxide]-3-N-(2-hydroxy-2-methylpropylamidyl)propylamide;

N-hydroxy-2(R)-[7-(benzyloxy)-2,3,4,5-tetrahydro-benzo[1,2,5-f]thiadiazepine 1,1-dioxide]-6-N-[(1,1-dimethylethoxy)carbonyl]hexylamide;

N-hydroxy-2(R)-[7-(3,5-dimethoxybenzyloxy)-2,3,4,5-tetrahydro-benzo[1,2,5-f]thiadiazepine 1,1-dioxide]-6-N-[(1,1-dimethylethoxy)carbonyl]hexylamide;

N-hydroxy-2(R)-[7-(3,5-dimethoxybenzyloxy)-2,3,4,5-tetrahydro-benzo[1,2,5-f]thiadiazepine 1,1-dioxide]-6-amino-hexylamide;

N-hydroxy-2(R)-[7-(3,5-dimethoxybenzyloxy)-2,3,4,5-tetrahydro-benzo[1,2,5-f]thiadiazepine 1,1-dioxide]-6-N-(acetamidyl)-hexylamide;

N-hydroxy-2(R)-[7-(3,5-dimethoxybenzyloxy)-2,3,4,5-tetrahydro-benzo[1,2,5-f]thiadiazepine 1,1-dioxide]-6-N-(methanesulfonyl)-hexylamide;

N-hydroxy-2(R)-[7-(2,6-dimethoxypyridyl-4-methyleneoxy)-2,3,4,5-tetrahydro-benzo[1,2,5-f]thiadiazepine 1,1-dioxide]-6-N-[(1,1-dimethylethoxy)carbonyl]hexylamide;

N-hydroxy-2(R)-[7-(2,6-dimethoxypyridyl-4-methyleneoxy)-2,3,4,5-tetrahydro-benzo[1,2,5-f]thiadiazepine 1,1-dioxide]-6-aminohexylamide;

N-hydroxy-2(R)-[7-(3,5-dimethoxybenzyloxy)-2,3,4,5-tetrahydro-benzo[1,2,5-f]thiadiazepine 1,1-dioxide]-6-N-(benzenesulfonyl)-hexylamide;

N-hydroxy-2(R)-[7-(3,5-dimethoxybenzyloxy)-2,3,4,5-tetrahydro-benzo[1,2,5-f]thiadiazepine 1,1-dioxide]-6-N-(butylsulfonyl)-hexylamide;

N-hydroxy-2(R)-[7-(3,5-dimethoxybenzyloxy)-2,3,4,5-tetrahydro-benzo[1,2,5-f]thiadiazepine 1,1-dioxide]-6-N-[(3,5-dimethyl-4-isoxazolyl)sulfonyl]-hexylamide;

N-hydroxy-2(R)-[7-(3,5-dimethoxybenzyloxy)-2,3,4,5-tetrahydro-benzo[2,5-f]thiadiazepine 1,1-dioxide]-6-N-[(5-chloro-1,3-dimethyl-1H-pyrazol-4-yl)sulfonyl]-hexylamide;

N-hydroxy-2(R)-[7-phenyl-2,3,4,5-tetrahydro-benzo[1,2,5-f]thiadiazepine 1,1-dioxide]propylamide;

N-hydroxy-2(R)-[7-(2-trifluromethylphenyl)-2,3,4,5-tetrahydro-benzo[1,2,5-f]thiadiazepine 1,1-dioxide]propylamide;

N-hydroxy-2(R)-[7-(phenylethynyl)-2,3,4,5-tetrahydro-benzo[1,2,5-f]thiadiazepine 1,1-dioxide]propylamide; and, N-hydroxy-2(R)-[7-(4-biphenylyl)-2,3,4,5-tetrahydro-benzo[1,2,5-f]thiadiazepine 1,1-dioxide]propylamide;

or a pharmaceutically acceptable salt form thereof.

7. A pharmaceutical composition, comprising: a pharmaceutically acceptable carrier and a therapeutically effective amount of a compound of claim 1 or a pharmaceutically acceptable salt form thereof.

8. A method for treating an inflammatory disorder, comprising: administering to a patient in need thereof a therapeutically effective amount of a compound of claim 1 or a pharmaceutically acceptable salt form thereof.

9. A method of treating a condition or disease mediated by MMPs, TNF, aggrecanase, or a combination thereof in a mammal, comprising: administering to the mammal in need of such treatment a therapeutically effective amount of a compound of claim 1 or a pharmaceutically acceptable salt form thereof.

10. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of claim 1 or a pharmaceutically acceptable salt form thereof.

11. A method of treating a condition or disease wherein the disease or condition is referred to as fever, cardiovascular effects, hemorrhage, coagulation, acute phase response, acute infection, shock, graft versus host reaction, autoimmune disease or HIV infection in a mammal comprising administering to the mammal in need of such treatment a therapeutically effective amount of a compound of claim 1 or a pharmaceutically acceptable salt form thereof.

12. A pharmaceutical composition, comprising: a pharmaceutically acceptable carrier and a therapeutically effective amount of a compound of claim 2 or a pharmaceutically acceptable salt form thereof.

13. A pharmaceutical composition, comprising: a pharmaceutically acceptable carrier and a therapeutically effective amount of a compound of claim 3 or a pharmaceutically acceptable salt form thereof.

14. A pharmaceutical composition, comprising: a pharmaceutically acceptable carrier and a therapeutically effective amount of a compound of claim 4 or a pharmaceutically acceptable salt form thereof.

15. A pharmaceutical composition, comprising: a pharmaceutically acceptable carrier and a therapeutically effective amount of a compound of claim 5 or a pharmaceutically acceptable salt form thereof.

16. A pharmaceutical composition, comprising: a pharmaceutically acceptable carrier and a therapeutically effective amount of a compound of claim 6 or a pharmaceutically acceptable salt form thereof.

17. A method for treating an inflammatory disorder, comprising: administering to a patient in need thereof a therapeutically effective amount of a compound of claim 2 or a pharmaceutically acceptable salt form thereof.

18. A method for treating an inflammatory disorder, comprising: administering to a patient in need thereof a therapeutically effective amount of a compound of claim 3 or a pharmaceutically acceptable salt form thereof.

19. A method for treating an inflammatory disorder, comprising: administering to a patient in need thereof a therapeutically effective amount of a compound of claim 4 or a pharmaceutically acceptable salt form thereof.

20. A method for treating an inflammatory disorder, comprising: administering to a patient in need thereof a therapeutically effective amount of a compound of claim 5 or a pharmaceutically acceptable salt form thereof.

21. A method for treating an inflammatory disorder, comprising: administering to a patient in need thereof a therapeutically effective amount of a compound of claim 6 or a pharmaceutically acceptable salt form thereof.

22. A method of treating a condition or disease mediated by MMPs, TNF, aggrecanase, or a combination thereof in a mammal, comprising: administering to the mammal in need of such treatment a therapeutically effective amount of a compound of claim 2 or a pharmaceutically acceptable salt form thereof.

23. A method of treating a condition or disease mediated by MMPs, TNF, aggrecanase, or a combination thereof in a mammal, comprising: administering to the mammal in need of such treatment a therapeutically effective amount of a compound of claim 3 or a pharmaceutically acceptable salt form thereof.

24. A method of treating a condition or disease mediated by MMPs, TNF, aggrecanase, or a combination thereof in a mammal, comprising: administering to the mammal in need of such treatment a therapeutically effective amount of a compound of claim 4 or a pharmaceutically acceptable salt form thereof.

25. A method of treating a condition or disease mediated by MMPs, TNF, aggrecanase, or a combination thereof in a mammal, comprising: administering to the mammal in need of such treatment a therapeutically effective amount of a compound of claim 5 or a pharmaceutically acceptable salt form thereof.

26. A method of treating a condition or disease mediated by MMPs, TNF, aggrecanase, or a combination thereof in a mammal, comprising: administering to the mammal in need of such treatment a therapeutically effective amount of a compound of claim 6 or a pharmaceutically acceptable salt form thereof.

27. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of claim 2 or a pharmaceutically acceptable salt form thereof.

28. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of claim 3 or a pharmaceutically acceptable salt form thereof.

29. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of claim 4 or a pharmaceutically acceptable salt form thereof.

30. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of claim 5 or a pharmaceutically acceptable salt form thereof.

31. A method of treating a condition or disease wherein the disease or condition is referred to as rheumatoid arthritis, osteoarthritis, periodontitis, gingivitis, corneal ulceration, solid tumor growth and tumor invasion by secondary metastases, neovascular glaucoma, multiple sclerosis, or psoriasis in a mammal, comprising: administering to the mammal in need of such treatment a therapeutically effective amount of a compound of claim 6 or a pharmaceutically acceptable salt form thereof.

32. A method of treating a condition or disease wherein the disease or condition is referred to as fever, cardiovascular effects, hemorrhage, coagulation, acute phase response, acute infection, shock, graft versus host reaction, autoimmune disease or HIV infection in a mammal comprising administering to the mammal in need of such treatment a therapeutically effective amount of a compound of claim 2 or a pharmaceutically acceptable salt form thereof.

33. A method of treating a condition or disease wherein the disease or condition is referred to as fever, cardiovascular effects, hemorrhage, coagulation, acute phase response, acute infection, shock, graft versus host reaction, autoimmune disease or HIV infection in a mammal comprising administering to: the mammal in need of such treatment a therapeutically effective amount of a compound of claim 3 or a pharmaceutically acceptable salt form thereof.

34. A method of treating a condition or disease wherein the disease or condition is referred to as fever, cardiovascular effects, hemorrhage, coagulation, acute phase response, acute infection, shock, graft versus host reaction, autoimmune disease or HIV infection in a mammal comprising administering to the mammal in need of such treatment a therapeutically effective amount of a compound of claim 4 or a pharmaceutically acceptable salt form thereof.

35. A method of treating a condition or disease wherein the disease or condition is referred to as fever, cardiovascular effects, hemorrhage, coagulation, acute phase response, acute infection, shock, graft versus host reaction, autoimmune disease or HIV infection in a mammal comprising administering to the mammal in need of such treatment a therapeutically effective amount of a compound of claim 5 or a pharmaceutically acceptable salt form thereof.

36. A method of treating a condition or disease wherein the disease or condition is referred to as fever, cardiovascular effects, hemorrhage, coagulation, acute phase response, acute infection, shock, graft versus host reaction, autoimmune disease or HIV infection in a mammal comprising administering to the mammal in need of such treatment a therapeutically effective amount of a compound of claim 6 or a pharmaceutically acceptable salt form thereof.

\* \* \* \* \*